United States Patent [19]

Konno et al.

[11] Patent Number: 5,086,065

[45] Date of Patent: Feb. 4, 1992

[54] PHENYLALKAN(EN)OIC ACID

[75] Inventors: Mitoshi Konno; Takahiko Nakae; Nobuyuki Hamanaka, all of Osaka, Japan

[73] Assignee: Ono Pharmaceutical Co., Ltd., Osaka, Japan

[21] Appl. No.: 524,521

[22] Filed: May 17, 1990

[30] Foreign Application Priority Data

Jun. 27, 1989 [JP] Japan .................. 1-164213
Dec. 1, 1989 [JP] Japan .................. 1-310545
Jan. 9, 1990 [JP] Japan .................. 2-1799

[51] Int. Cl.$^5$ ............... A61K 31/425; C07D 275/03
[52] U.S. Cl. ............................ 514/372; 548/214; 544/3
[58] Field of Search .................. 514/372; 548/214

[56] References Cited

PUBLICATIONS

Helferich et al., Chemical Abstracts, vol. 69, enter 96118t (1968).
Konishiroku Ltd., Chemical Abstracts, vol. 98, entry 135175e (1983).

*Primary Examiner*—John M. Ford
*Attorney, Agent, or Firm*—Sughrue, Mion, Zinn Macpeak & Seas

[57] ABSTRACT

The phenylalkan(en)oic acids of the formula:

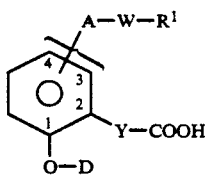

wherein
A is
i) —NHCO—,
ii) —O—
iii) —NHSO$_2$—,
iv) —CO—
v) —CH$_2$— or
vi) —CH(OH)—;
W is
i) C1-13 alkylene,
ii) phenylene or
iii)

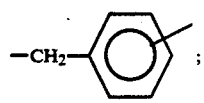

R$^1$ is i) hydrogen,
ii) C1-4 alkyl,
iii) —COOH,
iv) saturated or unsaturated, 4-7 membered monocyclic hetero ring containing one nitrogen as a hetero atom or saturated or unsaturated, 4-7 member mono-cyclic hetero ring containing one nitrogen as a hetero atom substituted by an oxo group,
v)

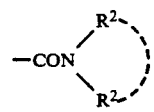

vi) —CH$_2$OH; or
A, taken together with W and R$^1$, is
i)

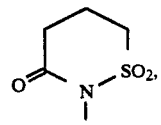

ii)

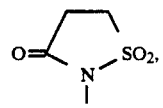

iii) —N—(SO$_2$R$^6$)$_2$,
iv)

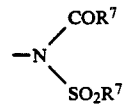

or
v)

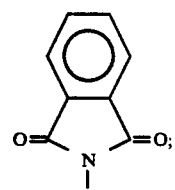

two R$^2$ are, same or different,
i) hydrogen,
ii) C1-4 alkyl or
iii) 4-7 membered saturated or unsaturated, monocyclic hetero ring containing two or three of nitrogen and sulfur in total, or two R$^2$, taken together with a nitrogen to which they are attached, form saturated or unsaturated,
i) 7-14 membered, bi- or tri-cyclic hetero ring containing one nitrogen as a hetero atom, or
ii) 4-7 mebered, mono-cyclic hetero ring containing two or three of nitrogen and oxygen in total;

Y is ethylene or vinylene;

D is
i) —Z—B or
ii)

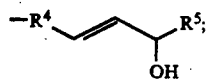

Z is C3-11 alkylene or alkenylene
R is

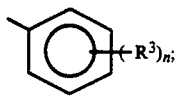

or
Z taken together with B, is C3-22 alkyl;
$R^3$ is
i) hydrogen,
ii) halogen,
iii) C1-8 alkyl, alkoxy or alkylthio, or
iv) C2-8 alkenyl, alkenyloxy or alkenylthio;
n is 1-3;

$R^4$ is C1-7 alkylene;
$R^5$ is
i) C1-12 alkyl,
ii) C2-12 alkenyl,
iii) C5-7 cycloalkyl or pp2 iv) phenethyl or phenethyl wherein the ring is substituted by one C1-4 alkoxy;

Two $R^6$ are, same or different,
i) C1-7 alkyl,
ii) benzyl or
iii) phenyl or phenyl wherein the ring is substituted by one C1-4 alkyl; and Two $R^7$ are, same or different, C1-4 alky; with the proviso that
i) —A—W—$R^1$ should bind to 3- or 4- carbon in benzene ring, and
ii) when W phenylene or

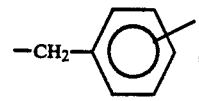

A should not represent —O—, —CO—, —CH$_2$— or —CH(OH)—; and non-toxic salts thereof, possess an antagonistic activity on leukotriene $B_4$, and therefore, are useful for the prevention and treatment of several diseases induced by leukotriene $B_4$.

4 Claims, No Drawings

PHENYLALKAN(EN)OIC ACID

DESCRIPTION

Summary

This invention is related to phenylalkan(en)oic acids which are useful for medicines.

More particularly, this invention is related to:
1) phenylalkan(en)oic acids of the formula:

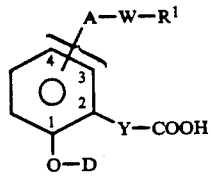

(wherein all of the symbols are the same meanings as hereinafter defined) and non-toxic salts thereof, 2) processes for the preparation of them and 3) antagonistic agents on leukotriene (abbreviated as LT hereinafter) B$_4$ containing them as active ingredient.

BACKGROUND

The metabolic routes, in which various compounds are biosynthesized from the same mother compound, i.e. arachidonic acid, are called "Arachidonate cascade" as a whole.

Arachidonic acid is metabolized by the action of lipoxygenase, e.g. 5-lipoxygenase, 12-lipoxygenase, and 15-lipoxygenase, to 5-hydroperoxyeicosatetraenoic acid (abbreviated as HPETE hereinafter), 12-HPETE and 15-HPETE, respectively.

These HPETEs are converted into 5-hydroxyeicosatetraenoic acid (abbreviated as HETE hereinafter), 12-HETE and 15-HETE, respectively, by the action of peroxidase which convert a hydroperoxy group to a hydroxy group. Furthermore, LTA$_4$ is also produced from 5-HPETE. LTA$_4$ is converted into LTB$_4$ and LTC$_4$. LTC$_4$ is converted into LTD$_4$ by the action of γ-glutamyl transpeptidase. Moreover, it has been defined that LTD$_4$ is metabolized to LTE$_4$ (see Biochem. Biophys. Res. Commun., 91, 1266 (1979) and Prostaglandins, 19 (5), 645 (1980)).

Moreover, the action of LTB$_4$ has been gradually identified recently. Namely, it as been identified that LTB$_4$ having the following structure:

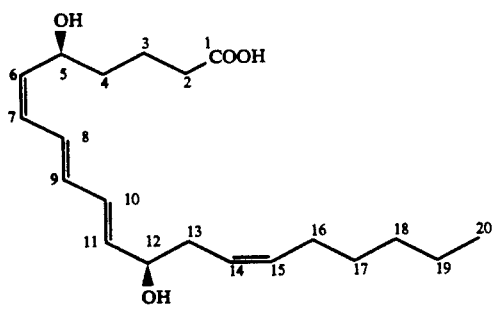

(wherein the double bonds between 6th- and 7th- carbon, 8th- and 9th-carbon, 10th- and 11th- carbon and 14th- and 15th-carbon, are Z, E, E and Z, respectively), possesses a powerful action of polymorphonuclear leukocytes (PMNLs) accumulation and PMNLs adhesion, and PMNLs degranulation (see Nature, 286, 264 (1980), Proc. Nat. Acad. Sci. U.S.A. 78, 3887 (1981) and J. Biol. Chem., 256, 5317 (1981)). Moreover it has been considered that LTB$_4$ promotes the release of arachidonic metabilites by attacking various cells as it has the powerful action like calcium ionophore (see J. Biol. Chem., 257, 4746 (1982)).

Moreover, LTB$_4$ in high concentration has been detected at the sites of various inflammation, for example, rheumatism, spinal arthritis (see Klichstein L. B., Shapleigh, C. and Goetzl, E. J. (1980) J. Clin. Invest., 66, 1166–1170), gout (Rae, S. A., Davidson, E. M. and Smith, M. J. H. (1982) Lancet II 1122–1123), psoriasis (see Grabbe, J., Czarnetzki, B. M., Rosenbach, T. and Mardin, M. (1984) J. Invest. Dermatol., 82, 477–479), ulceractive colitis (see Sharon, P. and Stenson, W. F. (1984) Gastroenterology 86, 453–460), respiratory disease (see O'Driscoll, B. R., Cromwell, O. and Kay, A. B. (1984) Clin. Exp., Immunol., 55, 397–404). The fact described above shows that LTB$_4$ is deeply related to various inflammation.

Accordingly, the antagonistic agents on LTB$_4$ are considered to be useful as anti-inflammatory agents and antiallergic agents.

RELATED ARTS

In recent research, some compounds having an antagonism on LTB$_4$ have been reported.

For example, 1) in the literatures (Feinmark, J., Lindgren, J. A., CLaesson, H. E., Malmsten, C., and Samuelsson, B. (1981) FEBS Lett., 136, 141–144; Showell, H. J., Oherness, I. G., Marfat, A., and Corey, E. J. (1982) Biochem. Biophy. Res. Commun., 106, 741–747), the compound of the formula:

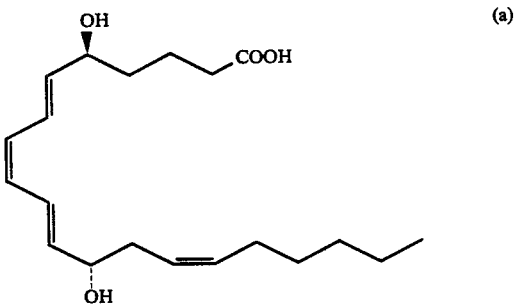

has been disclosed, 2) in the specification of Japanese Patent Kokai No. 59-33258, i.e. Derwent accession No. 84-173740/28, the compounds of the formula:

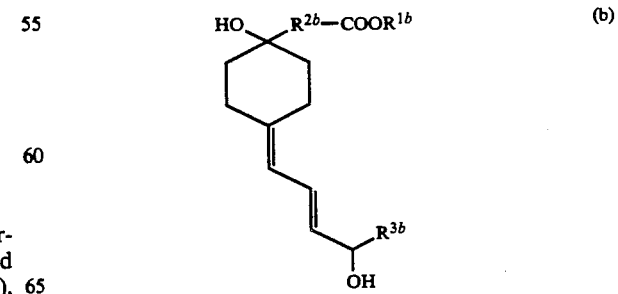

wherein $R^{1b}$ is hydrogen or C1-4 alkyl;

$R^{2b}$ is C1–8 alkylene; and $R^{3b}$ is hydrogen, C1–15 alkyl or the group of the formula —CH$_2$—A$_b$—R$^{4b}$ (wherein A$_b$ is cis-vinylene or ethynylene; and $R^{4b}$ is C1–13 alkyl); have been disclosed, 3) in the specification of Japanese Patent Kokai No. 59-95249, i.e. Derwent accession No. 84-84453/14, the compounds of the formula:

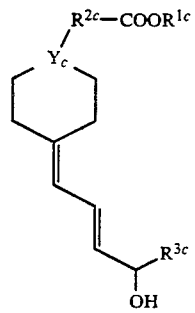

wherein Yc is nitrogen or aminomethyl; $R^{1c}$ is hydrogen or C1–4 alkyl; $R^{2c}$ is C1–8 alkylene; and $R^{3c}$ is C1–15 alkyl or the group of the formula: —CH$_2$—Ac—R$^{4c}$ (wherein Ac is cis-vinylene or ethynylene; and $R^{4c}$ is C1–12 alkyl); have been disclosed and more recently 4) in the specification of Japanese Patent Kokai No. 63-188644, i.e. European Patent Publication NO. 276065, the comnpounds of the formula:

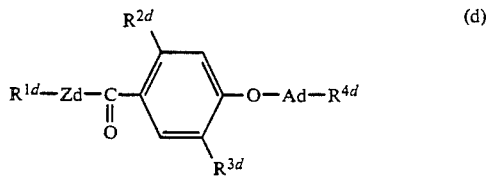

(wherein $R^{1d}$ hydrogen or —COOR$^{d'}$, Zd is —(CH$_2$)-nd— or phenylene (nd is 1–8); $R^{2d}$ is hydroxy, halogen or —O—(CH$_2$)md—Yd; $R^{3d}$ is C1–6 alkyl, C1–6 alkanoyl, C2–4 alkenyl, C1–4 alkoxy, C1–3 alkyl substituted by hydroxy or —CH$_2$—Dd; Ad is bond or straight-chain or branched-chain C1–10 alkylidene; $R^{4d}$ is C1–6 alkyl, C2–6 alkenyl or C2–6 alkynyl, hydroxy, —CN, halogen, —N$_3$, —NR$^{5d}$R$^{6d}$, —COR$^{7d}$, —S(O)pd—(C-1–4 alkyl), 1,2,4-triazol-1-yl, 5-tetrazolyl which may be substituted by C1–4 alkyl or —(CH$_2$)gdCOOR$^{d'}$, phenyl which may be substituted by 1 or 2 of halogen, —CN, C1–3 alkyl, —CF$_3$, —CH$_2$CN, —CH$_2$Br, C1–4 alkoxy, —S(O)pd—(C1–4 alkyl), acetenyl, acetyl, COOR$^{d'}$, 5-tetrazolyl, or 5-tetrazolyl substituted by C1–4 alkyl or —(CH$_2$)gd—COOR$^{d'}$ (each R$^{d'}$ is hydrogen or C1–4 alkyl; md is 1–4; gd is 1–4; Yd is hydrogen or —CN; Dd is halogen, C1–4 alkoxy or —S—(C1–4 alkyl)); $R^{5d}$ and $R^{6d}$ are independently hydrogen, C1–3 alkyl or C2–4 alkanoyl, or $R^{5d}$ and $R^{6d}$, taken together with a nitrogen atom to which they are attached, form morpholino; $R^{7d}$ is hydroxy, C1-alkoxy, halogen, —NR$^{5d}$R$^{6d}$, —NHOH, 5-tetrazolylamino or C1–3 alkyl; each pd is 0–2; with the proviso that when Ad is bond, $R^{4d}$ should be C1–6 alkyl or optionally substituted phenyl, and when one of $R^{5d}$ and $R^{6d}$ is C2–4 alkanoyl, then the other should be hydrogen; and the pharmaceutically acceptable salts have been disclosed, 5) in the specification of Japanese Patent Kokai No. 63-188646, i.e. European Patent Publication No. 276064, the compounds of the formula;

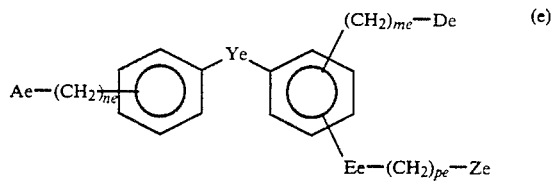

(wherein Ae and De are independently —CN, —COOR$^{1e}$ or 5-tetrazolyl; ne is 0 or 1; Ye is —O—, —CO—, —CH$_2$CO—, —C(=NOH)—, —CHOH—, —CH$_2$— or —C(=CH$_2$); me is 0–3; Ee is —O— or —CH$_2$—; pe is 0–16; Ze is hydrogen or —Ge—Qe; Ge is bond, —O—, —S(O)te—, —NH— or —CH=CH—, Qe is phenyl or phenyl substituted by 1 or 2 of halogen, C1–3 alkyl, C1–3 lakoxy, nitro, amino, trifluoromethyl, hydroxy and —S(O)pe —(C1–3 alkyl); pe and te are each 0–2; $R^{1e}$ is hydrogen or C1–3 alkyl); and the pharmaceutically acceptable salts have been disclosed.

DISCLOSURE OF THE INVENTION

The present inventionis related to 1) phenylalkan(en)oic acid of the formula:

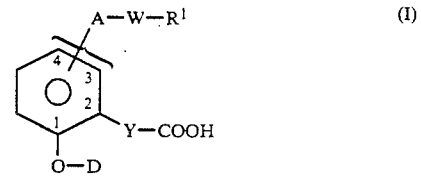

wherein

A is
i) —NHCO—,
ii) —O—
iii) —NHSO$_2$—,
iv) —CO—
v) —CH$_2$— or
vi) —CH(OH)—;

W is
i) C1–13 alkylene,
ii) phenylene or
iii)

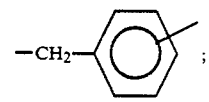

$R^1$ is
i) hydrogen,
ii) C1–4 alkyl,
iii) —COOH,
iv) saturated or unsaturated, 4–7 membered mono-cyclic hetero ring containing one nitrogen as a hetero atom or saturated or unsaturated, 4–7 membered mono-cyclic hetero ring containing one nitrogen as a hetero atom substituted by an oxo group,
v)

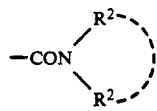

vi) —CH$_2$OH; or

A, taken together with W and R$^1$, is i)

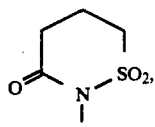

ii)

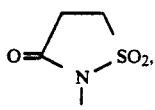

iii) —N—(SO$_2$R$^6$)$_2$, iv)

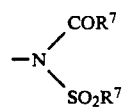

or v)

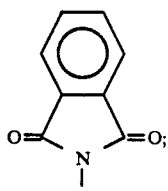

two R$^2$ are, same or different,
  i) hydrogen,
  ii) C1-4 alkyl or
  iii) 4–7 membered, saturated or unsaturated, mono-cyclic hetero ring containing two or three of nitrogen and sulfur in total, or two R$^2$, taken together with a nitrogen to which they are attached, form saturated or unsaturated,
  i) 7–14 membered, bi- or tri-cyclic hetero ring containing one nitrogen as a hetero atom, or
  ii) 4–7 membered, mono-cyclic hetero ring containing two or three of nitrogen and oxygen in total;
Y is ethylene or vinylene;
D is
  i) —Z—B or
  ii)

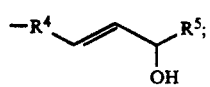

Z is C3-11 alkylene or alkenylene
B is

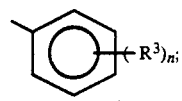

or
Z, taken together with B, is C3-22 alkyl;
R$^3$ is
  i) hydrogen,
  ii) halogen,
  iii) C1-8 alkyl, alkoxy or alkylthio, or
  iv) C2-8 alkenyl, alkenyloxy or alkenylthio;
n is 1-3;
R$^4$ is C1-7 alkylene;
R$^5$ is
  i) C1-12 alkyl,
  ii) C2-12 alkenyl,
  iii) C5-7 cycloalkyl or
  iv) phenethyl or phenethyl wherein the ring is substituted by one C1-4 alkoxy;
Two R$^6$ are, same or different,
  i) C1-7 alkyl,
  ii) benzyl or
  iii) phenyl or phenyl wherein the ring is substituted by one C1-4 alkyl; and
Two R$^7$ are, same or different, C1-4 alky;
with the proviso that
  i) —A—W—R$^1$ should bind to 3- or 4- carbon in benzene ring, and
  ii) when W is phenylene or

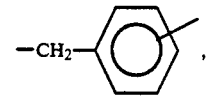

A should not represent —O—, —CO—, —CH$_2$— or —CH(OH)—; and non-toxic salts thereof, 2) processes for the preparation of them and 3) antagonistic agent on leukotriene B$_4$ containing them as active ingredient.

The present invention includes all isomers unless otherwise specified. For example, alkyl, alkoxy, alkenyl, alkenyloxy, alkylthio, alkenylthio, alkylene and alkenylene groups mean straight-chain or branched-chain alkyl, alkoxy, alkenyl, alkenyloxy, alkylthio, alkenylthio, alkylene and alkenylene groups, respectively, and the double-bond in alkenylene, alkenyl, alkenyloxy and alkenylthio groups include E, Z and the mixture of E and Z. In case of existing branched-chain alkyl group etc., the present invention includes the isomers caused by existing asymmetrical carbon atoms.

In the formula (I), C1-13 alkylene group shown by W are methylene, ethylene, trimethylene, tetramethylene, pentamethylene, hexamethylene, heptamethylene, octamethylene, nonamethylene, decamethylene, undecamethylene, dodecamethylene, tridecamethylene group and isomers thereof.

In the formula (I), C1-4 alkyl group shown by R$^1$, R$^2$, substituent in R$^6$, and R$^7$ are methyl, ethyl, propyl, butyl group and isomers thereof.

In the formula (I), 4–7 membered, saturated or unsaturated, mono-cyclic hetero ring containing one nitrogen as a hetero atom, shown by R¹ are, for example, pyrrole, pyridine ring and partially or fully saturated rings thereof, such as pyrrolidine. These rings may be substituted by one oxo group. 4-7 membered, saturated or unsaturated, mono-cyclic hetero ring containing two or three of nitrogen and sulfur in total, shown by R² are, for example, thiazole, isothiazole, thiadiazoline ring and partially or fully saturated rings thereof.

In the formula (I), saturated or unsaturated, 7-14 membered, bi- or tri-cyclic hetero ring containing one nitrogen as a hetero atom, shown by two R², taken together with a nitrogen to which they are attached are, for example, indole, isoindole, quinoline, isoquinoline, carbazole, acridine ring and partially or fully saturated rings thereof. Saturated or unsaturated, 4-7 membered, mono-cyclic hetero ring containing two or three of nitrogen and oxygen in total, shown by two R², taken together with a nitrogen are, for example, oxazole, issoxazole, furazan ring and partially or fully saturated rings thereof and morpholine ring.

In the formula (I) C3-11 alkylene and alkenylene groups shown by Z are trimethylene, tetramethylene, pentamethylene, hexamethylene, heptamethylene, octamethylene, nonamethylene, decamethylene, undecamethylene group and isomers thereof and the groups containing 1 to 3 of double bonds therein.

In the formula (I), c1-8 alkyl group shown by R³ are methyl, ethyl, propyl, butyl, pentyl, hexyl, heptyl, octyl group and isomers thereof. C1-8 alkoxy group shown by R³ are methoxy, ethoxy, propoxy, butoxy, pentyloxy, hexyloxy, heptyloxy, octyloxy group and isomers thereof. C1-8 alkylthio group shown by R³ are methylthio, ethylthio, propylthio, butylthio, pentylthio, hexylthio, heptylthio, octylthio group and isomers thereof.

In the formula (I), C2-8 alkenyl group shown by R³ are the groups containing 1 to 3 of double bonds in ethyl, propyl, butyl, pentyl, hexyl, heptyl, octyl group and isomers thereof. C2-C8 alkenyloxy group shown by R³ are the groups containing 1 to 3 of double bonds in ethoxy, propoxy, butoxy, pentyloxy, hexyloxy, heptyloxy, octyloxy group and isomers thereof. C2-C8 alkenylthio group shown by R³ are the groups 1 to 3 of double bonds in ethylthio, propylthio, butylthio, pentylthio, hexylthio, heptylthio, octylthio group and isomers thereof. Halogen shown by R³ are, fluorine, chlorine, bromine and iodine atom.

In the formula (I), C3-22 alkyl group shown by Z, taken together with B are propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl group and isomers thereof.

In the formula (I) C1-7 alkylene group shown by R⁴ are methylene, ethylene, trimethylene, tetramethylene, pentamethylene, hexamethylene, heptamethylene group and isomers thereof.

In the formula (I), C1-12 alkyl group shown by R⁵ are methyl, ethyl, propyl, butyl, pentyl, hexyl, heptyl, octyl, nonyl, decyl, undecyl, dodecyl group and isomers thereof. C2-12 alkenyl group shown by R⁵ are the groups containing 1 to 3 of double bonds in ethyl, propyl, butyl, pentyl, hexyl, heptyl, octyl, nonyl, decyl, undecyl, dodecyl group and isomers thereof. C5-7 cycloalkyl group shown by R⁵ are cyclopentane, cyclohexane, cycloheptane. C1-4 alkoxy group shown by substituents in R⁵ are methoxy, ethoxy, propoxy, butoxy group and isomers thereof.

In the formula (I), C1-7 alkyl group shown by R⁶ are methyl, ethyl, propyl, butyl, pentyl, hexyl, heptyl group and isomers thereof.

COMPARISON WITH RELATED ARTS

The compounds of the formula (I), of the present invention are quite novel.

More concretely, the compounds wherein W represents an alkylene, of the present invention are quite novel in structure. Furthermore, it can not be expected from the information of the related arts that the compounds having these structures, possess an antagonism on leukotriene B₄.

The compounds wherein W represents a phenylene or the group of the formula:

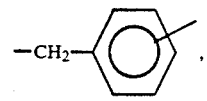

of the present invention are also quite novel. The compounds of the formula (d) have the structure in which the group corresponding to A in the formula (I) is carbonyl group, and those of the formula (e) have the structure in which the group corresponding to A in the formula (I) is oxy, carbonyl, methylene or hydroxymethylene group. On the other hand, the compounds wherein W represents a phenylene or the group of the formula:

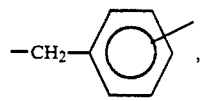

of the present invention, have the group of the formula: —NHCO— or —NHSO₂— as the group A. Therefore, the compounds of the present invention are quite different from the related arts in structure in that the groups shown by A represent quite different groups.

Furthermore, it can not be expected that an antagonism on leukotriene B₄ was held in the compounds wherein oxy, carbonyl, methylene or hydroxymethylene group is replaced by the groups of the formula —NHCO— or —NHSO₂—.

SALTS

The compounds of the formula (I) may be converted into the corresponding salts by the known method. Non-toxic and water-soluble salts are preferable. Suitable salts, for example, are followings: salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

PROCESS FOR THE PREPARATION OF THE COMPOUNDS OF THE PRESENT INVENTION

The compounds of the formula (I), of the present invention may be prepared by
1) saponificating the compound of the formula:

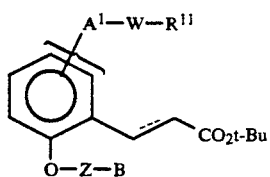 (II)

wherein
A¹ is
i) —NHCO— or
ii) —NHSO₂—;
R¹¹ is
i) the group of R^{1a} (wherein R^{1a} is hydrogen, saturated or unsaturated, 4–7 membered monocyclic hetero ring containing one nitrogen as a hetero atom, unsubstituted or substituted by an oxo group or C1–C4 alkyl),
ii) —CO₂H or
iii) the group shown by:

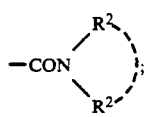

or
A¹, taken together with W and R¹¹, is
i)

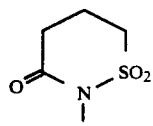

ii)

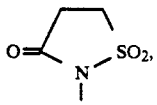

iii)

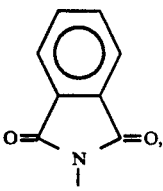

iv)

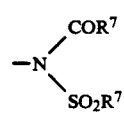

or
v) —N—(SO₂R⁶)₂;

is ethylene or vinylene;
t-Bu is tert-Butyl group; and
the other symbols are the same meanings as described hereinbefore;
or the compounds of the formula:

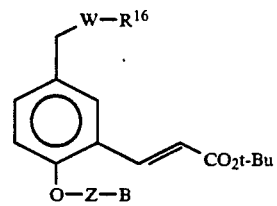 (XI)

wherein
R¹⁶ is
i) —CO₂H or
ii) the group of the formula:

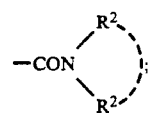

and
the other symbols are the same meanings as described hereinbefore;
with using an acid (formic acid, trifluoroacetic acid etc.) in an inert organic solvent (methanol, tetrahydrofuran etc.), 2) saponificating the compound of the formula:

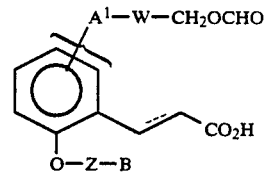 (III)

wherein, all of the symbols are same meaning as described hereinbefore;
the compound of the formula:

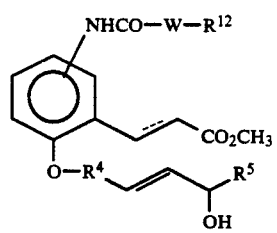 (IV)

wherein
R¹² is
i) the group of R^{1a},
ii) the group shown by

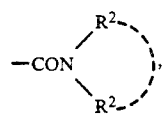

iii) —CO₂CH₃ or

IV)

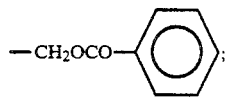

and the other symbols are the same meanings as described hereinbefore;

the compound of the formula:

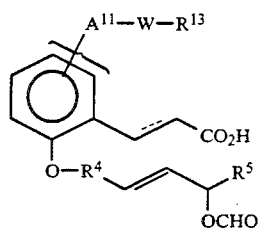

(V)

wherein

A¹¹ is —NHSO₂—;

R¹³ is i) the group of —R¹ᵃ, ii) the group shown by

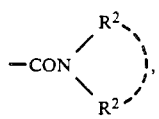

iii) —CH₂OCHO or iv) —CO₂H; or

A¹¹, taken together with W and R¹³, is i)

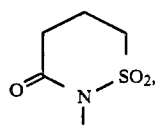

ii)

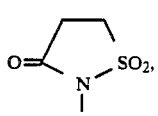

iii)

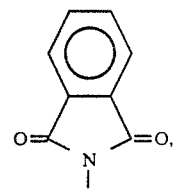

iv)

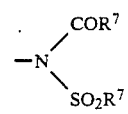

or v) —N—(SO₂R⁶)₂; and the other symbols are the same meanings as described hereinbefore;

the compound of the formula:

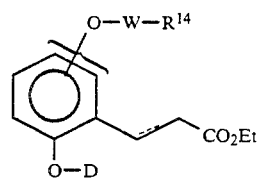

(VI)

wherein

Et is ethyl;

R¹⁴ is i) the group of —R¹ᵃ, ii) the group shown by

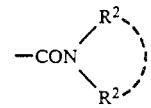

or iii) —CO₂Et; and the other symbols are the same meanings as described hereinbefore;

the compound of the formula:

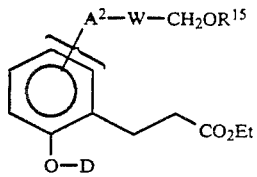

(VII)

wherein

A² is i) —O— or ii) —CH₂—;

R¹⁵ is i) hydrogen or ii) acetyl group; and the other symbols are the same meanings as described hereinbefore;

the compound of the formula:

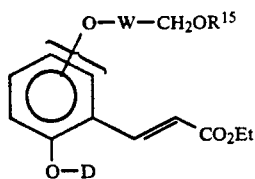
(VIII)

wherein all of the symbols are the same meanings as described hereinbefore;
the compound of the formula:

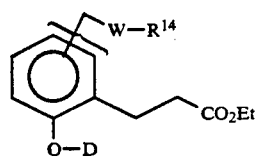
(IX)

wherein all of the symbols are the same meanings as described hereinbefore;
the compound of the formula:

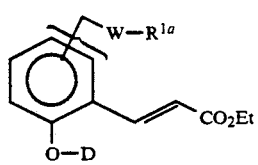
(X)

wherein all of the symbols are the same meanings as described hereinbefore;
the compound of the formula;

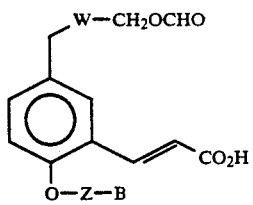
(XII)

wherein all of the symbols are the same meanings as described hereinbefore;
the compound of the formula:

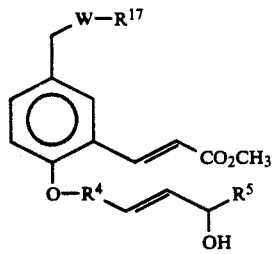
(XIII)

wherein
R$^{17}$ is
i) the group shown by

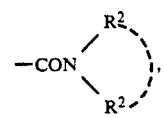

ii) —CH$_2$OH or
iii) —CO$_2$H; and
the other symbols are the same meanings as described hereinbefore;
the compound of the formula:

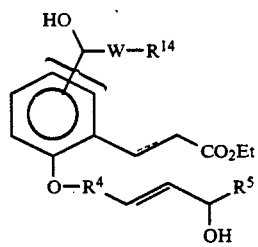
(XV)

wherein all of the symbols are the same meanings as described hereinbefore;
the compound of the formula:

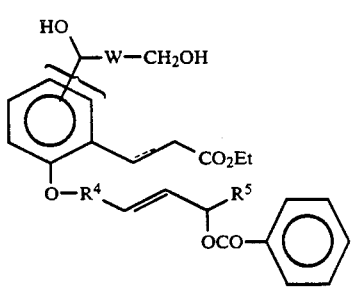
(XVI)

wherein all of the symbols are the same meanings as described hereinbefore;
the compound of the formula:

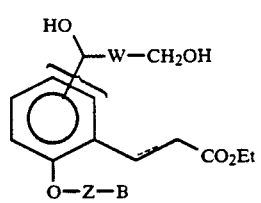
(XVII)

wherein all of the symbols are the same meanings as described hereinbefore;
the compound of the formula:

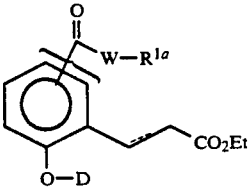
(XVIII)

wherein all of the symbols are the same meanings as described hereinbefore;
the compound of the formula:

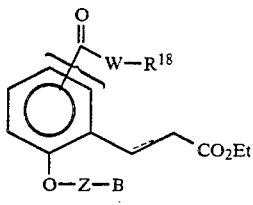

wherein
R[18] is
  i) —CO$_2$Et,
  ii) the group shown by

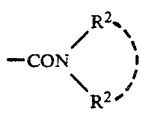

or
  iii) —CH$_2$OH; and
the other symbols are the same meanings as described hereinbefore;
the compound of the formula:

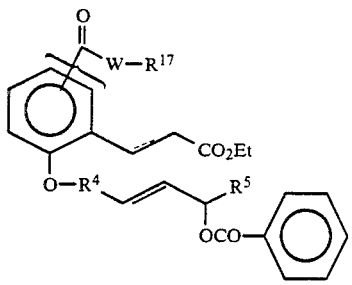 (XX)

wherein, all of the symbols are the same meanings as described hereinbefore;
the compound of the formula:

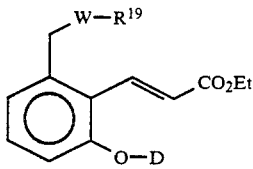 (XXI)

wherein
R[19] is
  i) the group shown by $$-CON\diagup_{R^2}^{R^2}$$

or
  ii) —CO$_2$Et; and
the other symbols are the same meanings as described hereinbefore; or
the compound of the formula:

(XXII)

wherein all of the symbols are the same meanings as described hereinbefore; with using an alkali (sodium hydroxide etc.) in an inert organic solvent (methanol, tetrahydrofuran etc.) or
3) reducing the compound of the formula:

(XIV)

wherein all of the symbols are the same meanings as described hereinbefore; with using reducing agent (sodium borohydride etc.) in an inert organic solvent (methanol etc.).

PROCESS FOR THE PREPARATION OF THE INTERMEDIATES

The compounds of the formulae (II), (III), (IV), (V), (VI), (VII), (VIII), (IX), (X), (XI), (XII), (XIII), (XIV), (XV), (XVI), (XVII), (XVIII), (XIX), (XX), (XXI) and (XXII) may be prepared by the steps shown in the following scheme [A], [B], [C], [D] and [E].

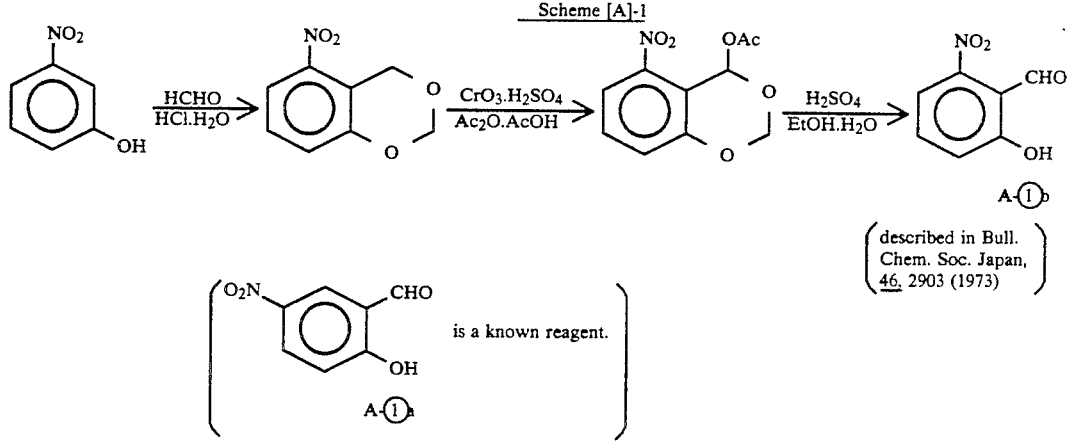

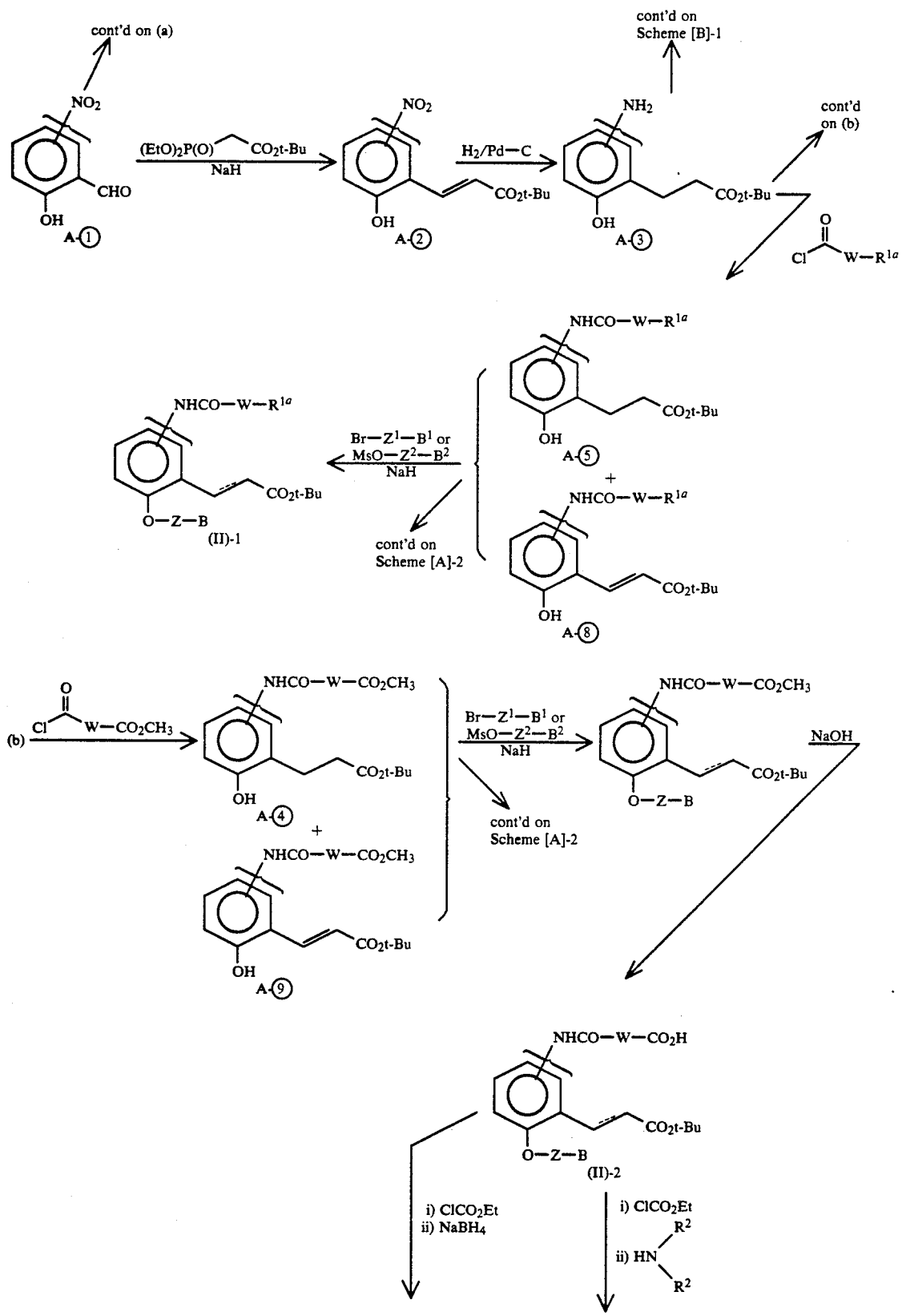
Scheme [A]-1

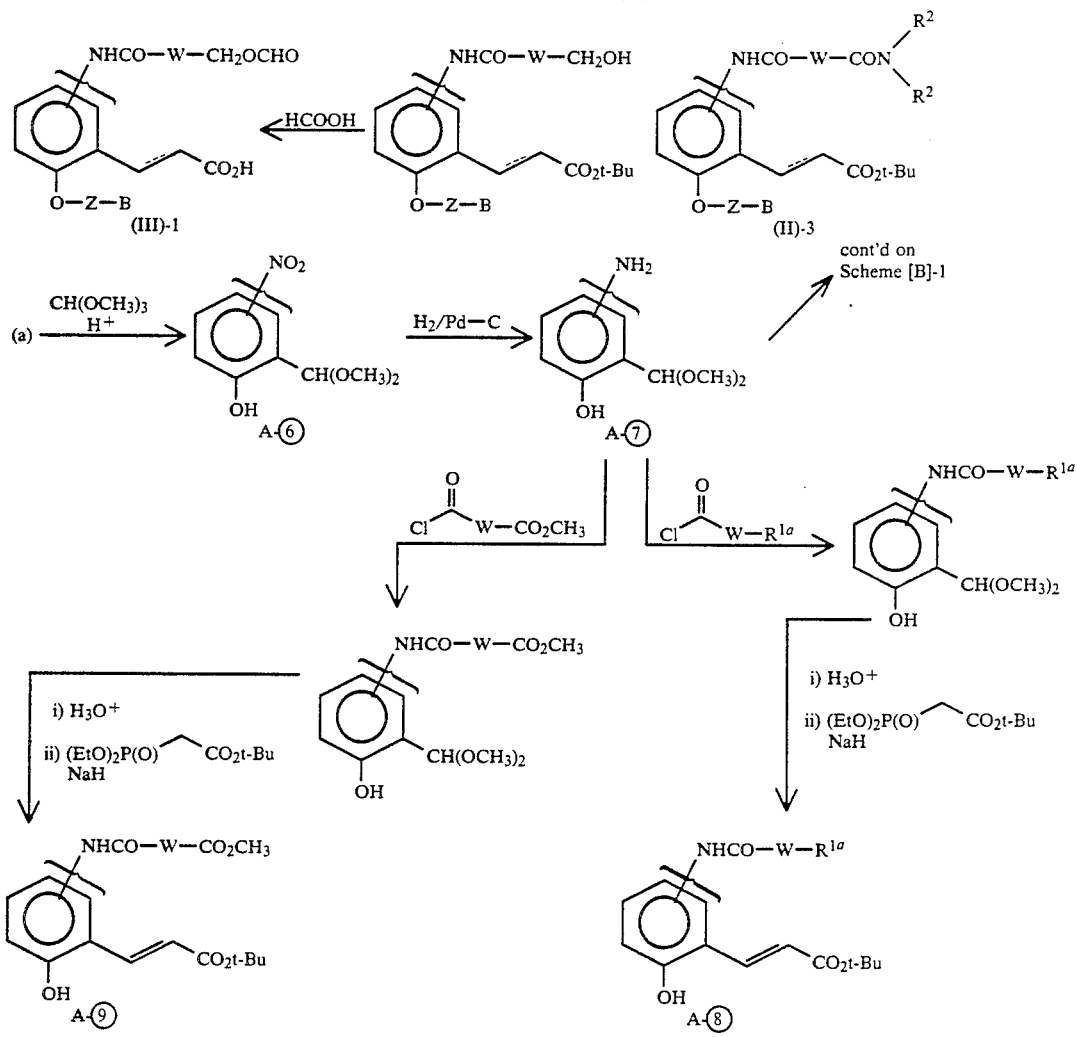

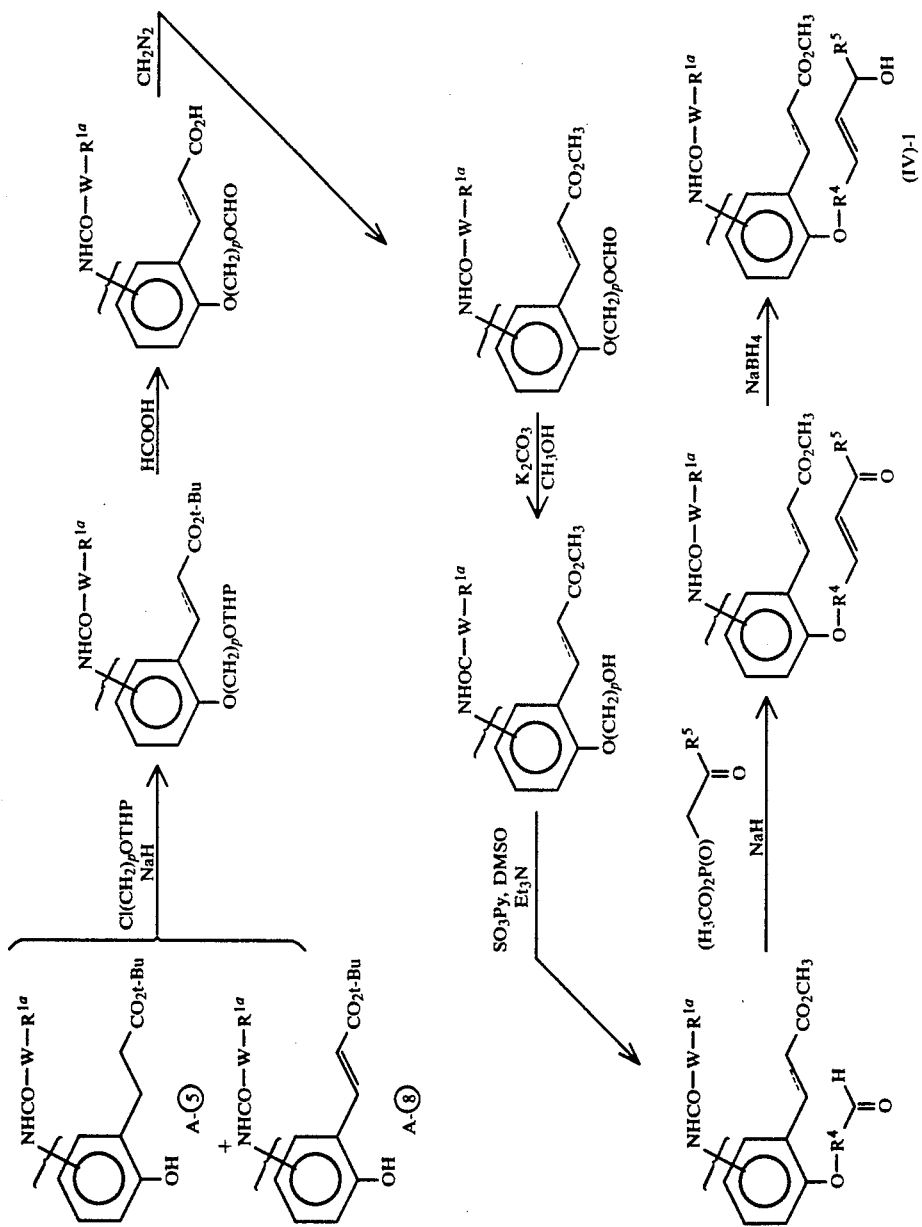

-continued
Scheme [A]-2
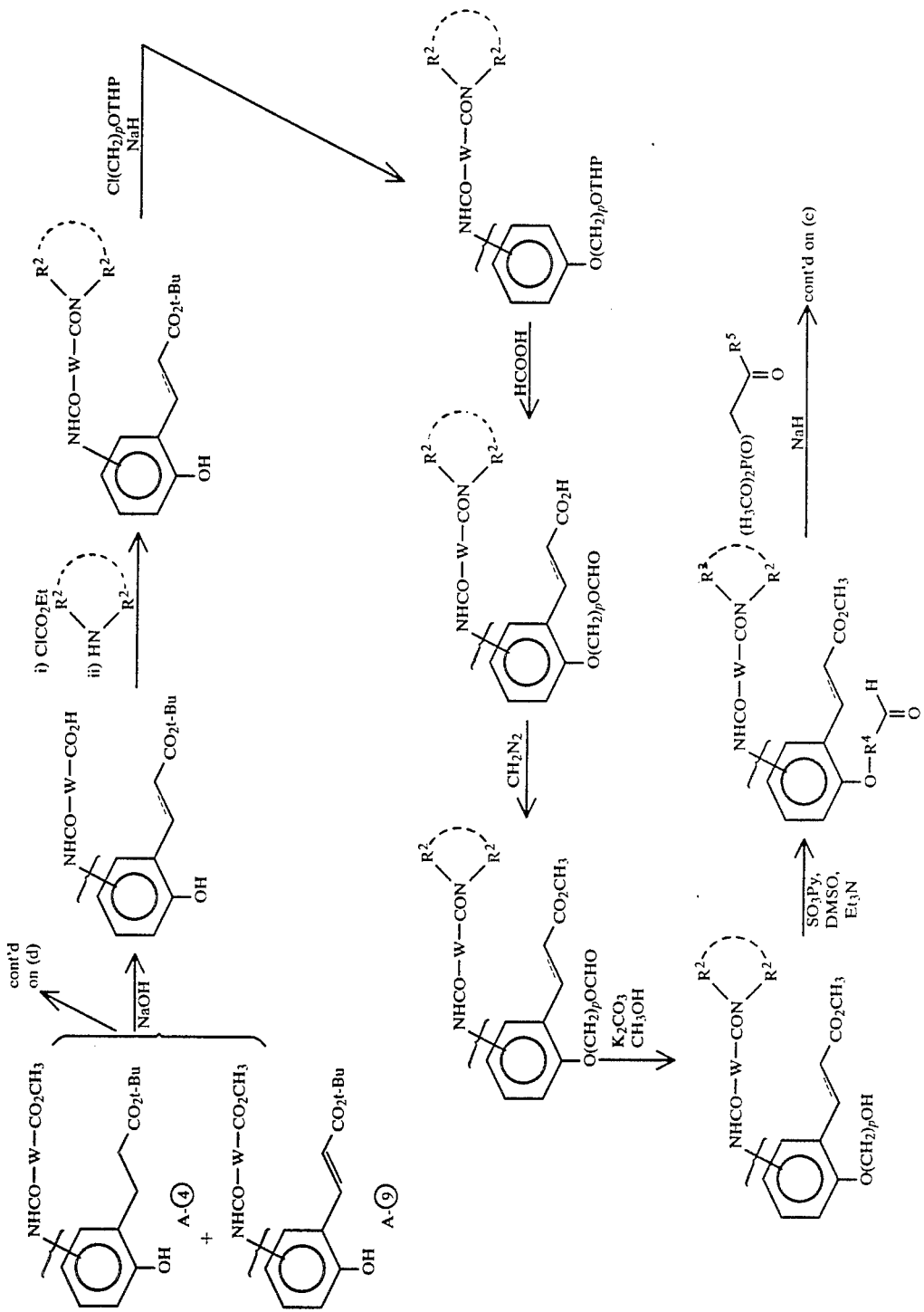

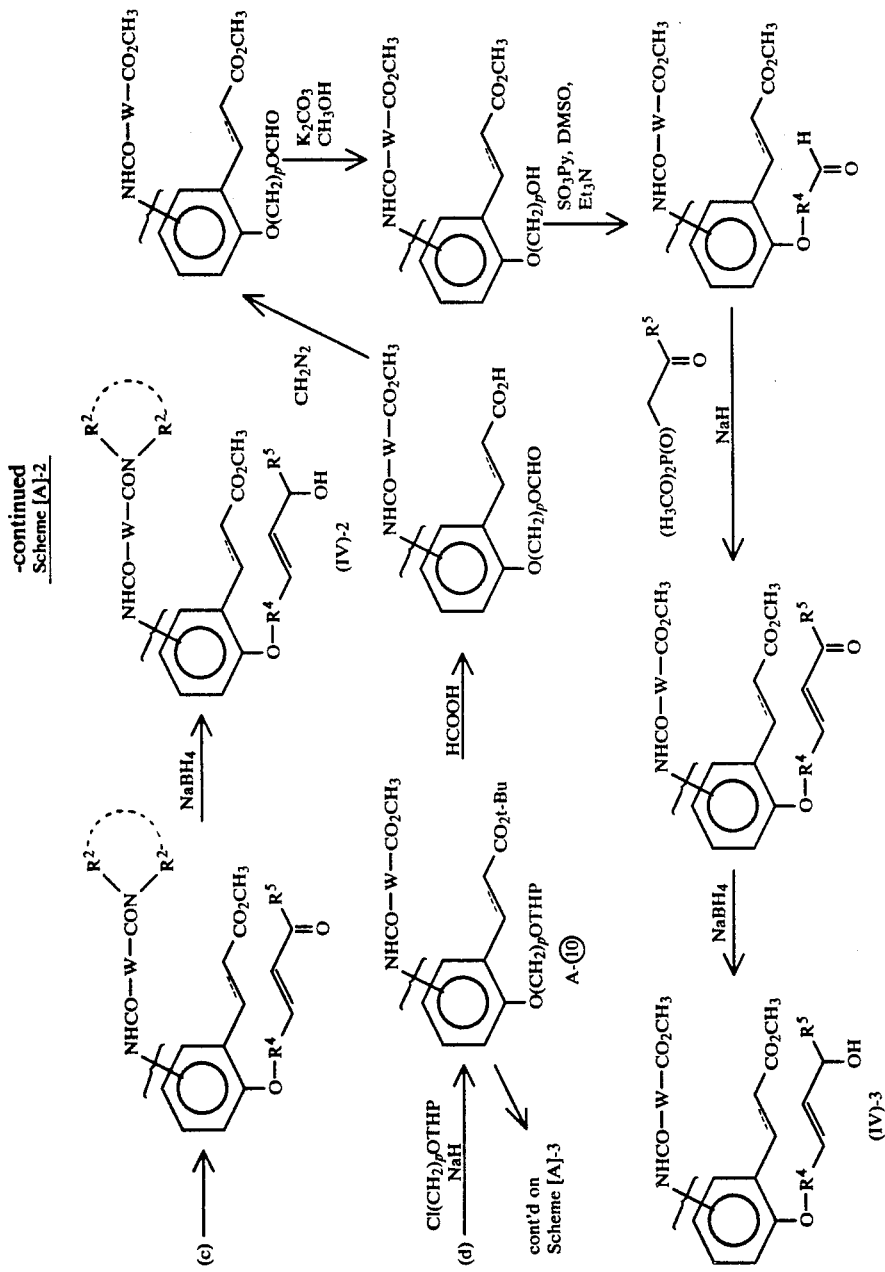

Scheme [A]-3
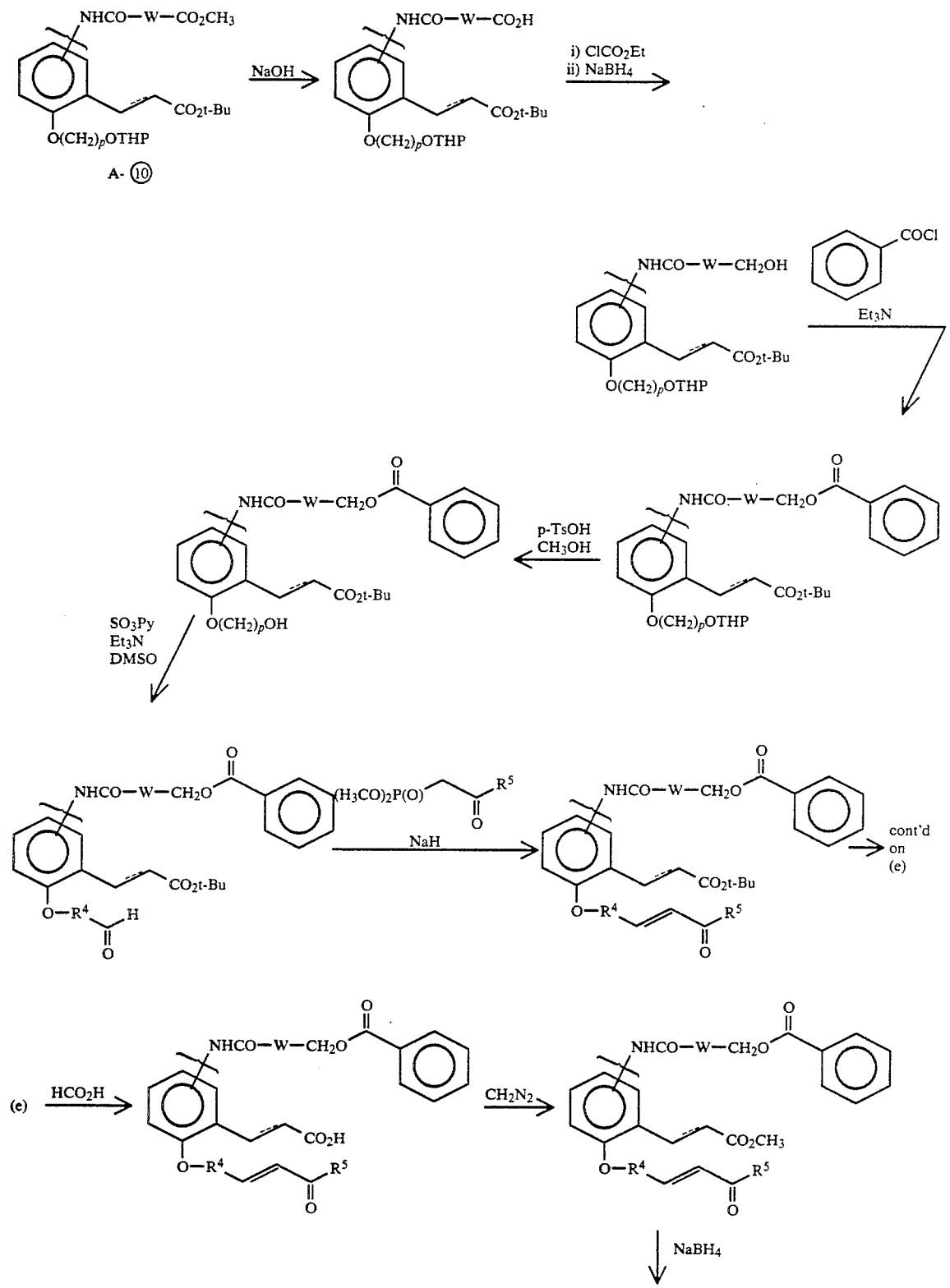

-continued
Scheme [A]-3
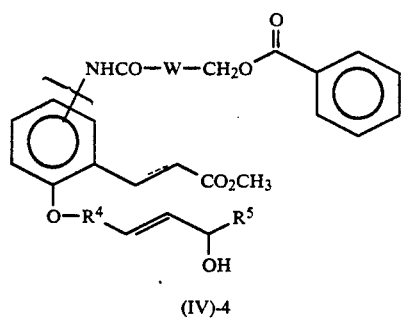
Scheme [B]-1
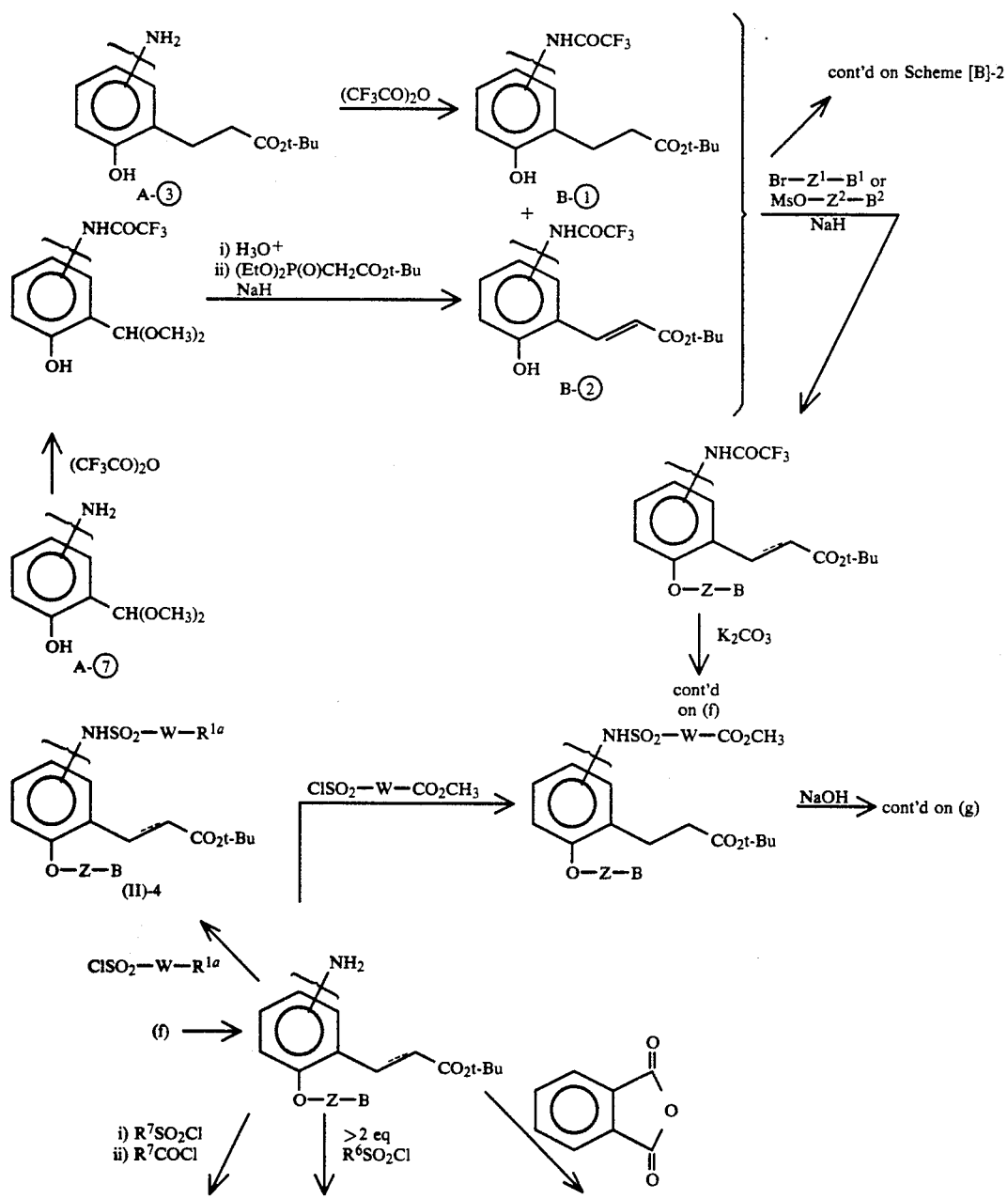

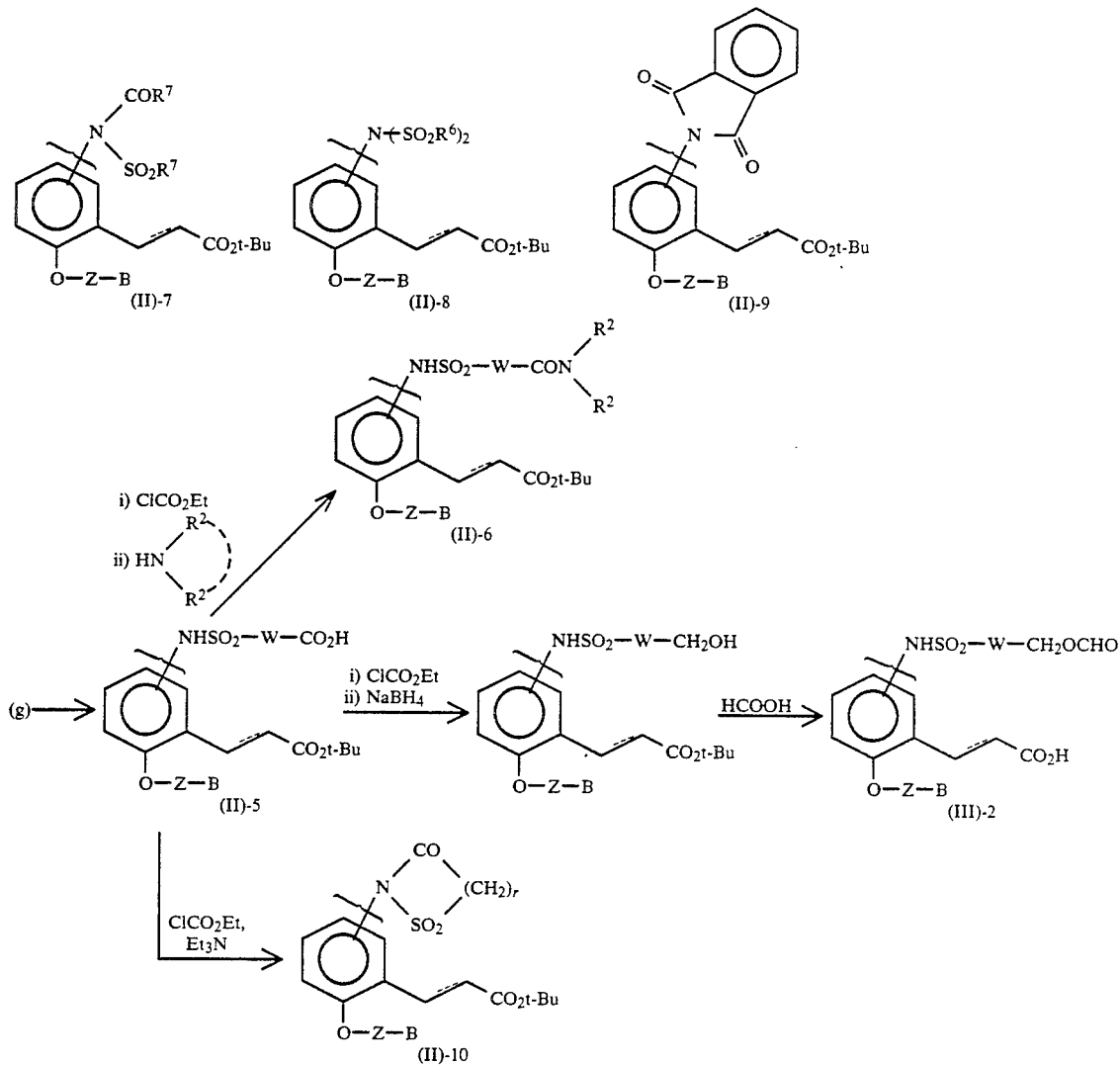

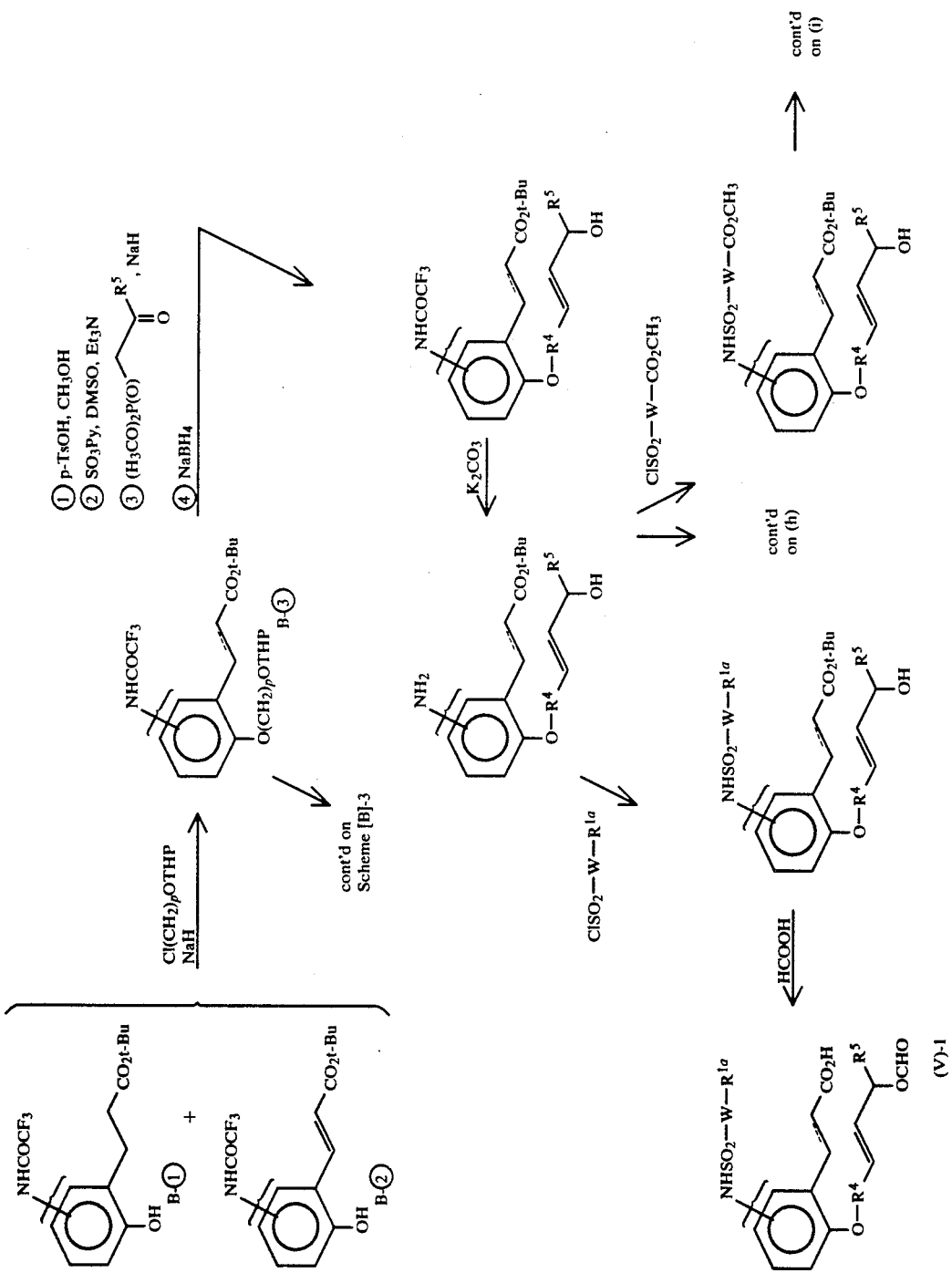

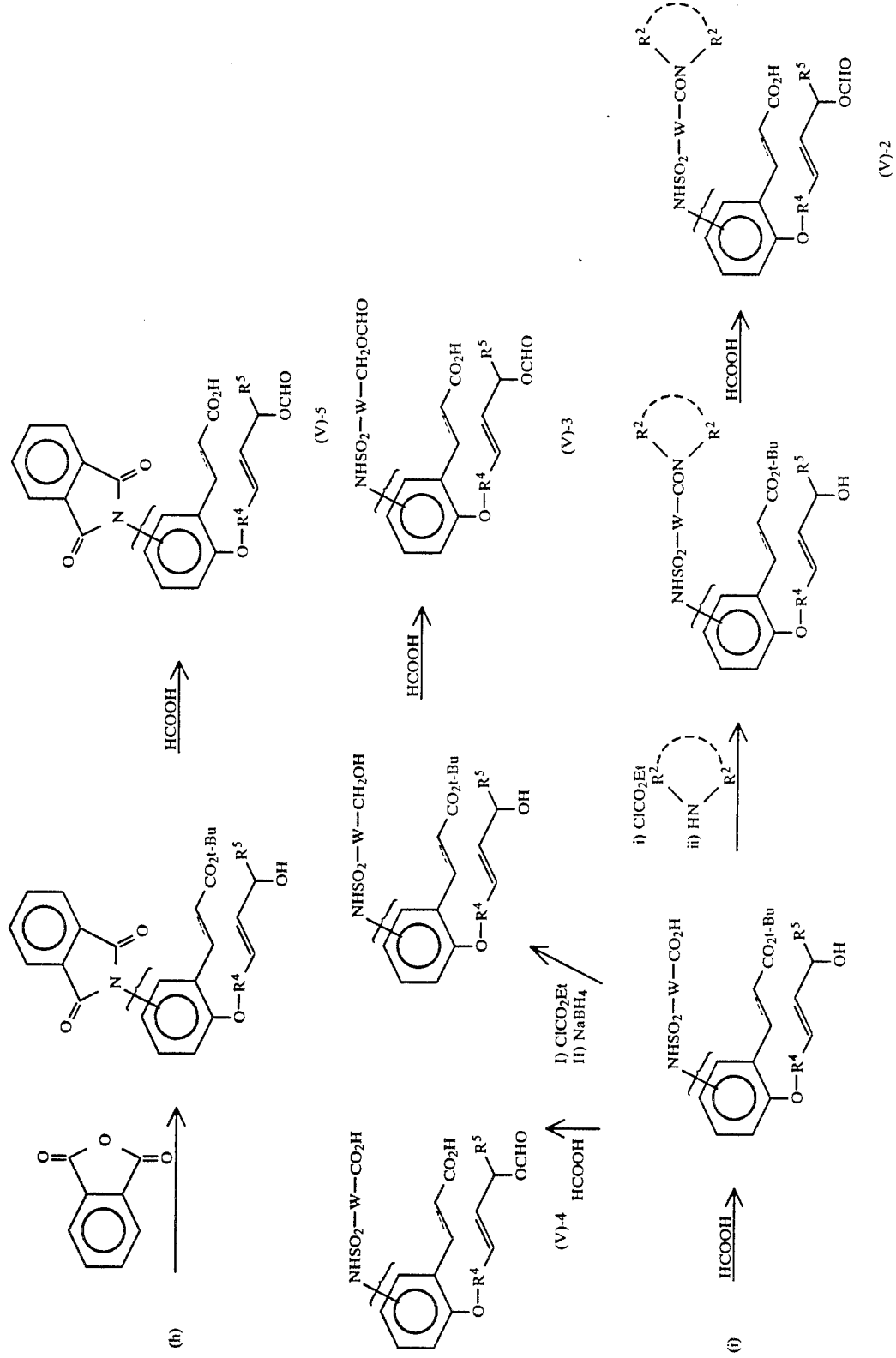

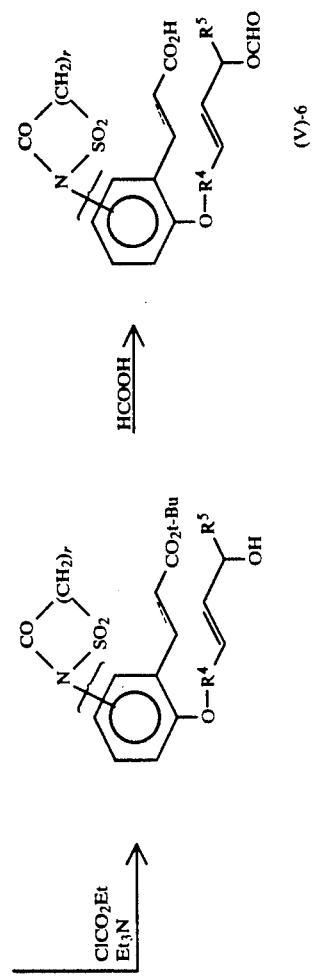

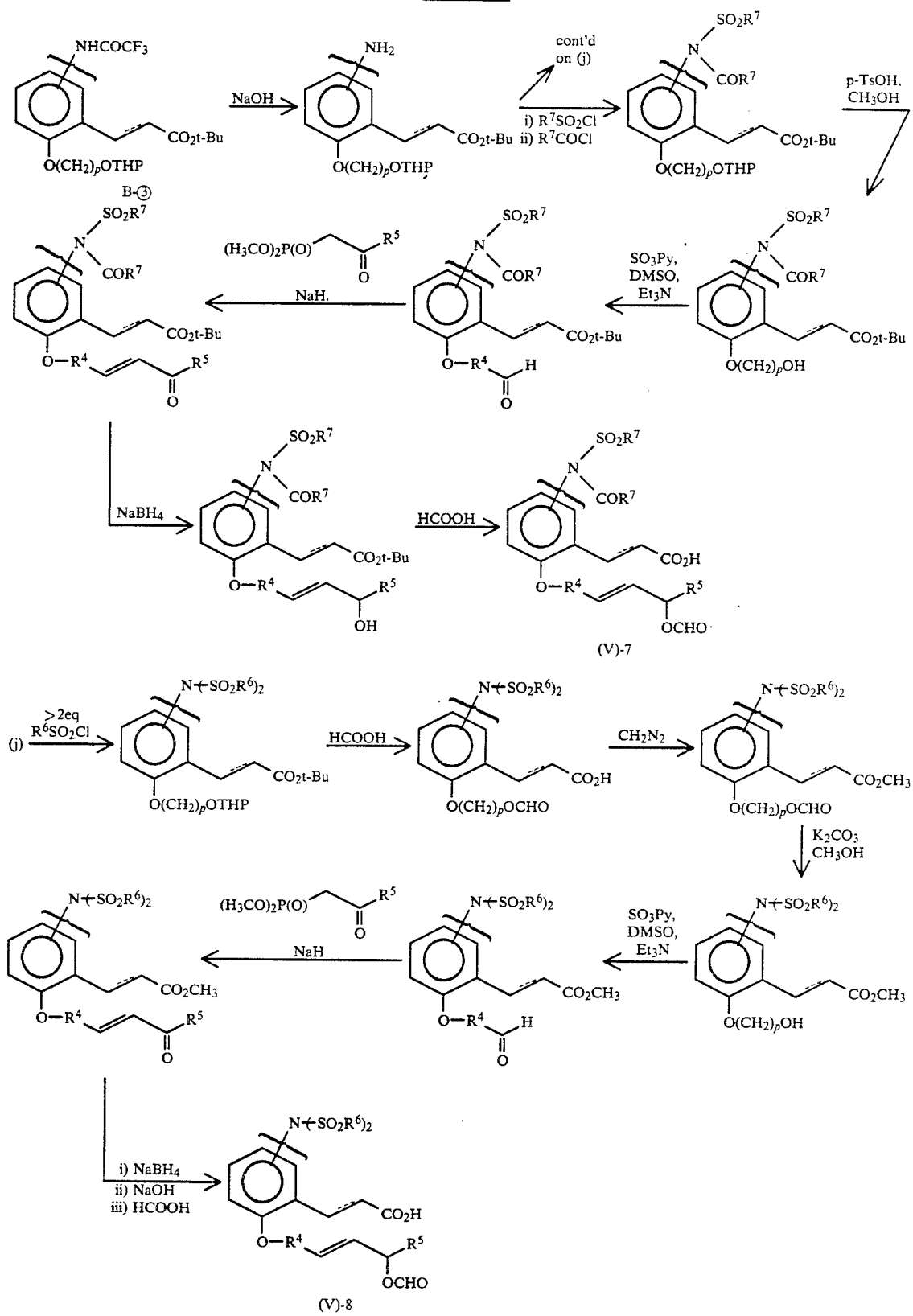
Scheme [B]-3

Scheme [C]-1a
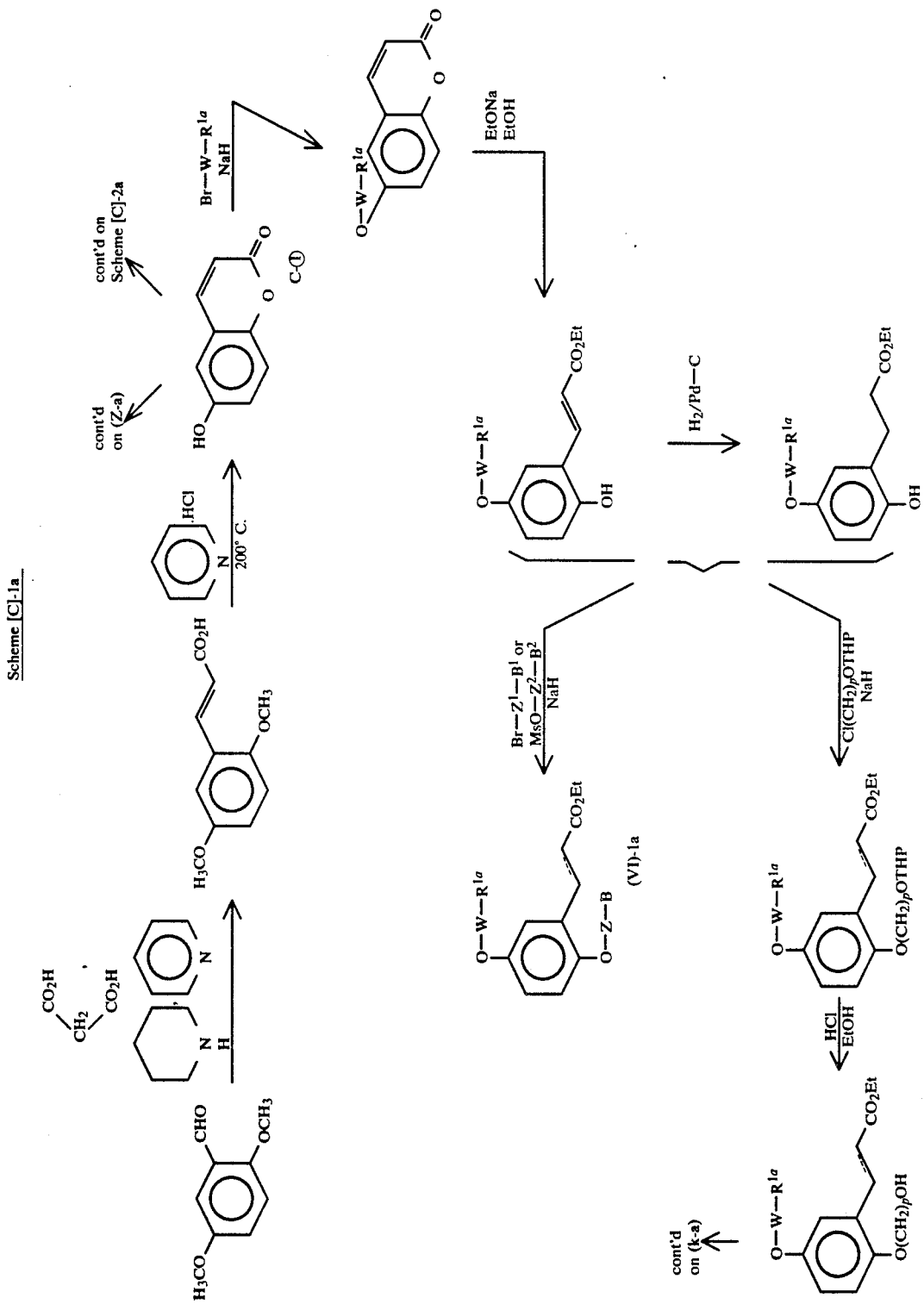

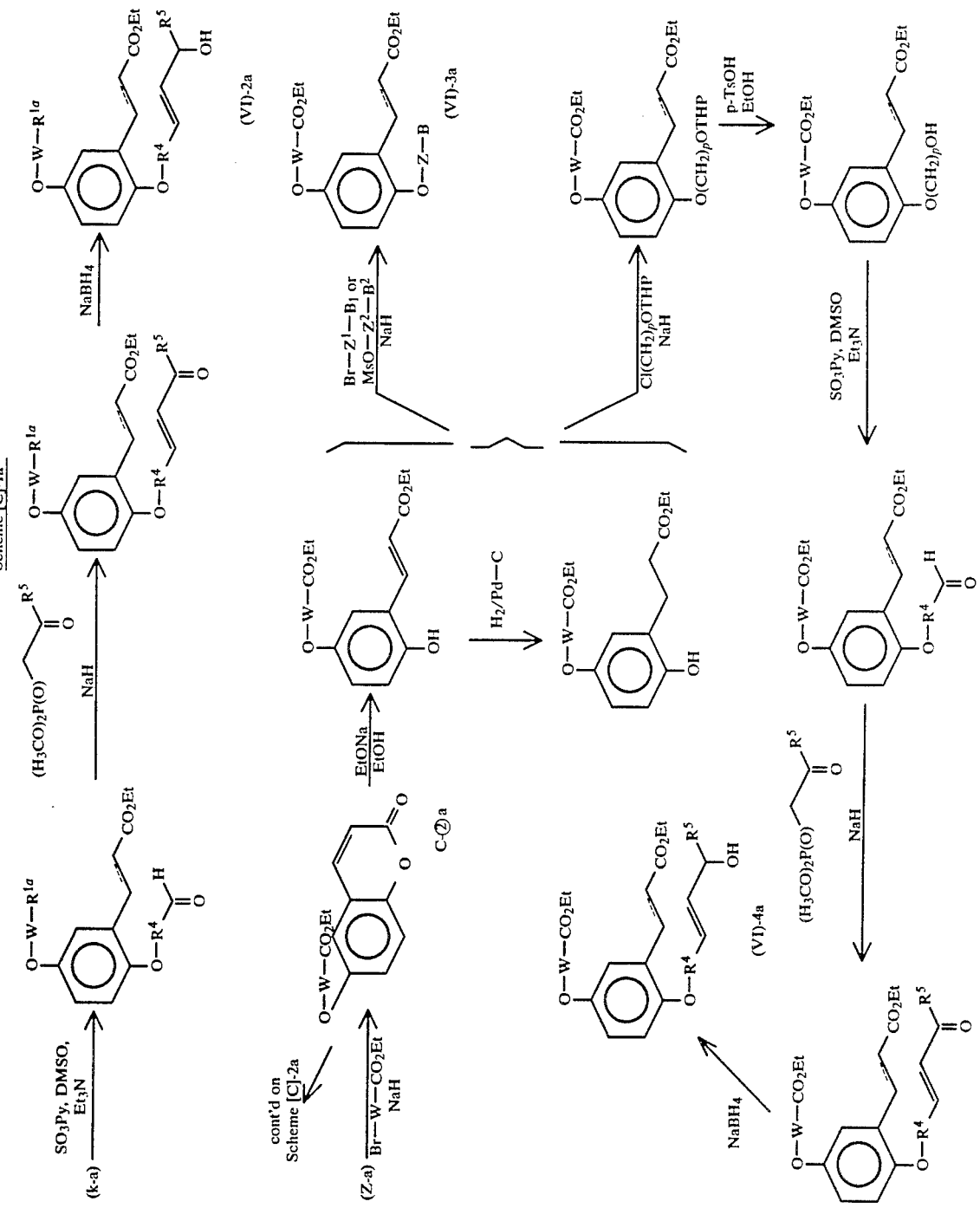

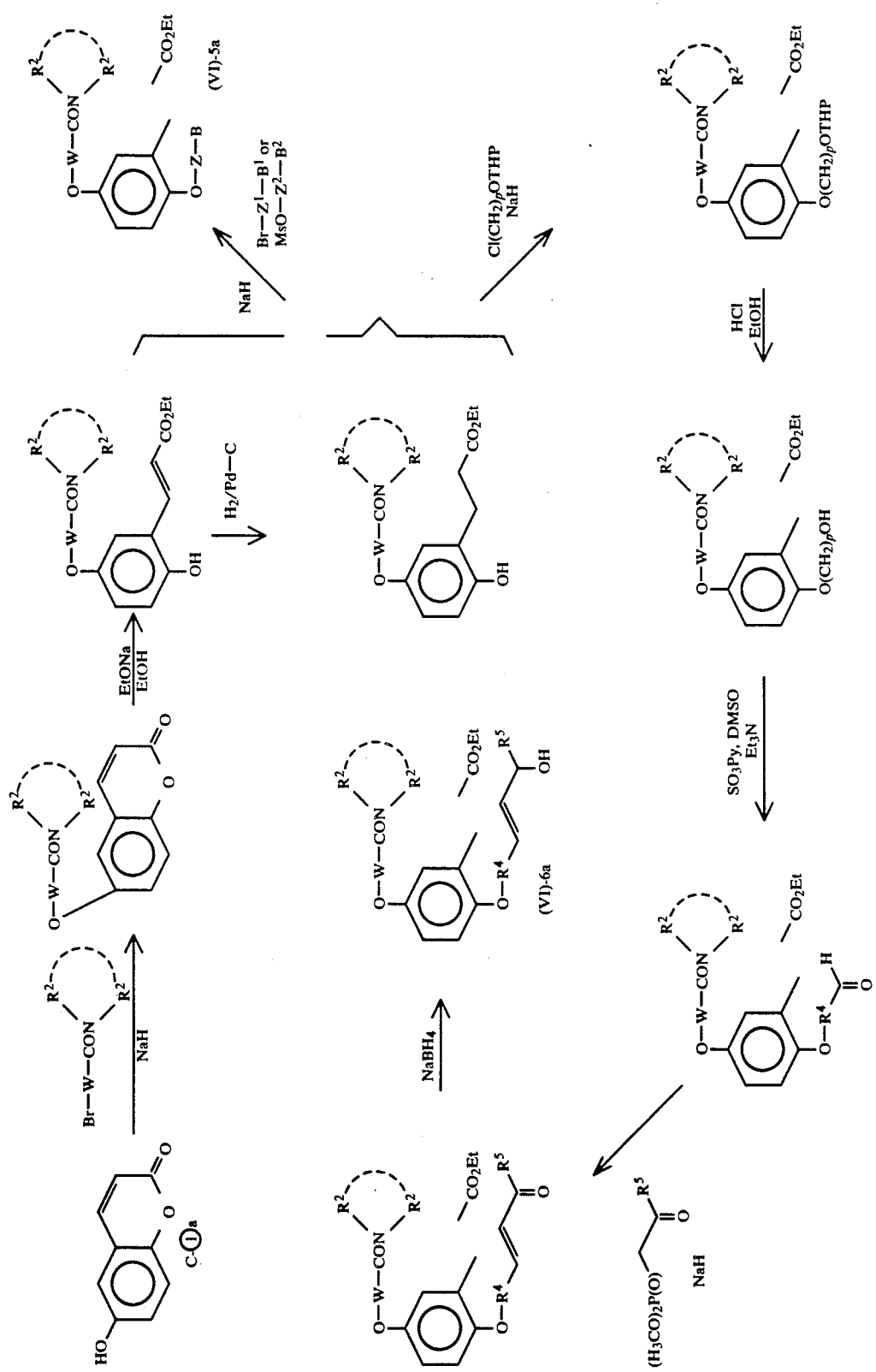

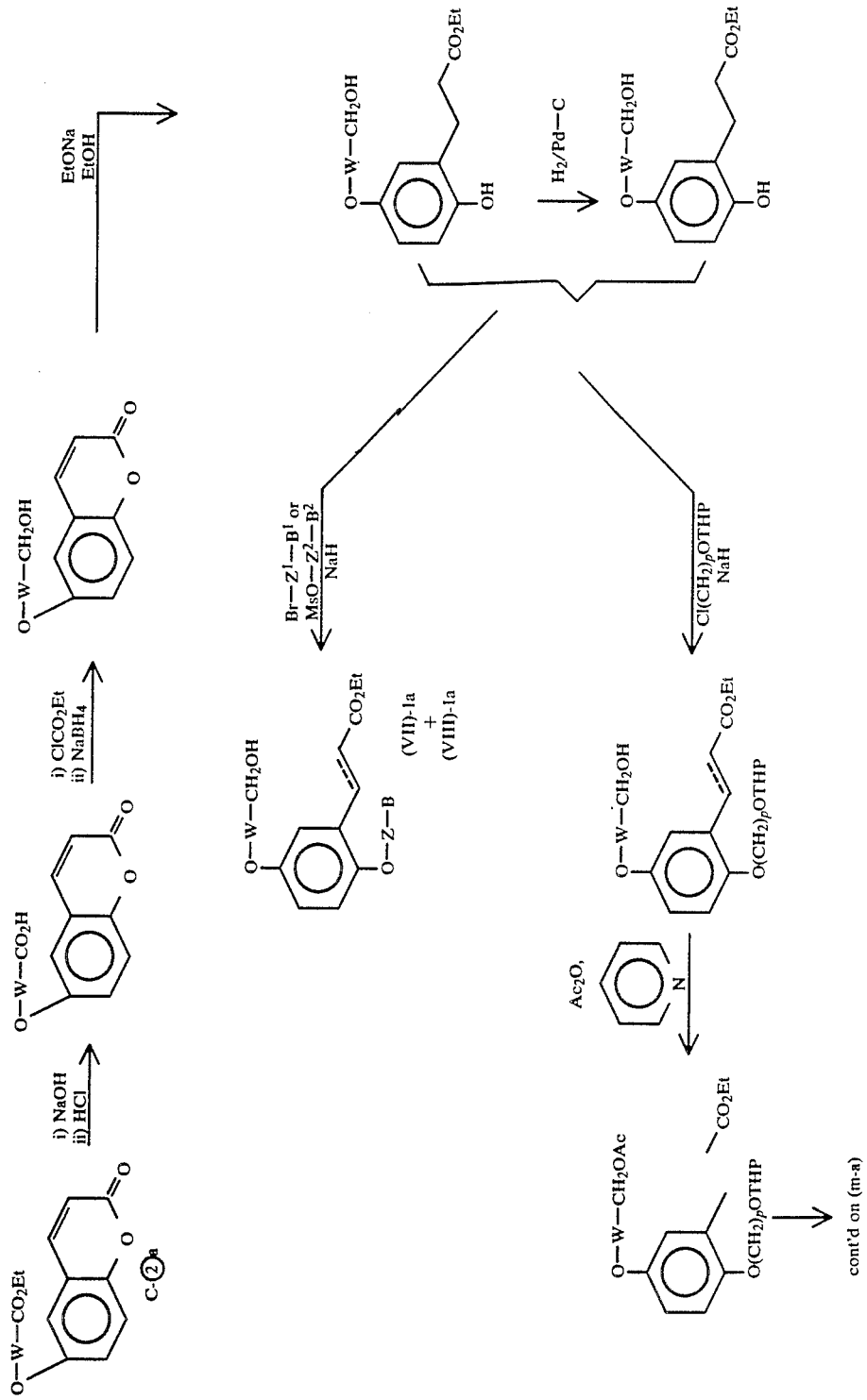

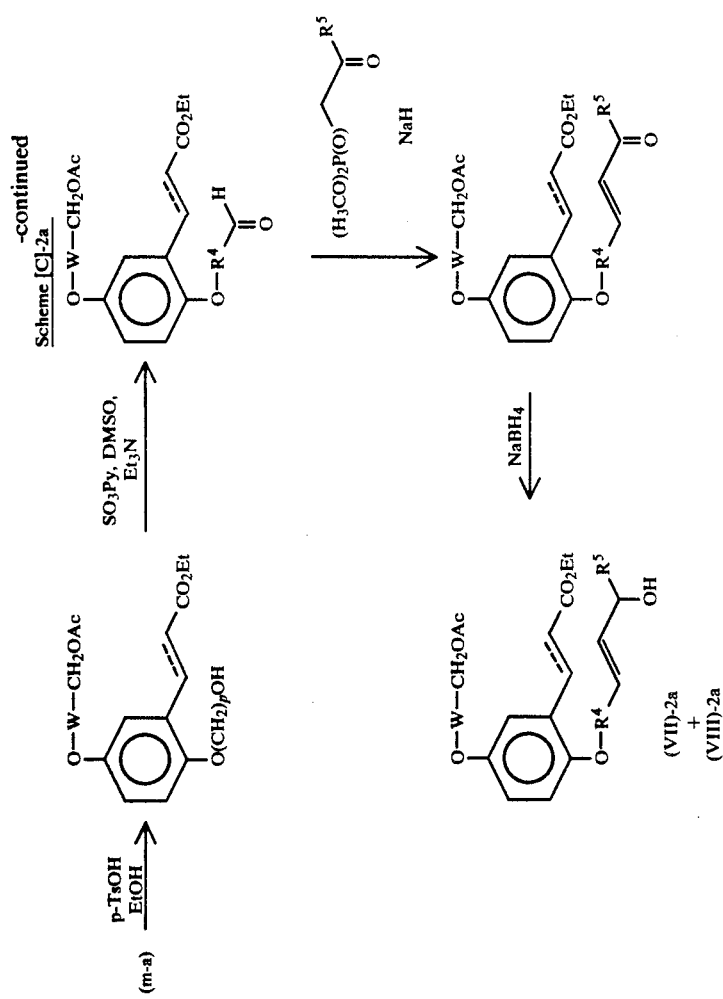

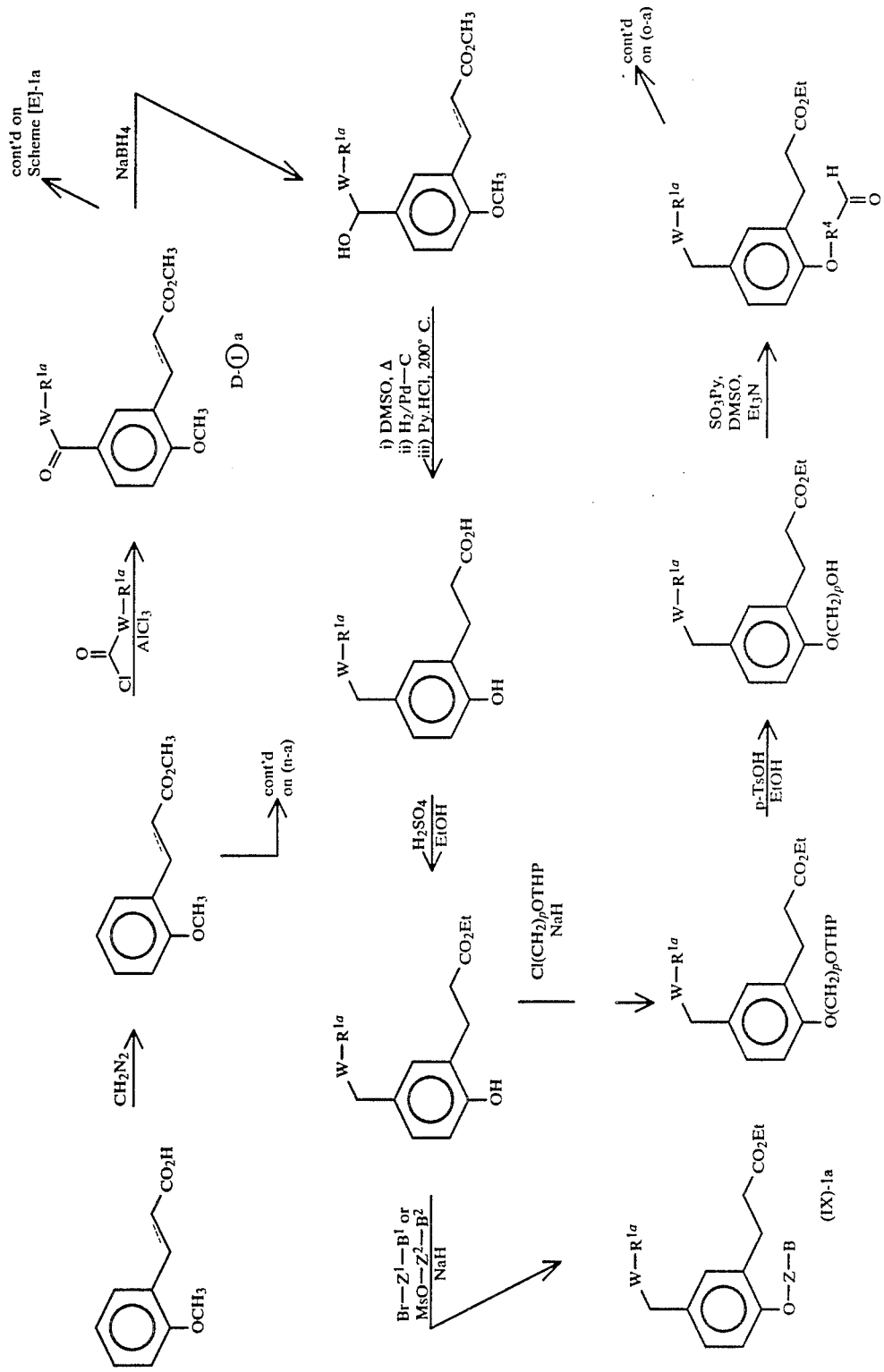

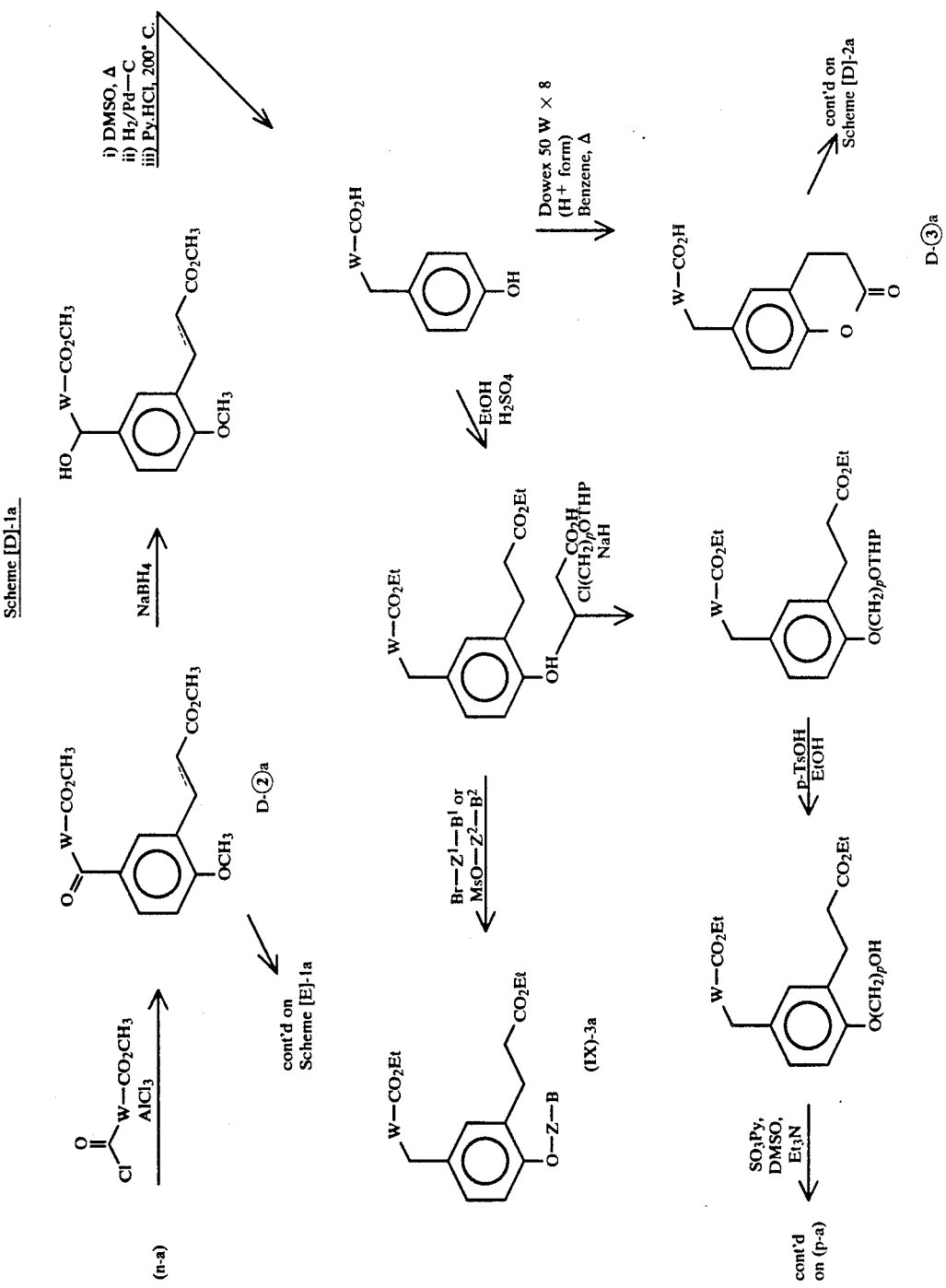

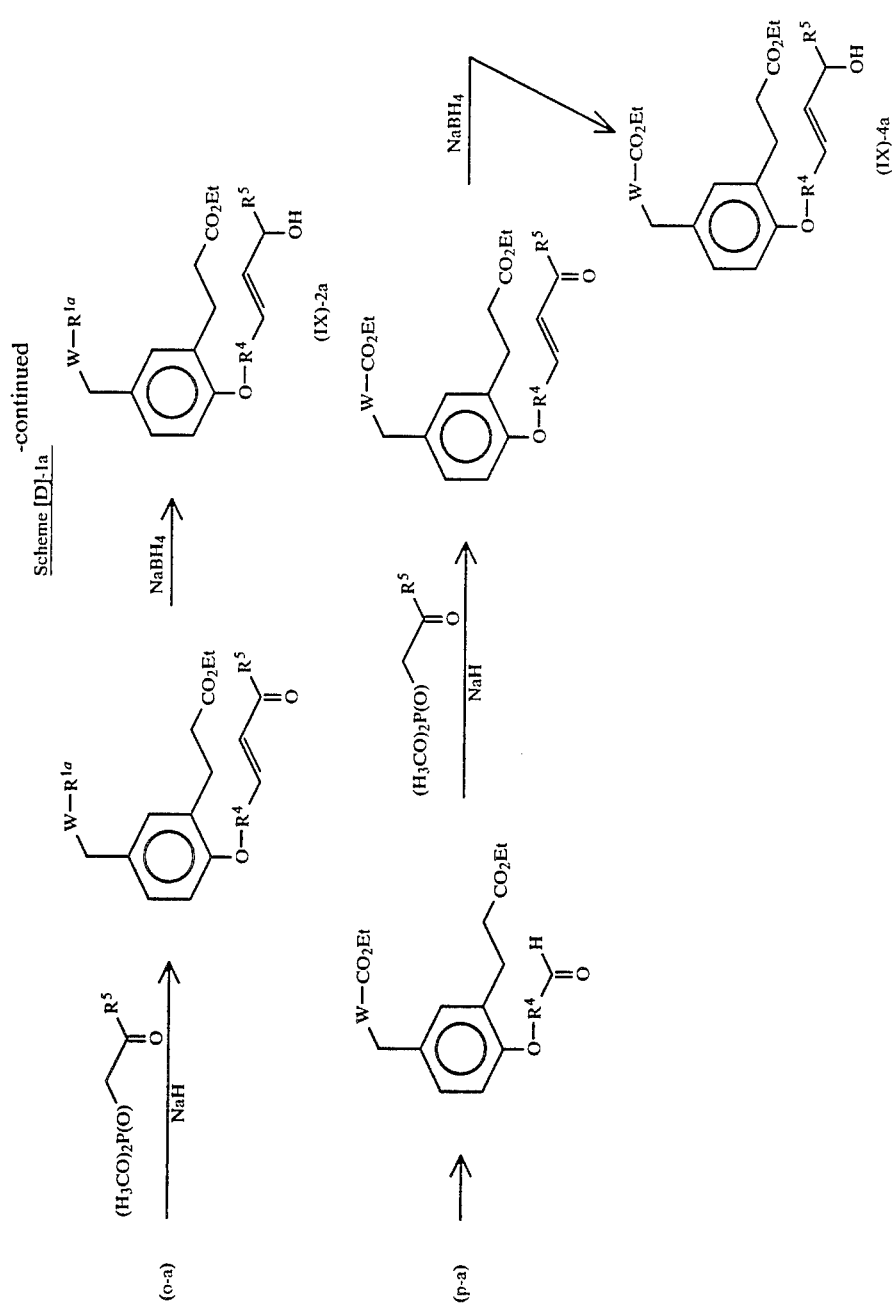

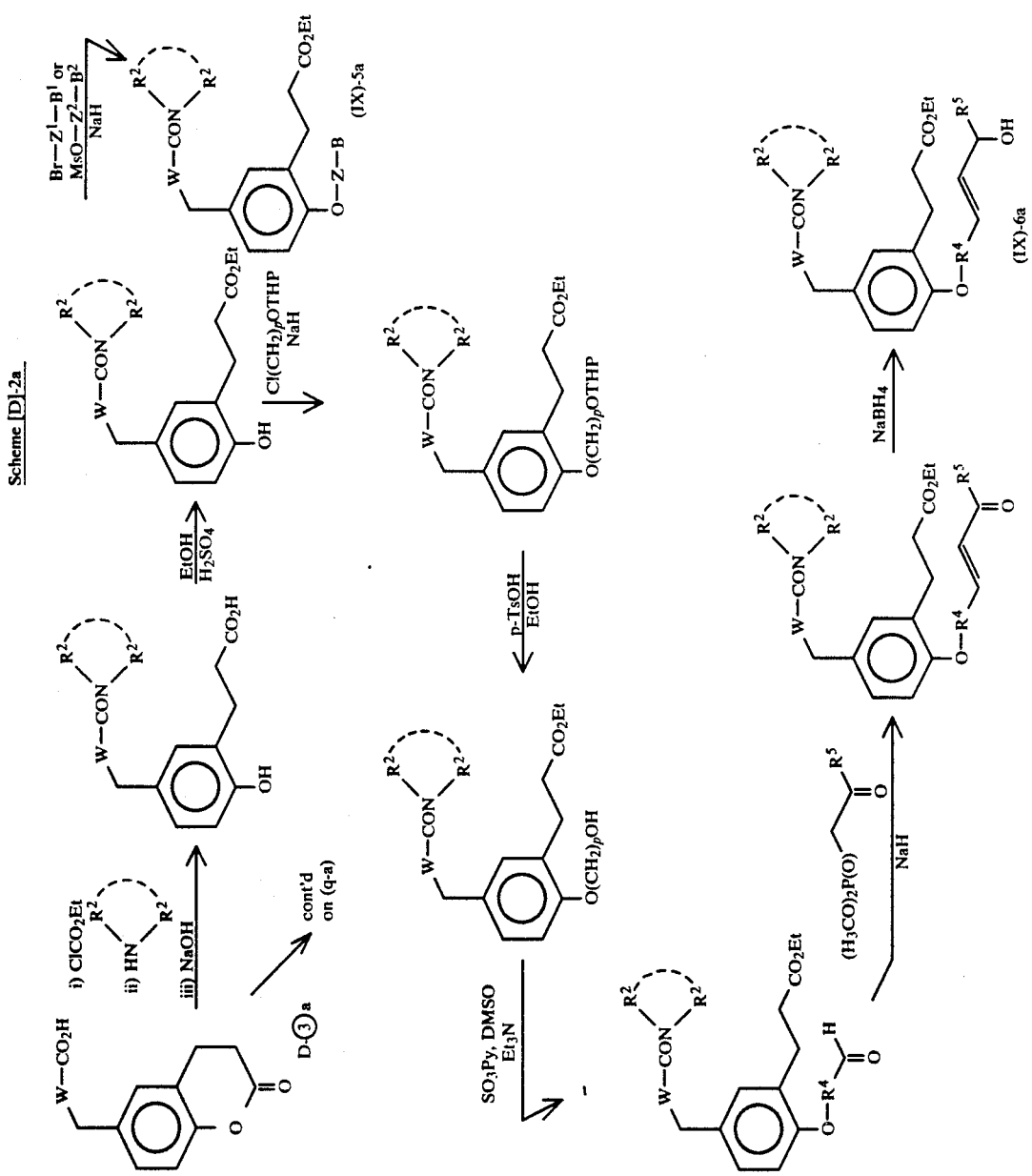

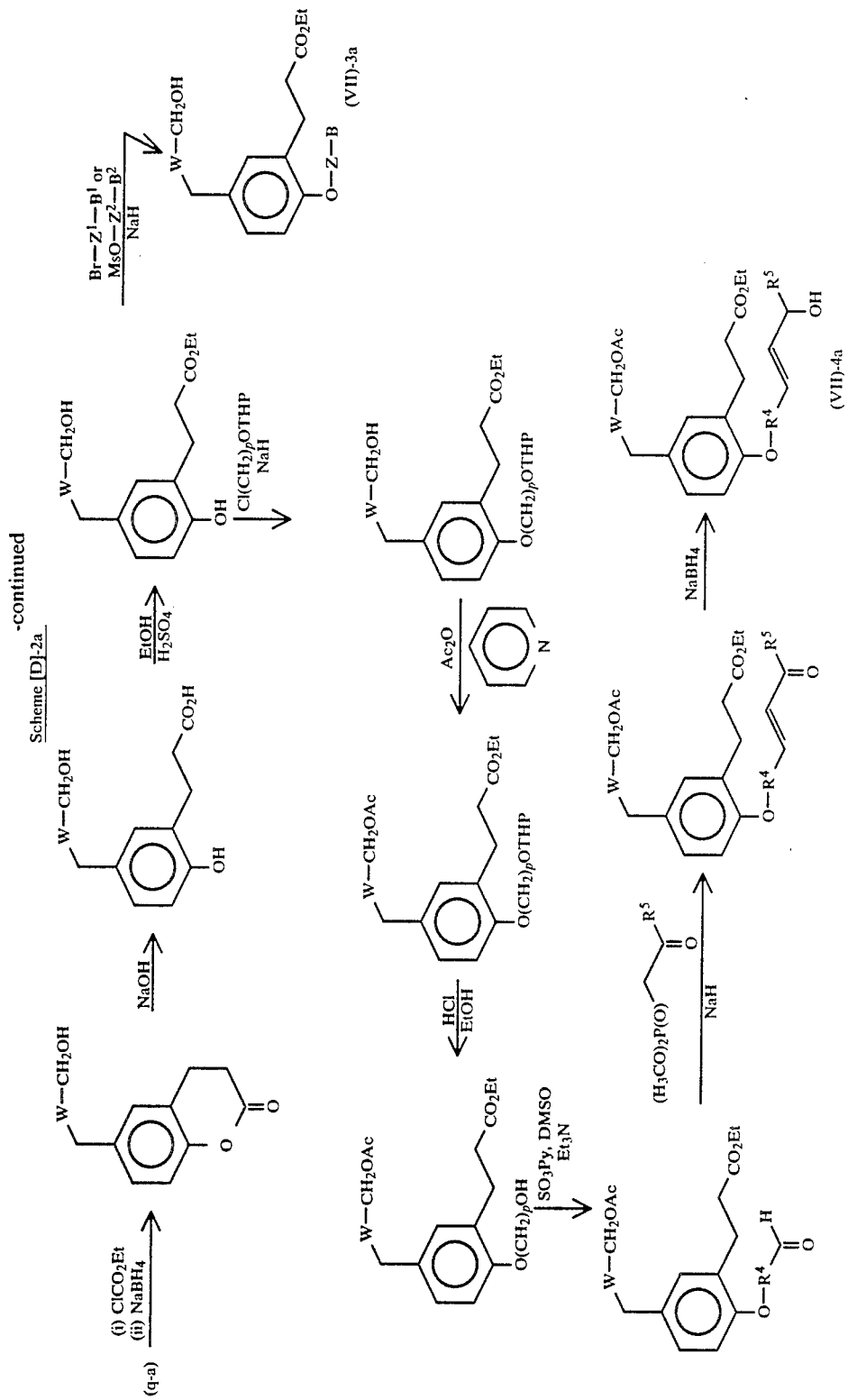

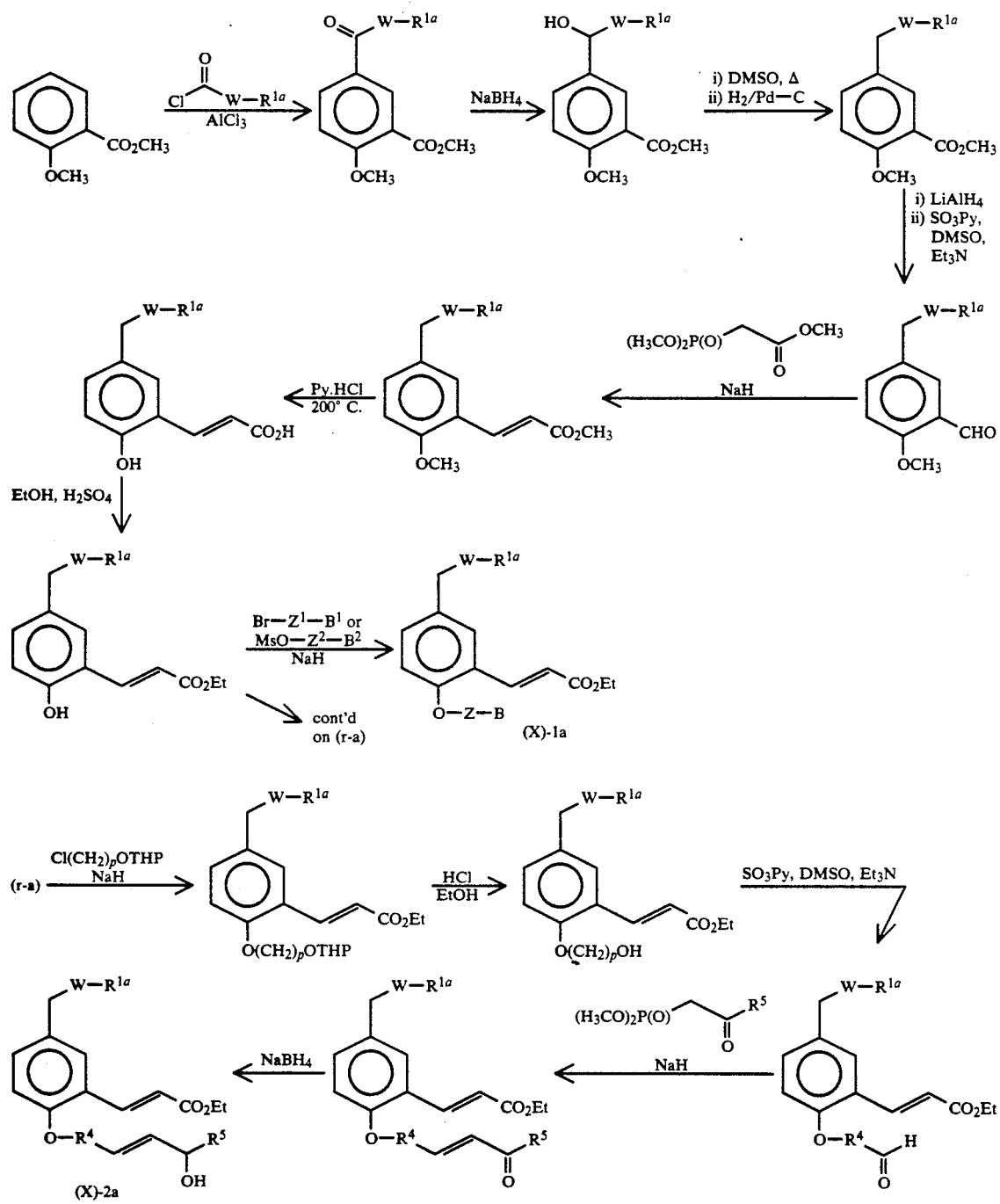
Scheme [D]-3a
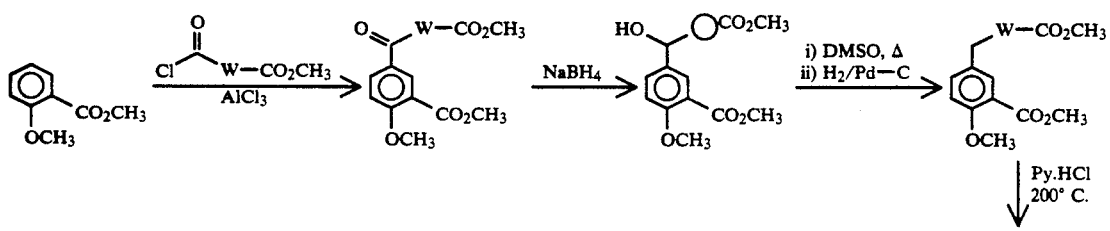
Scheme [D]-4a

-continued
Scheme [D]-4a
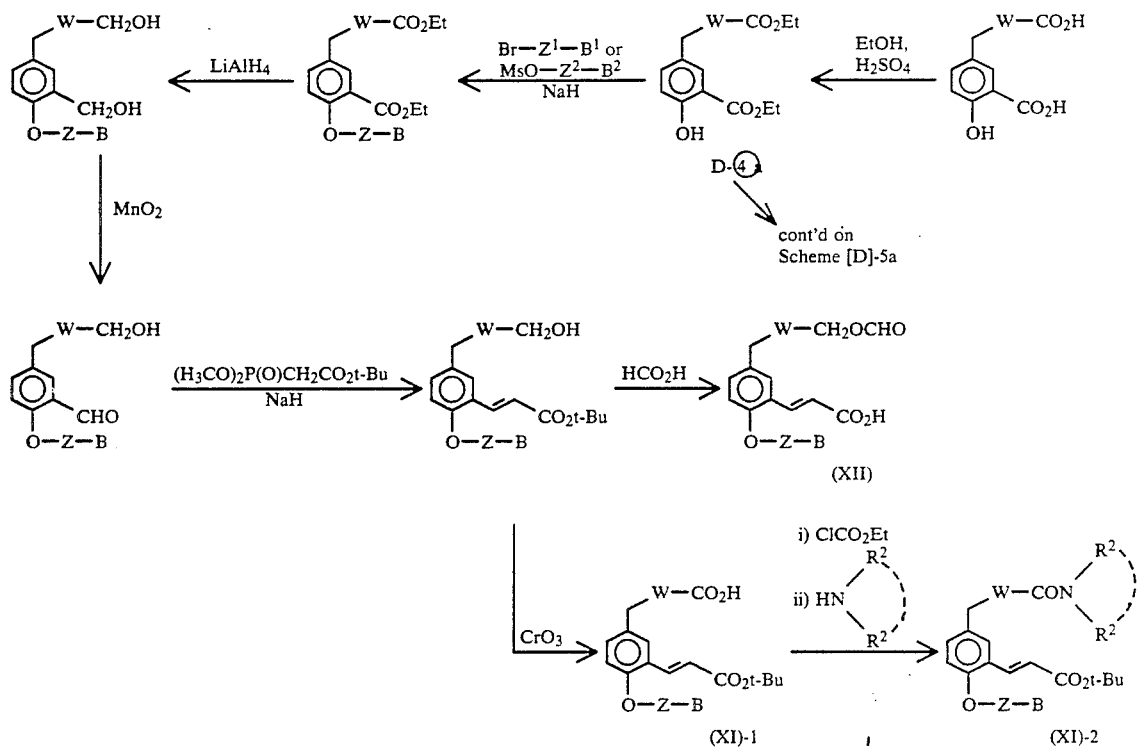
Scheme [D]-5a
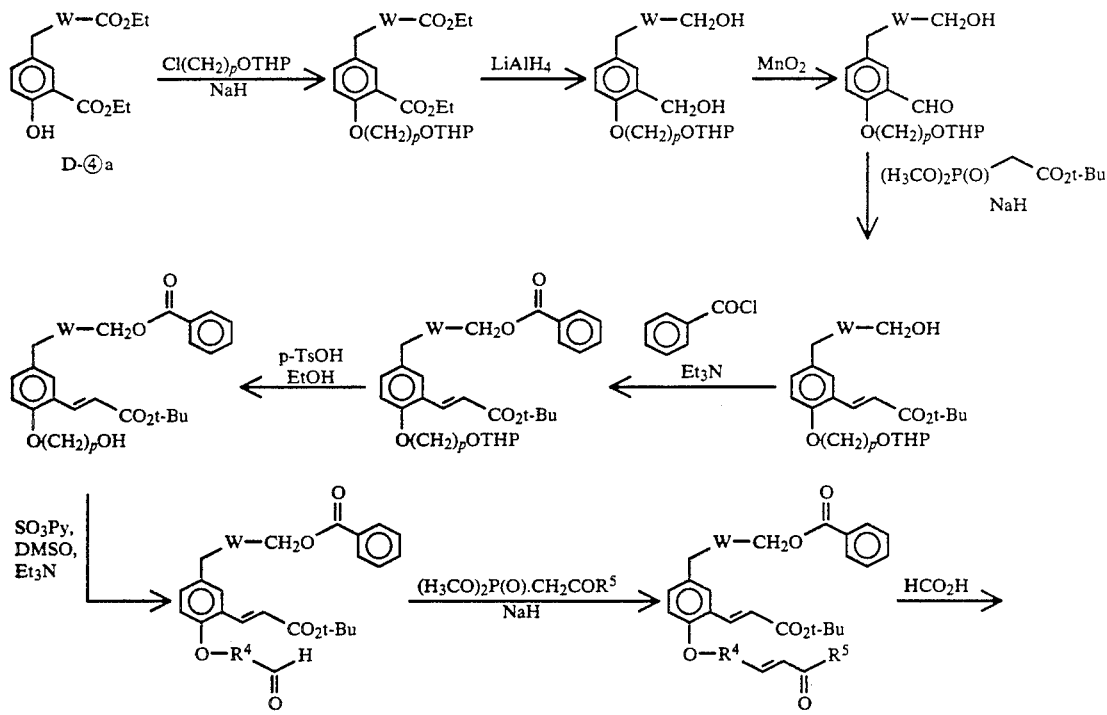

Scheme [D]-5a
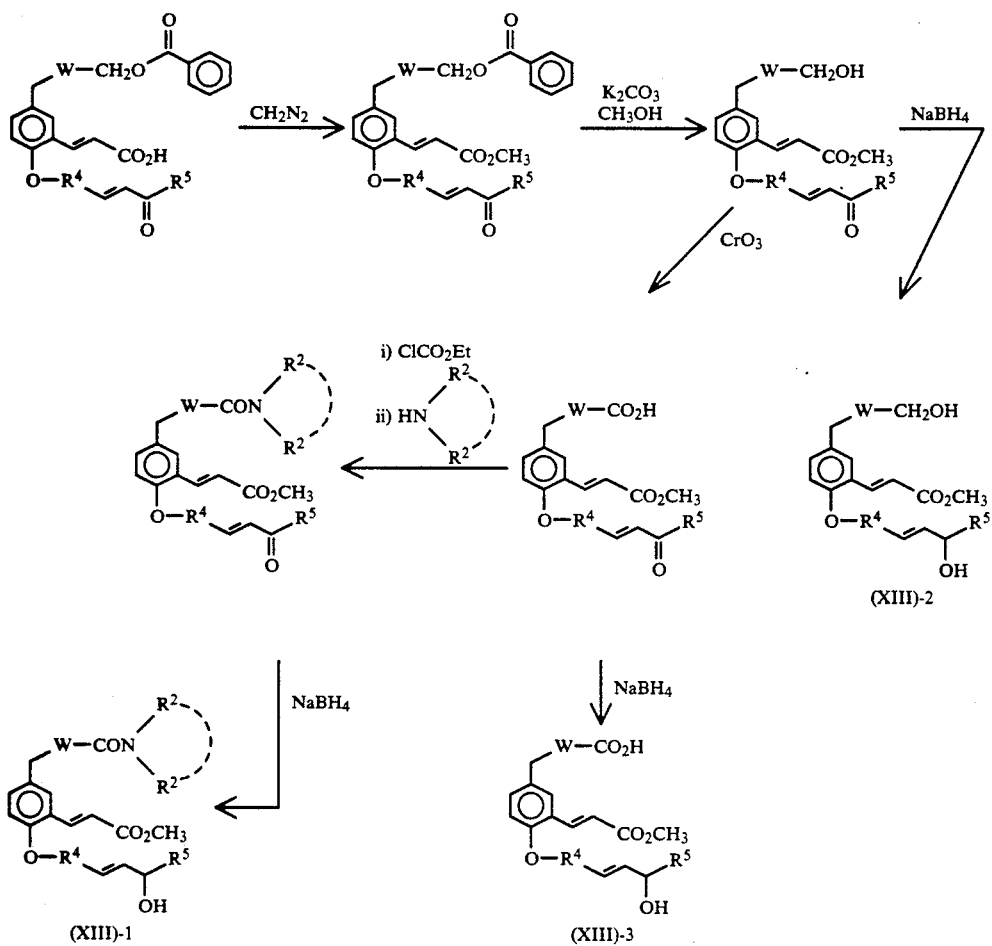
Scheme [E]-1a
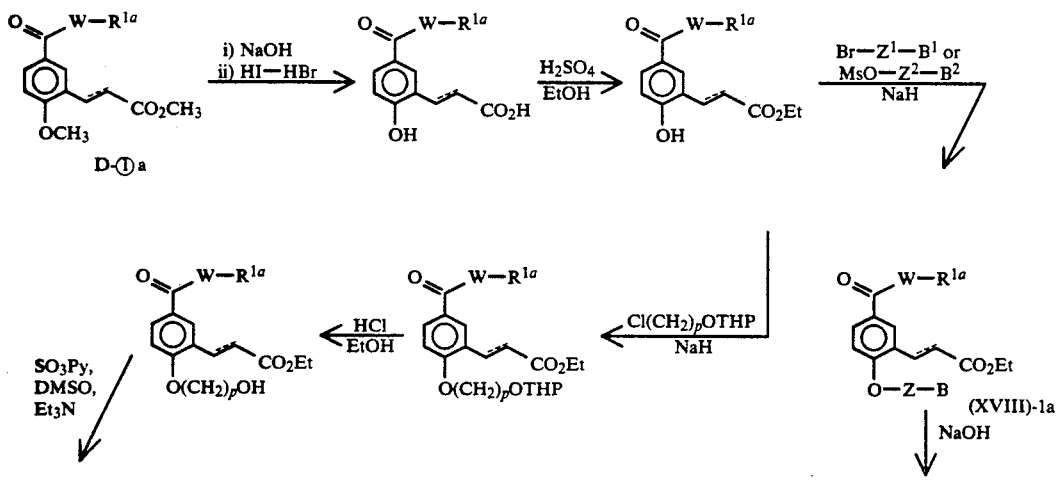

5,086,065
-continued
Scheme [E]-1a
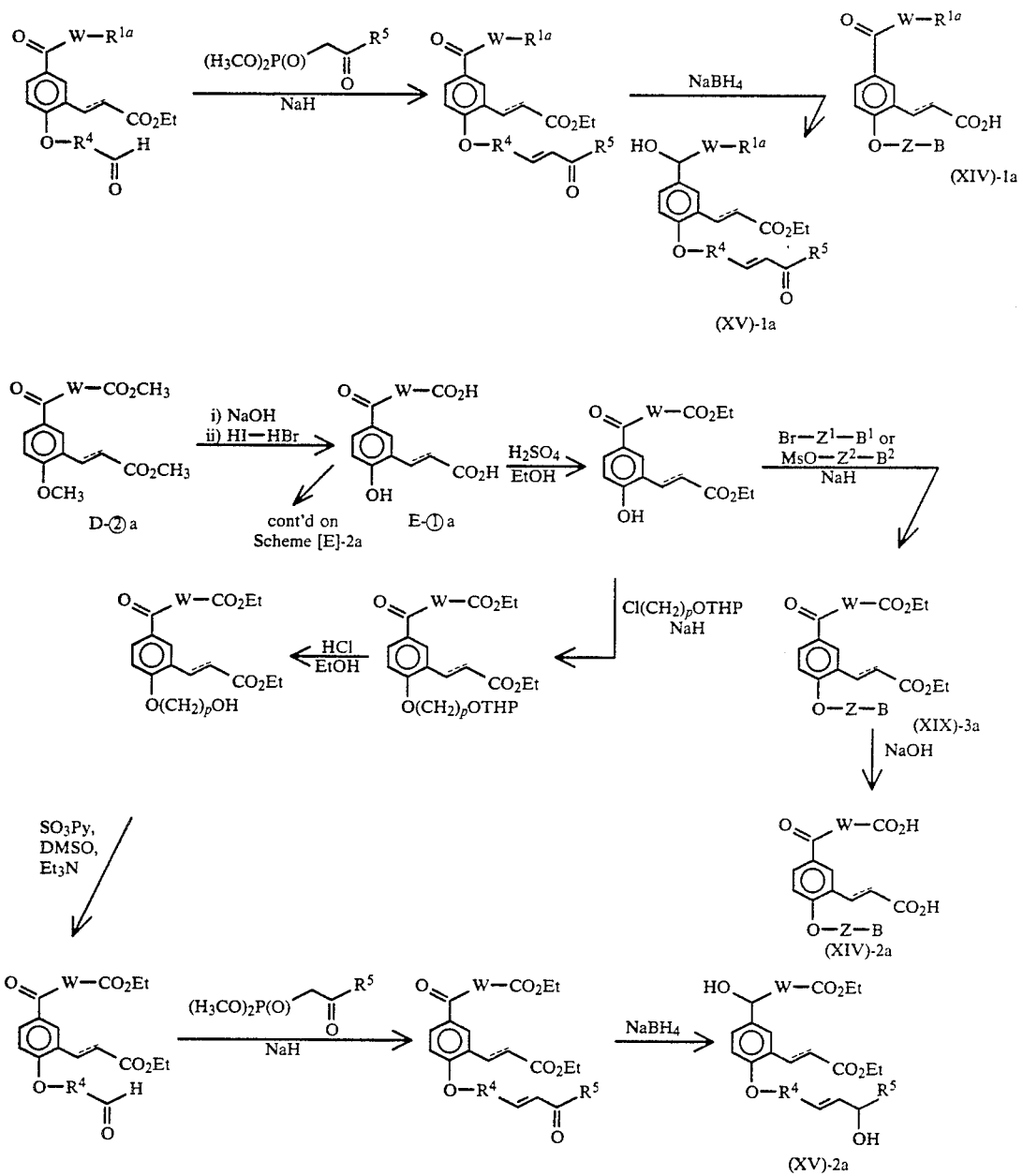
Scheme [E]-2a
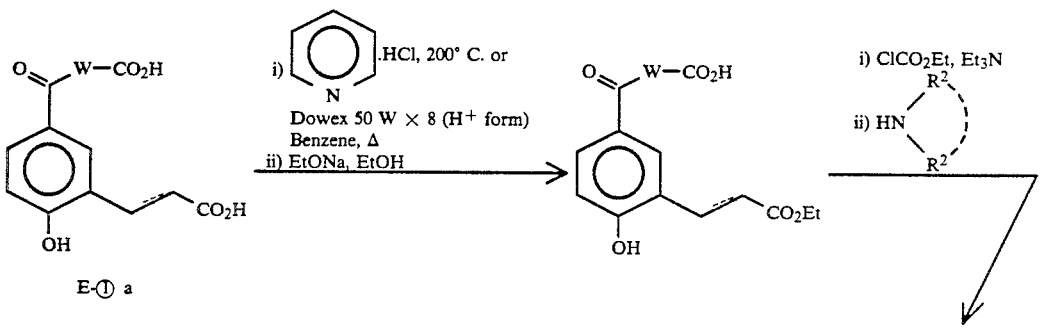

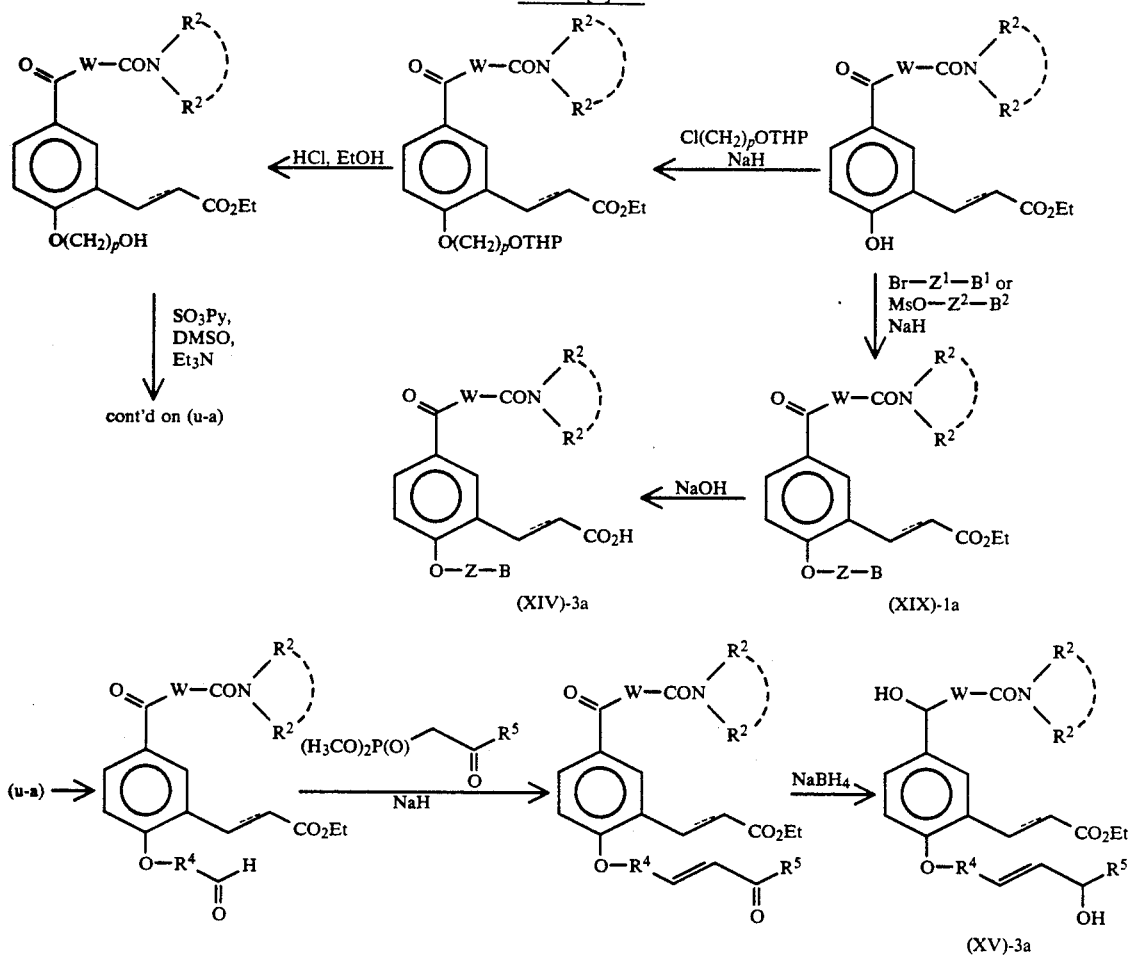

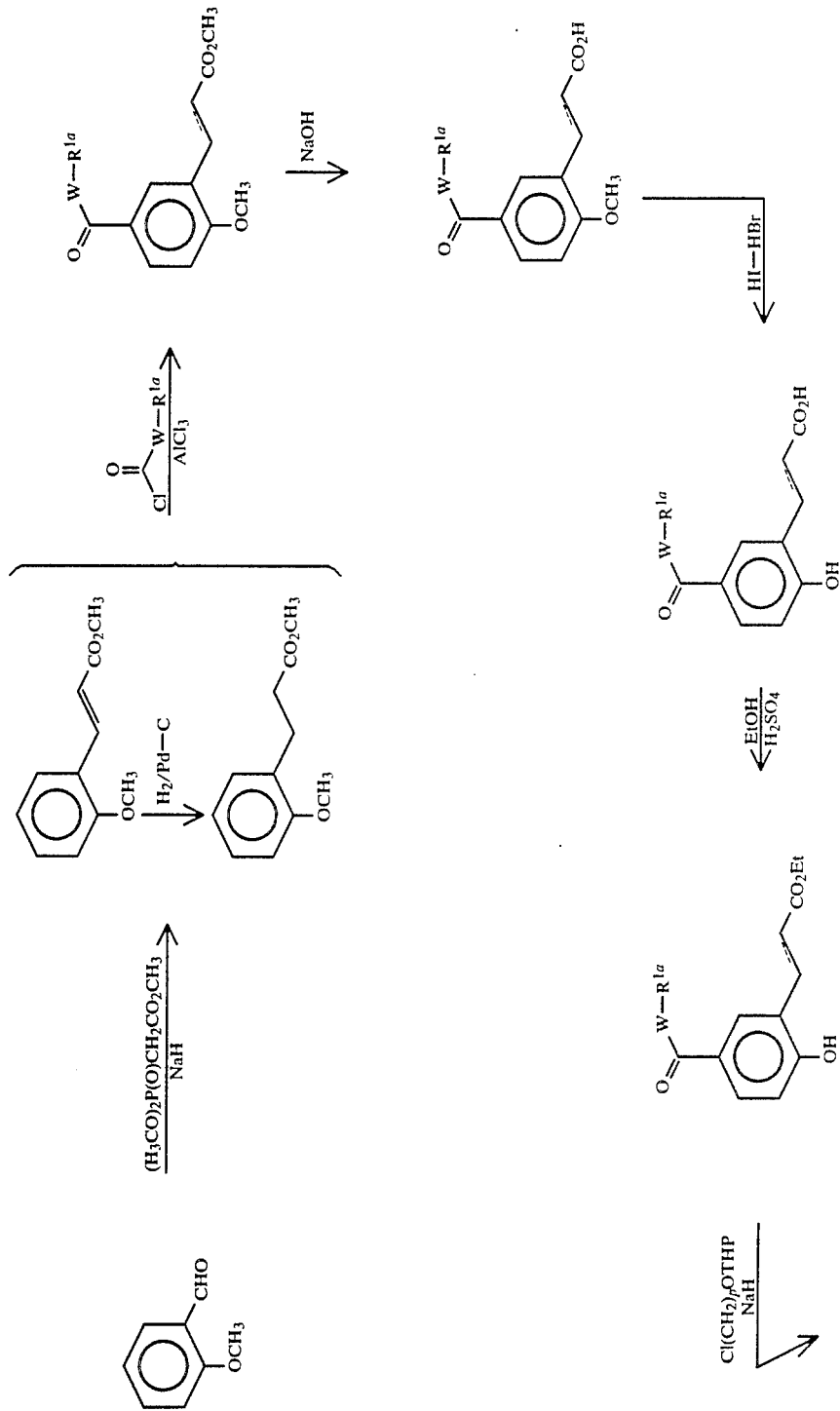

Scheme [E]-3b
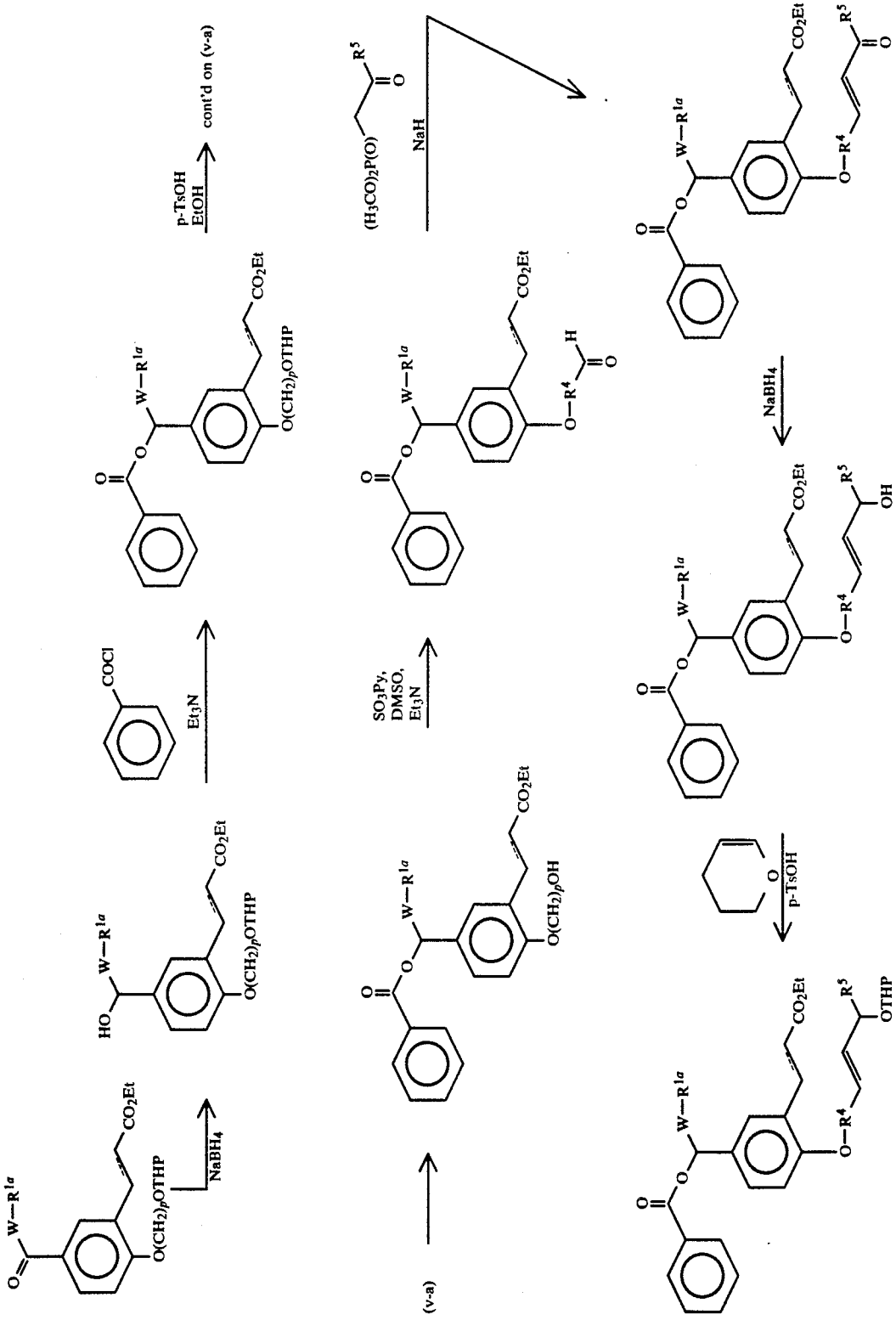

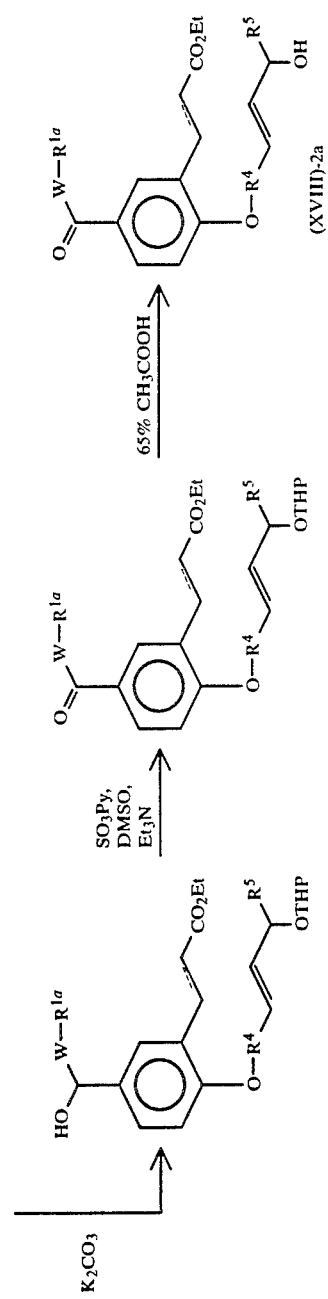

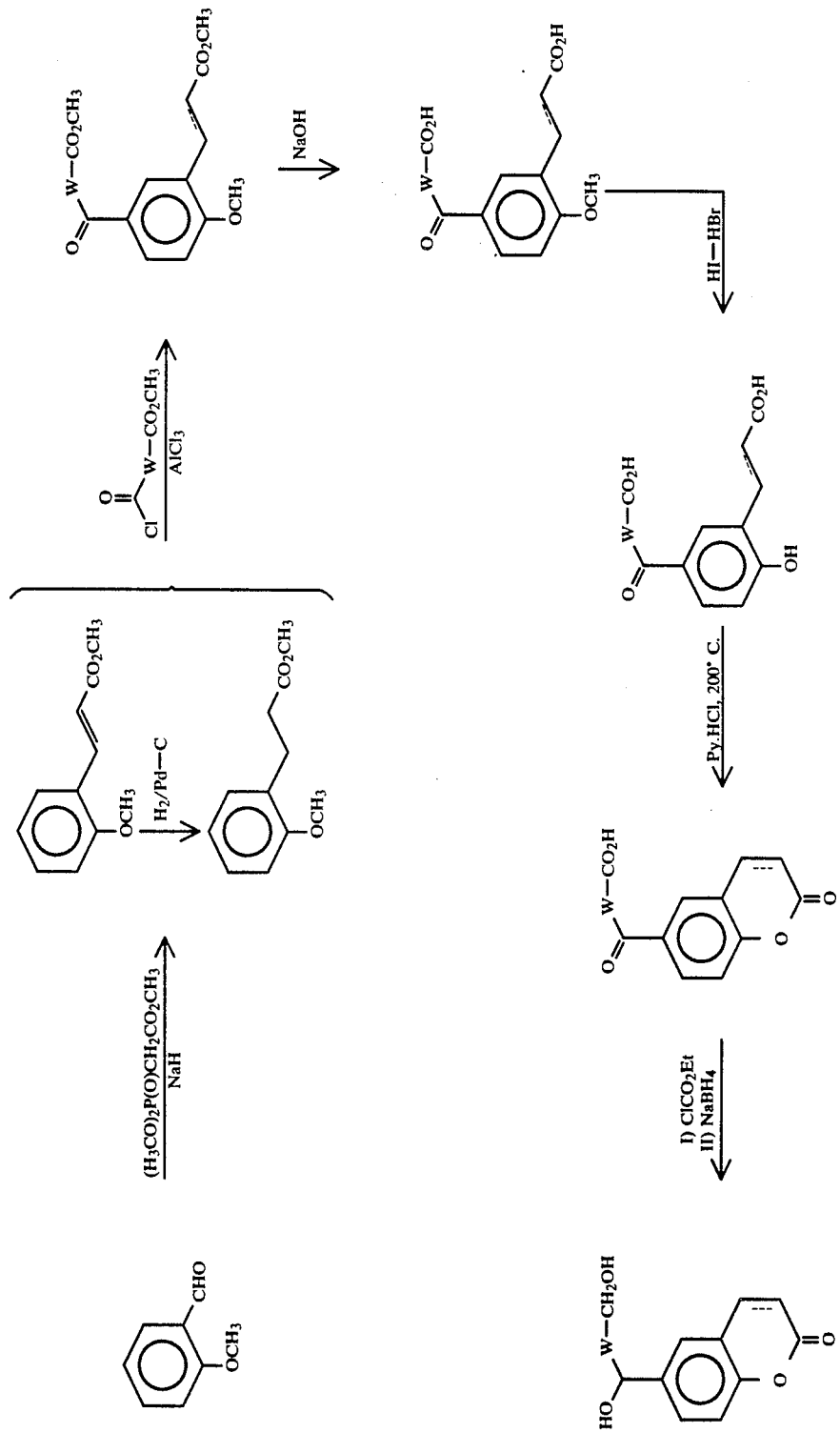
Scheme [E]-4a

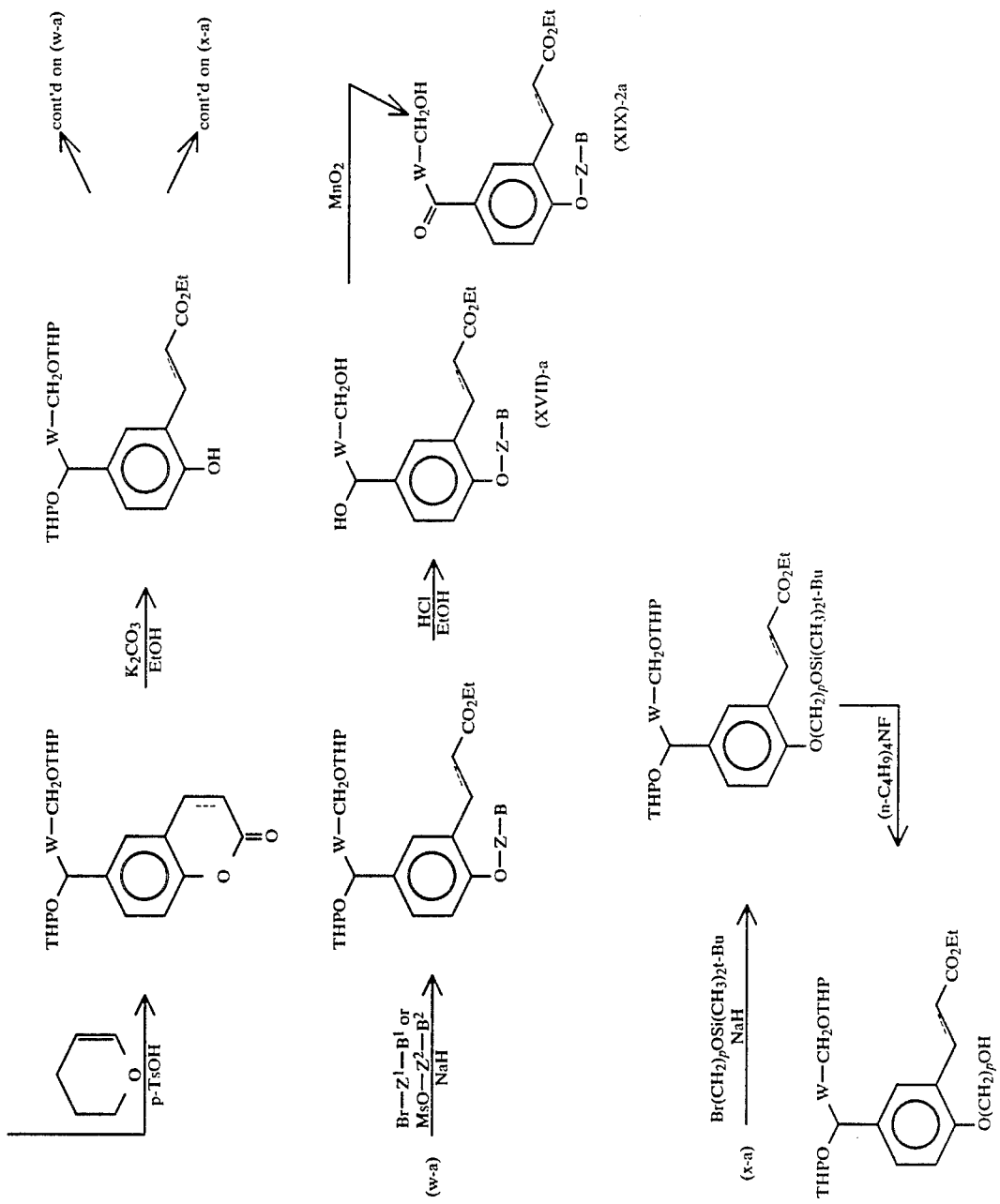

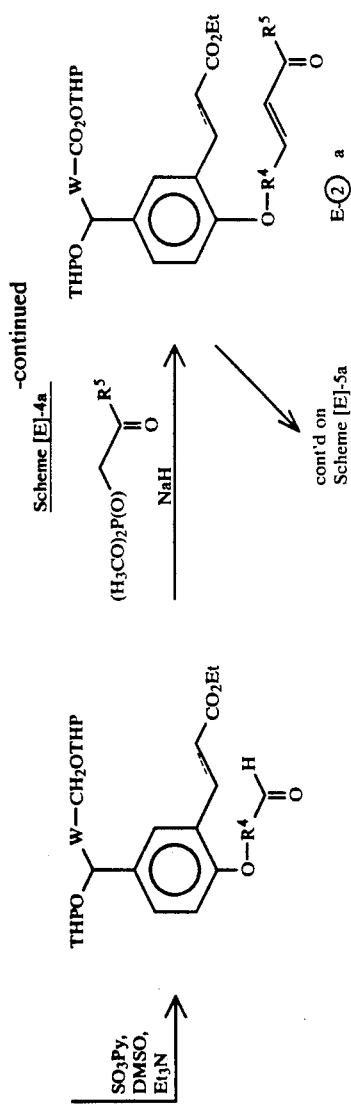

Scheme [E]-5a
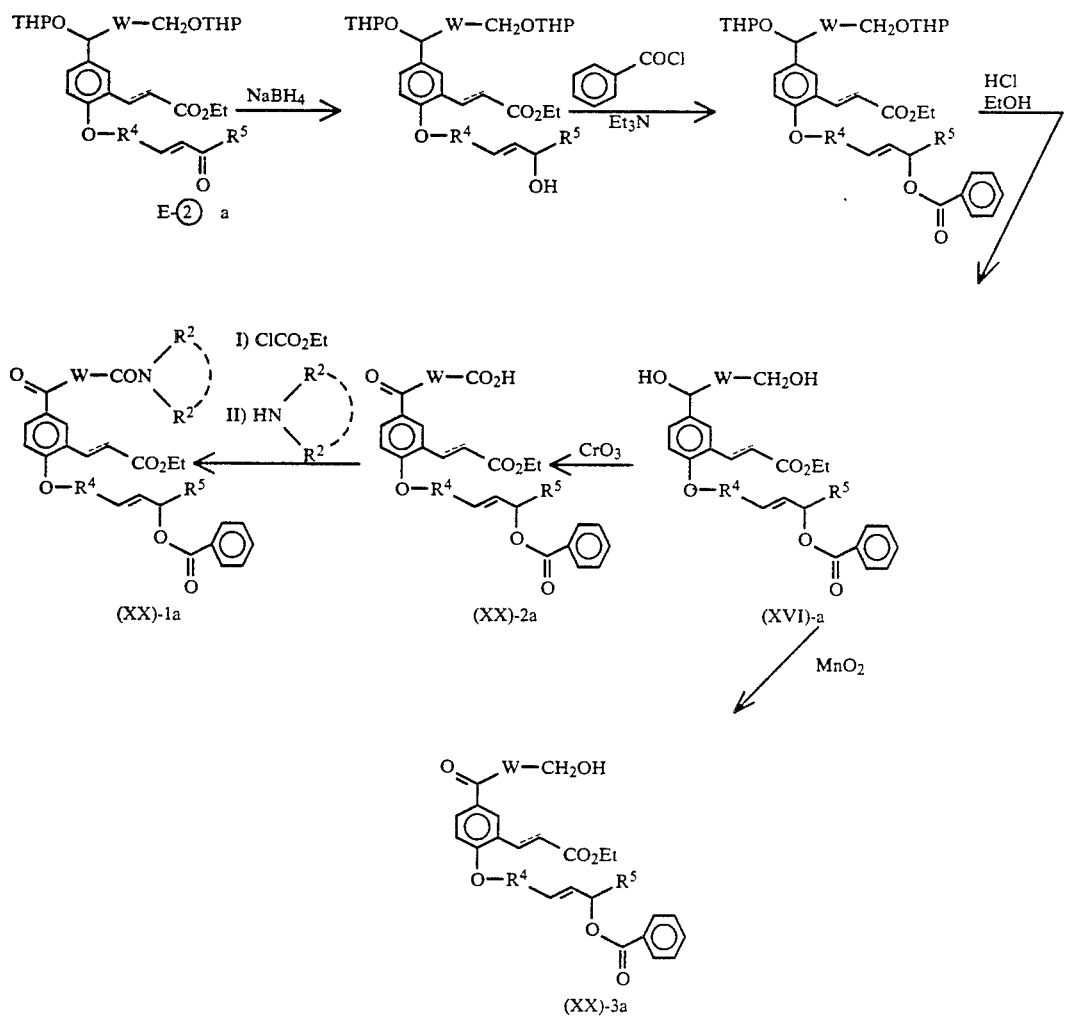
Scheme [C]-1b
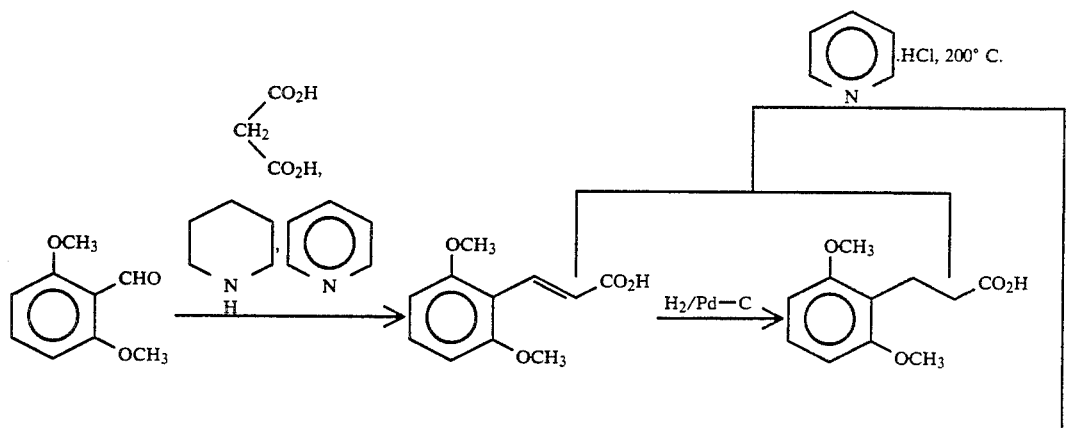

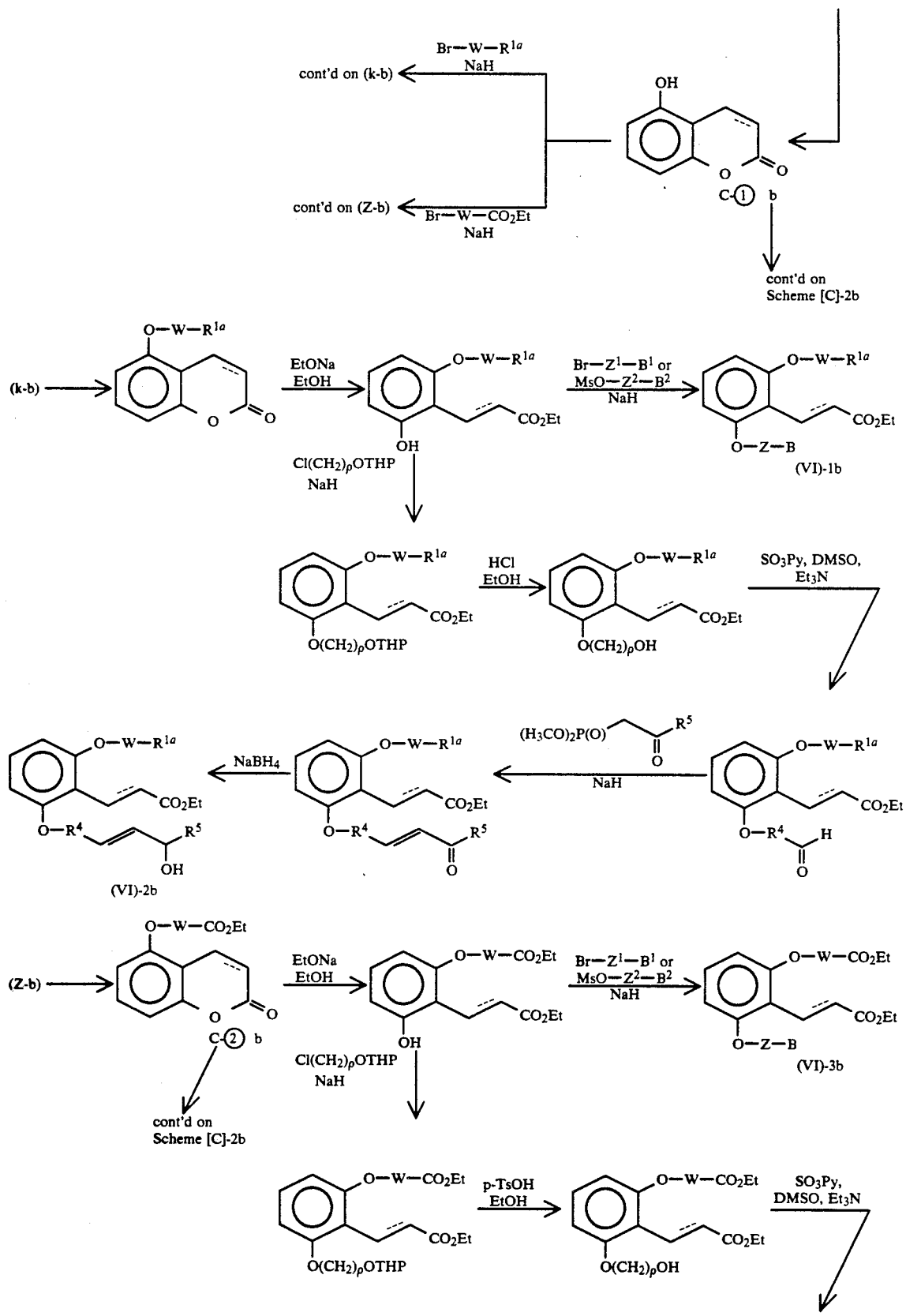

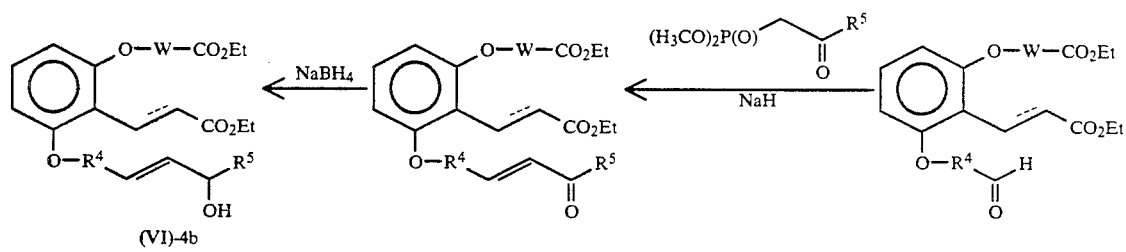

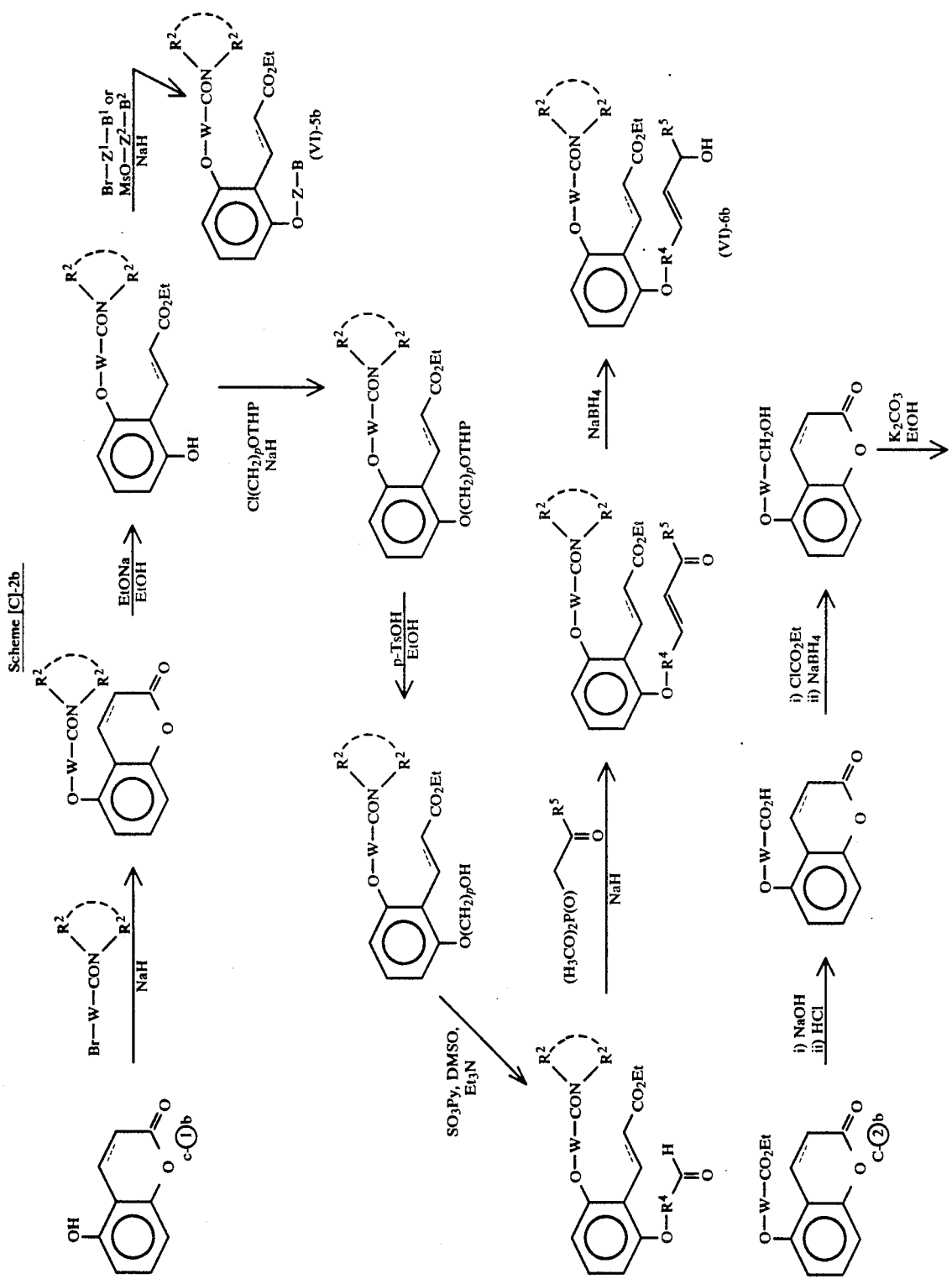

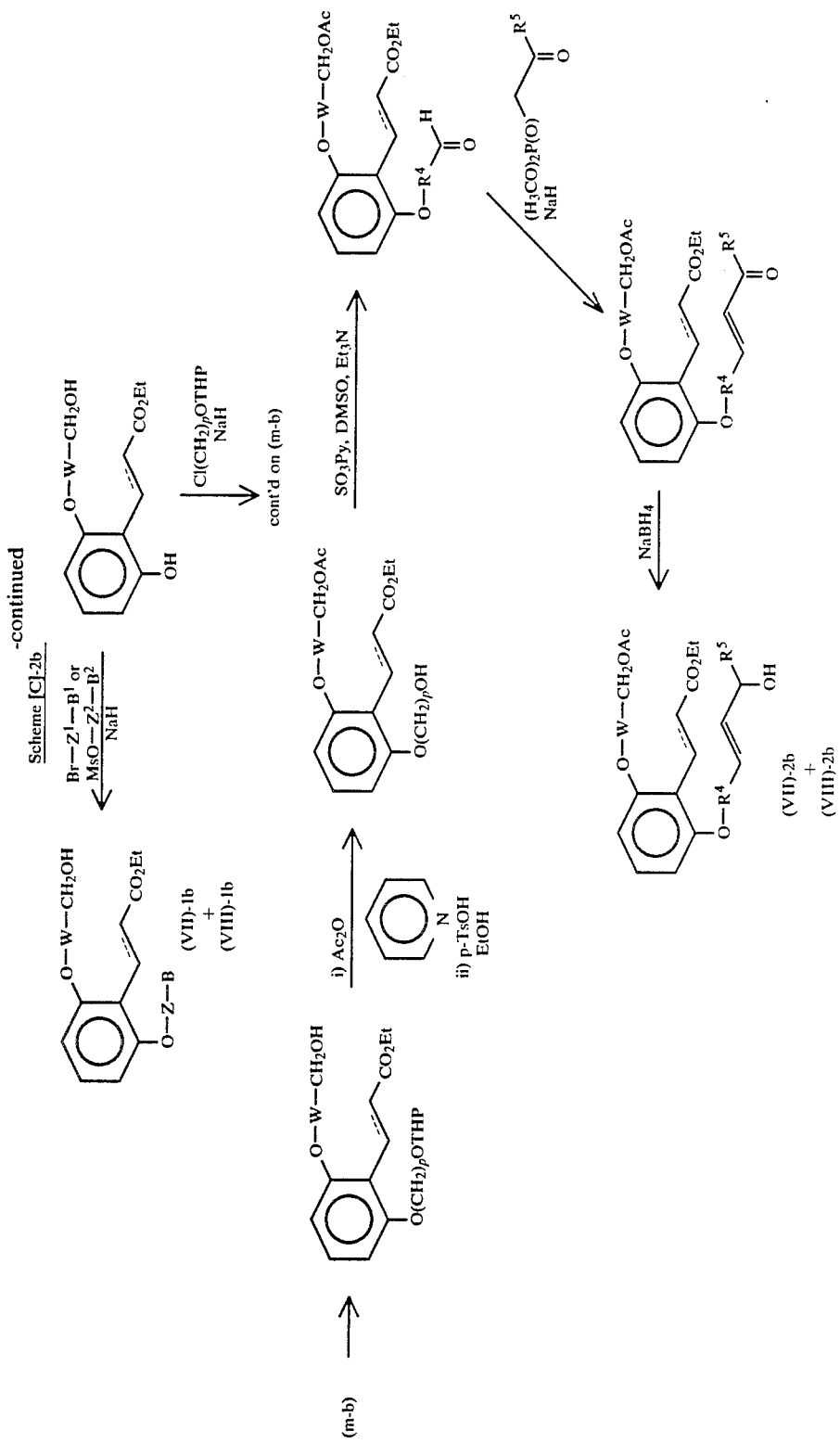

Scheme [D]-1b
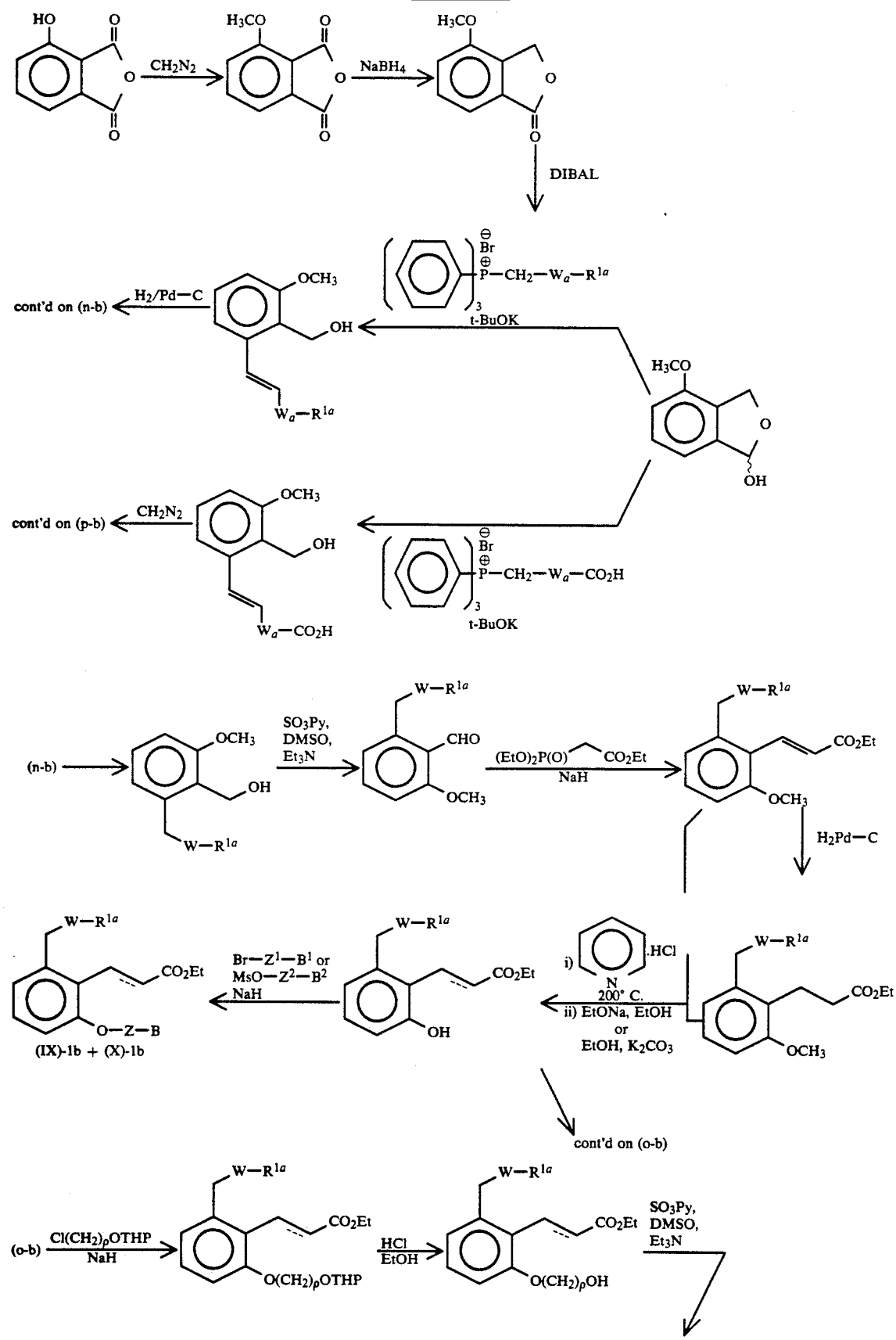

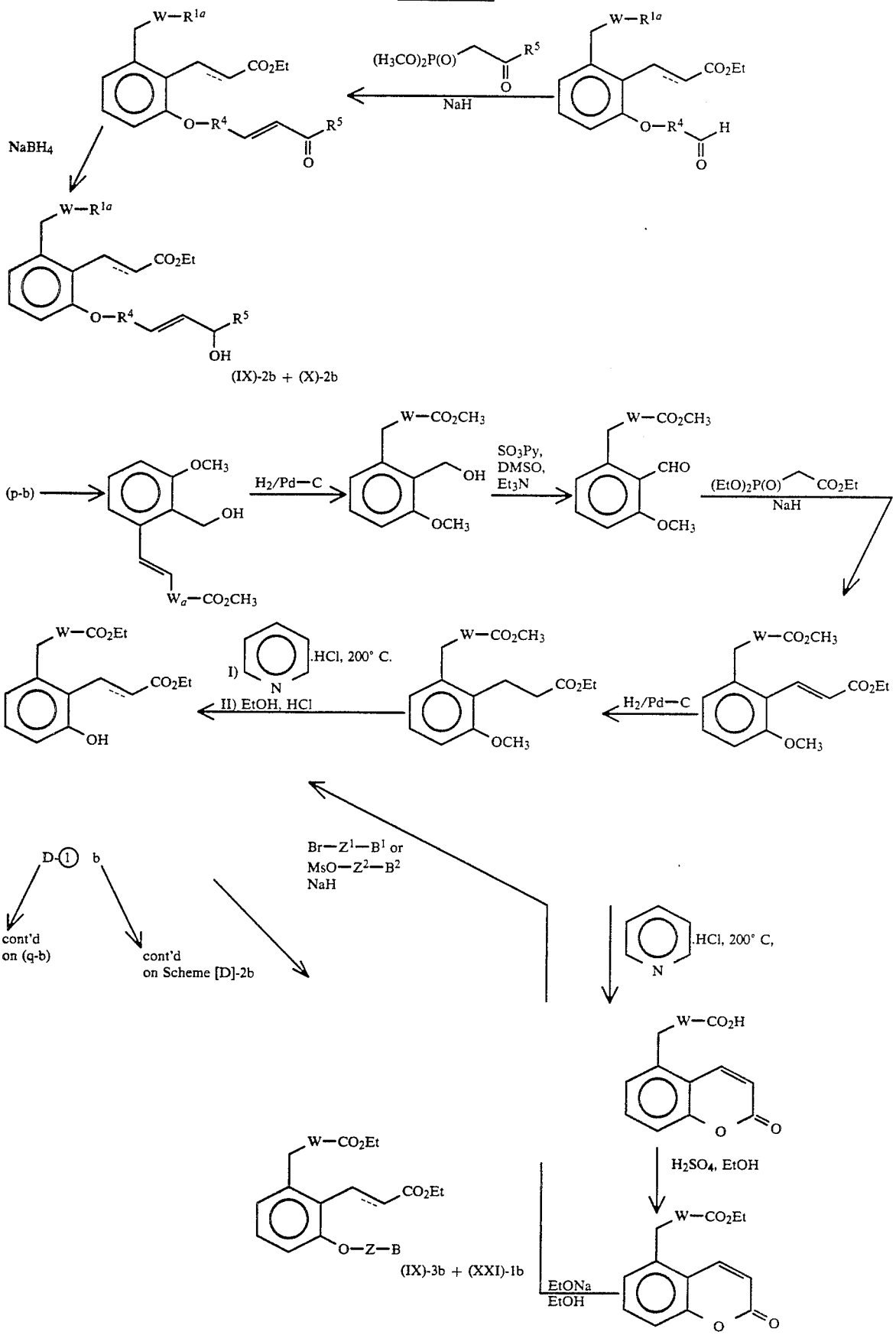

-continued
Scheme [D]-1b
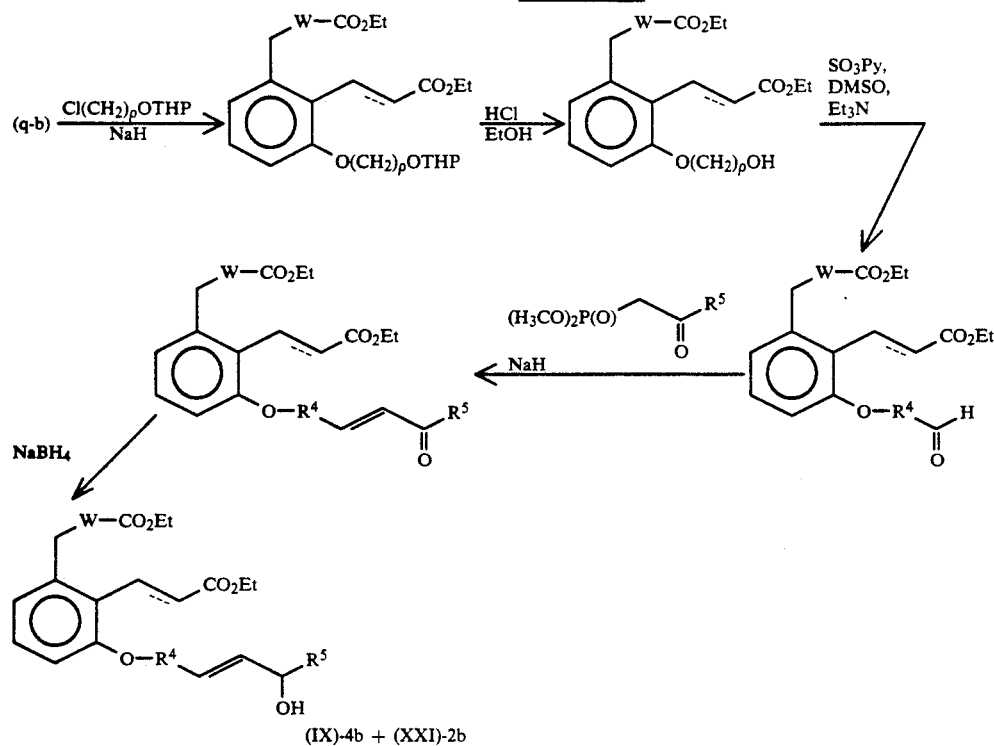

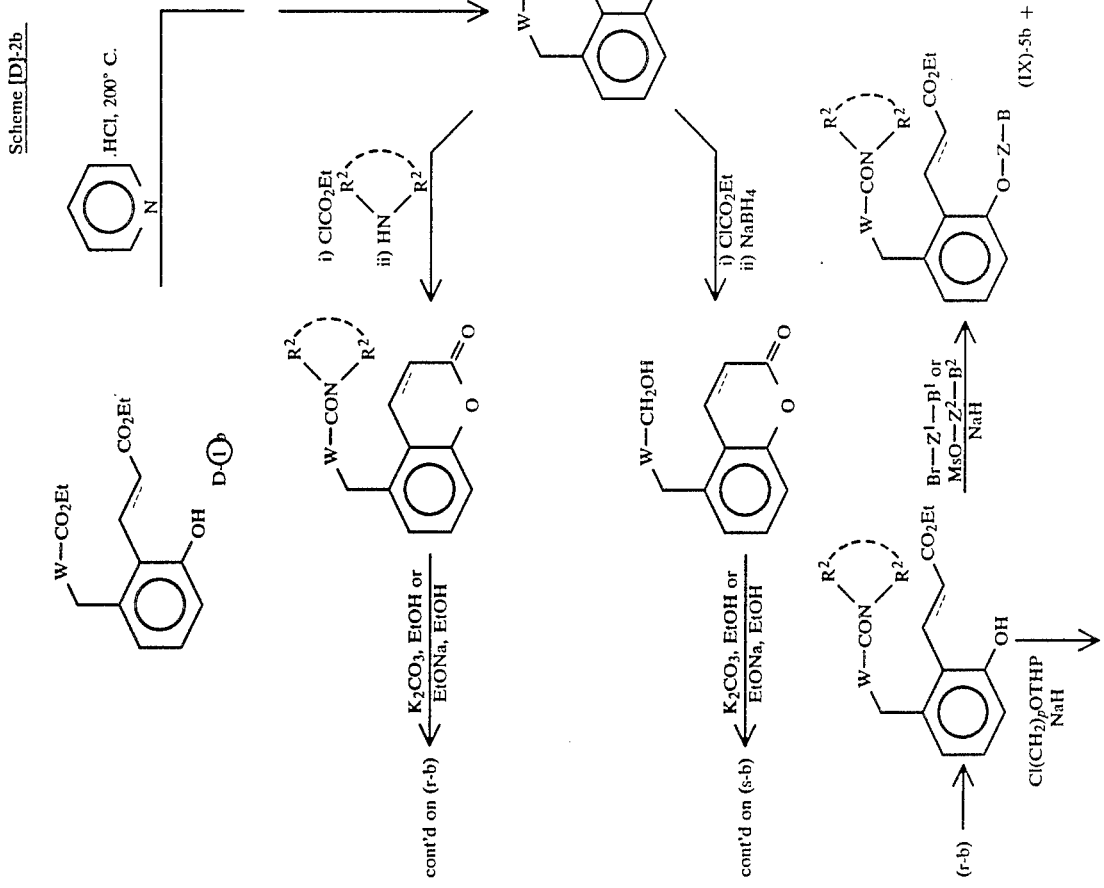
Scheme [D]-2b

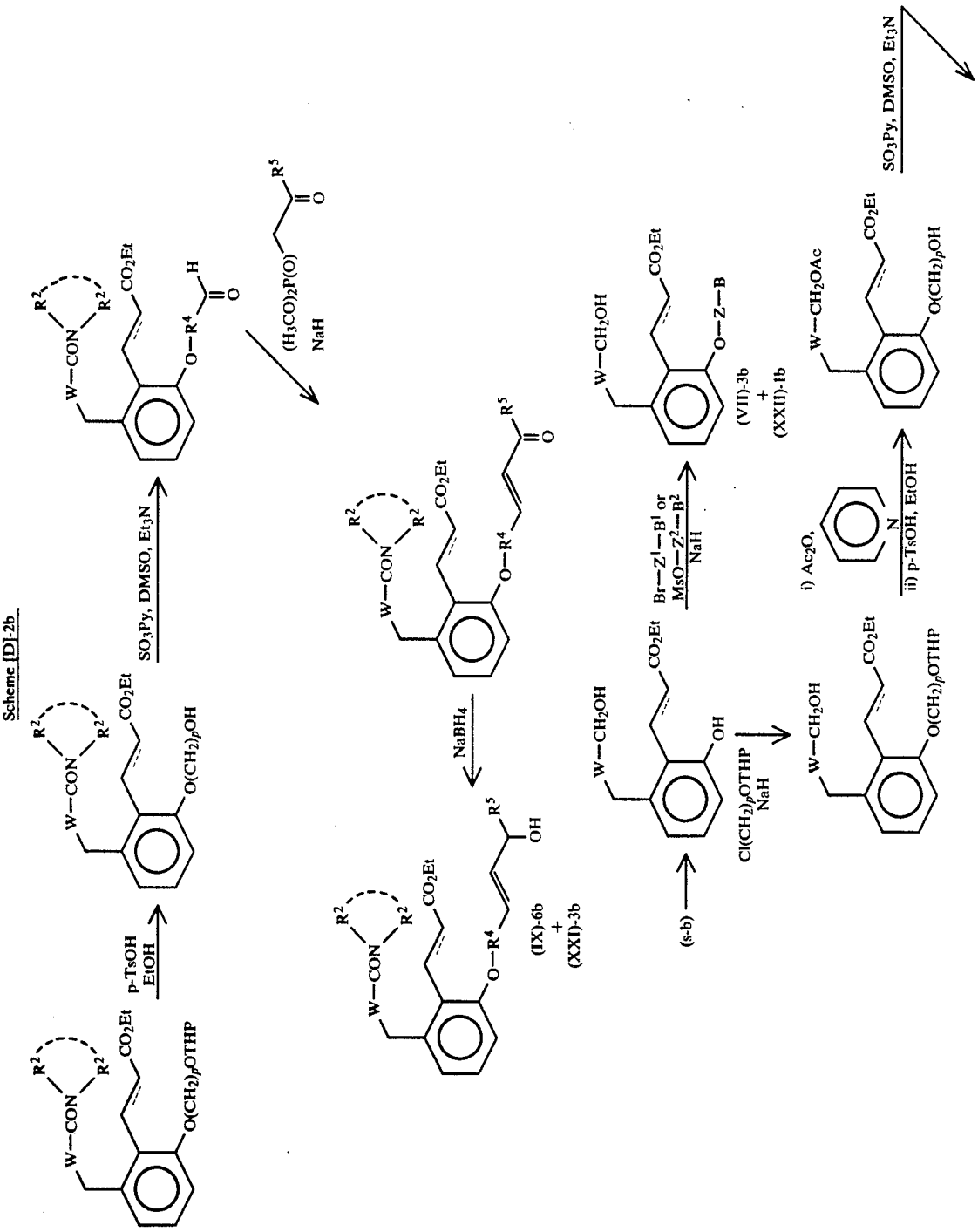

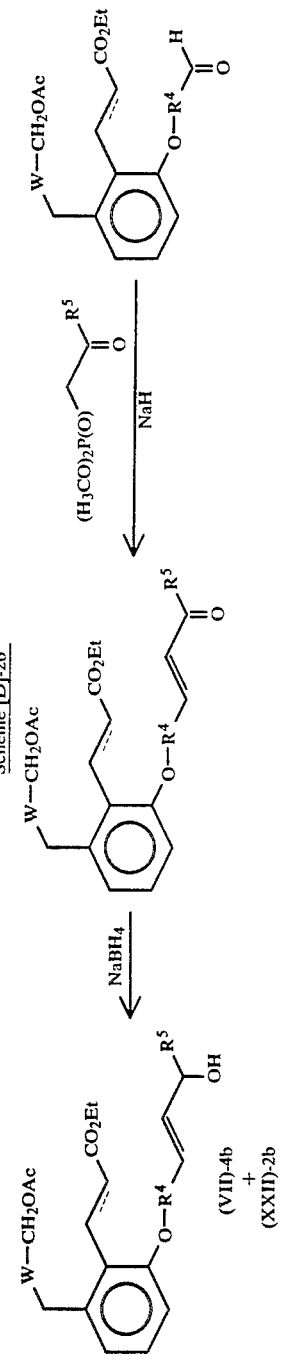

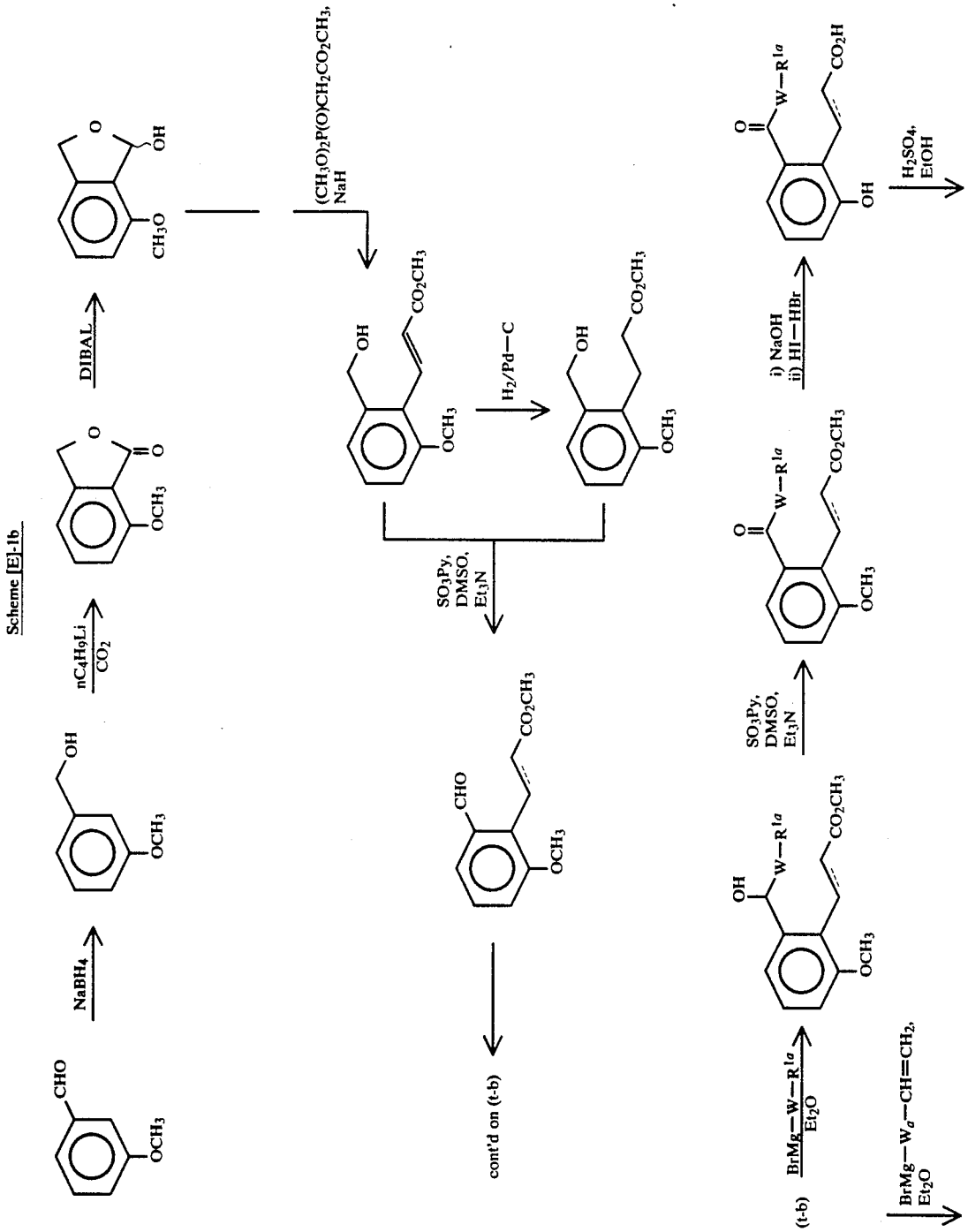

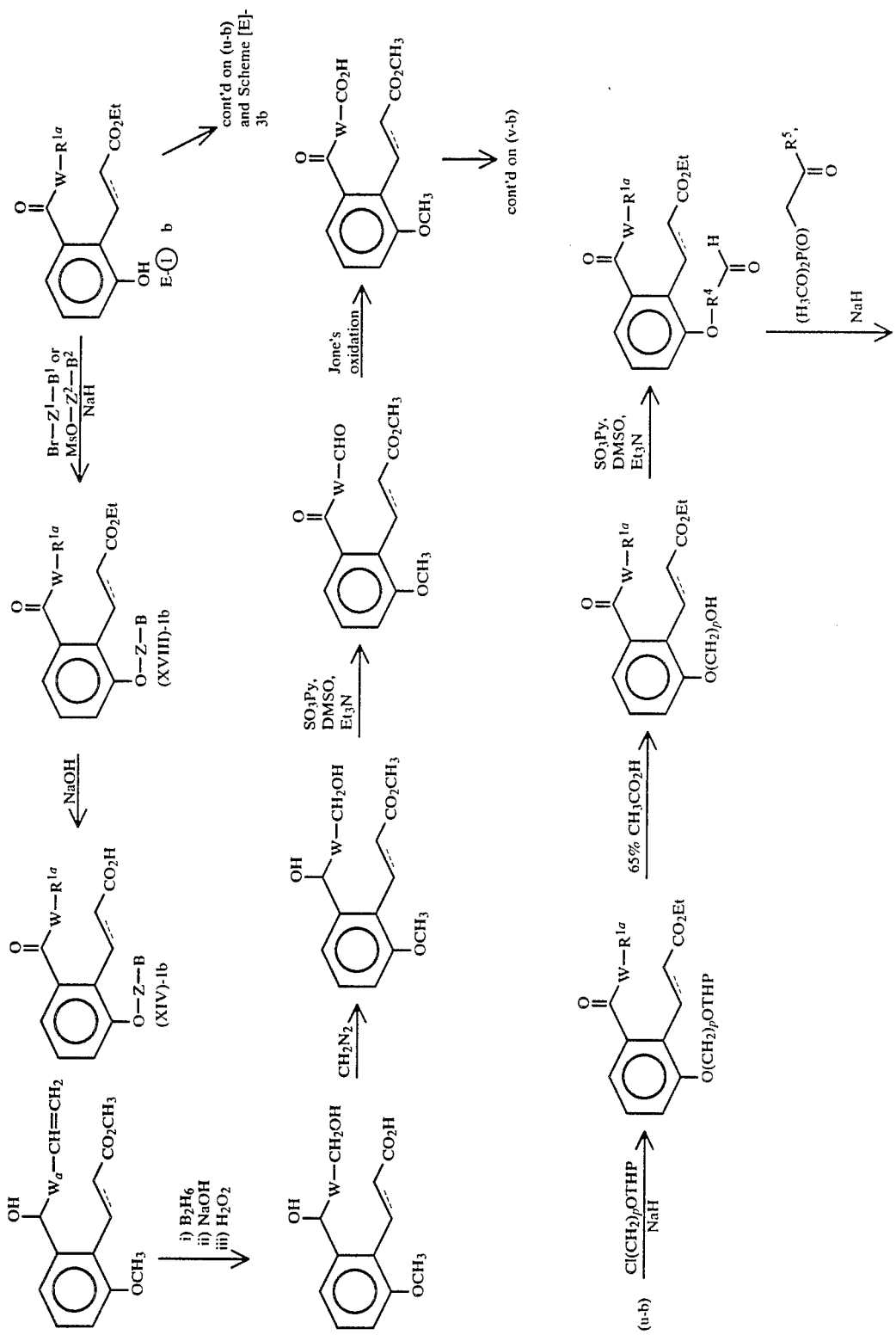

Scheme [E]-1b
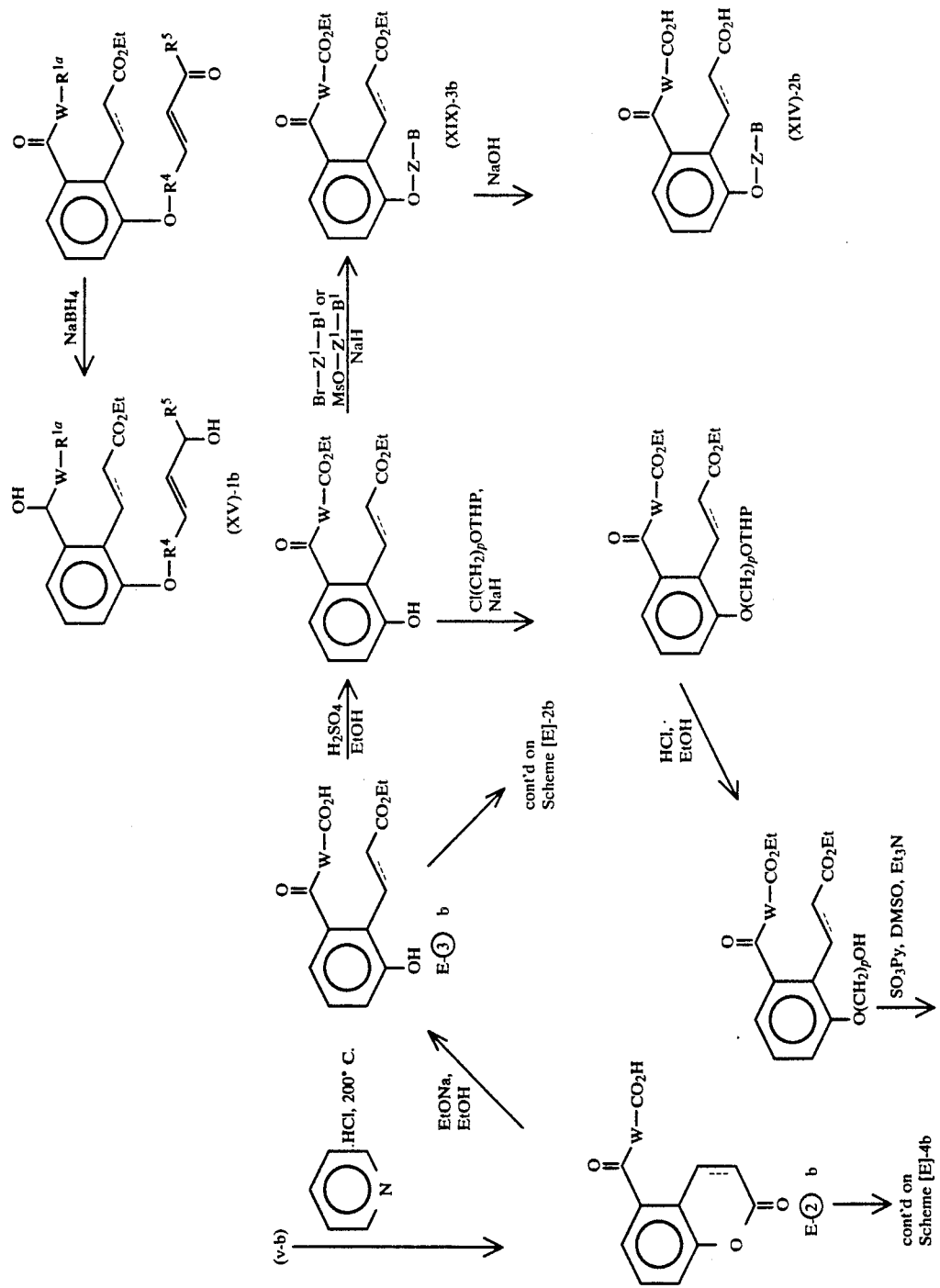

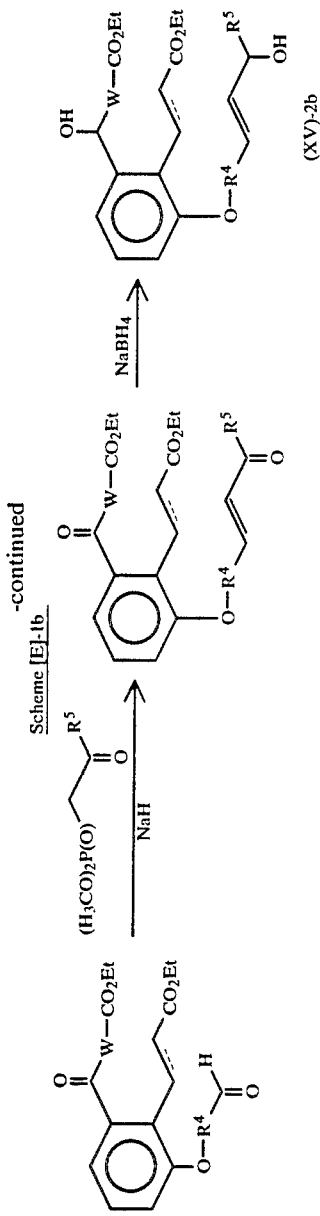

Scheme [E]-2b
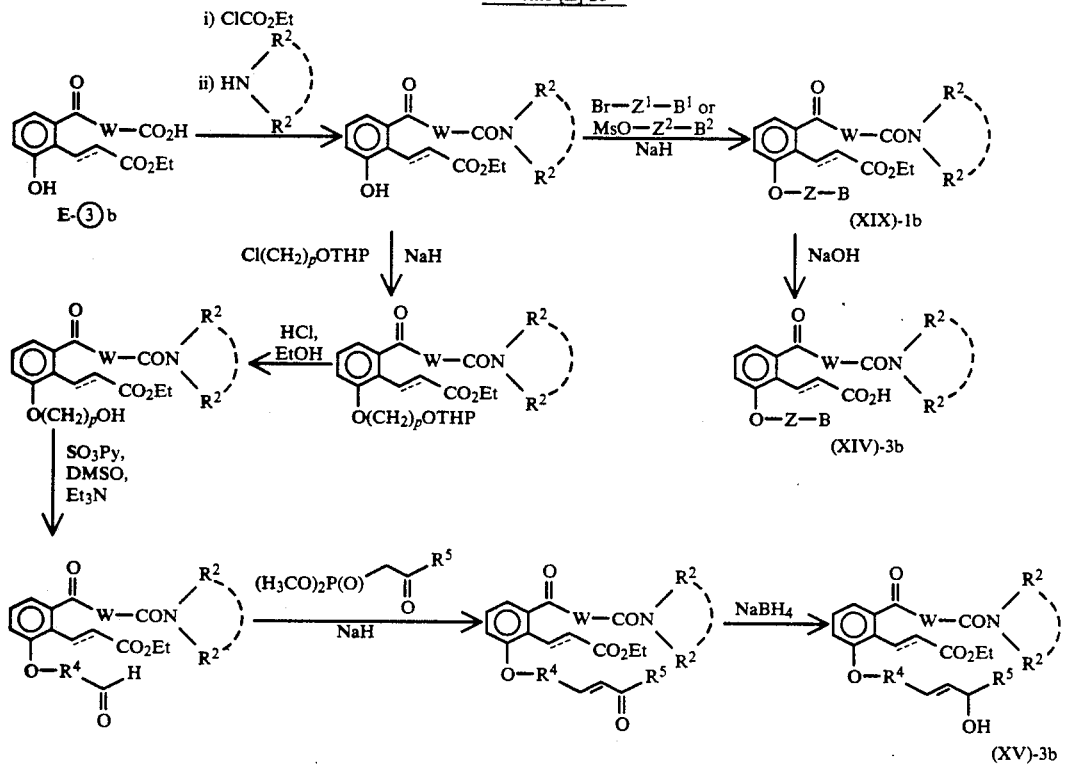

Scheme [E]-3b
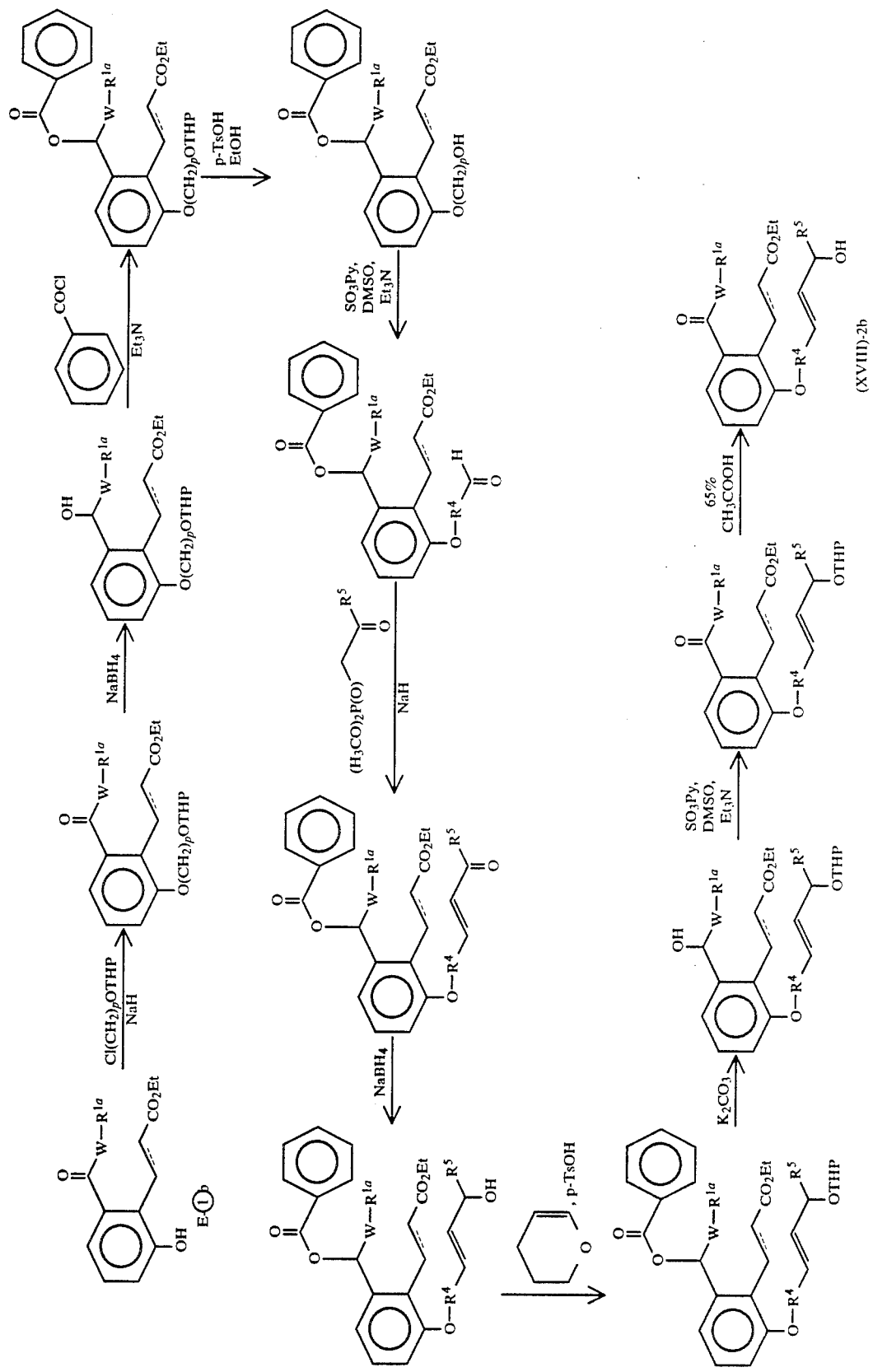

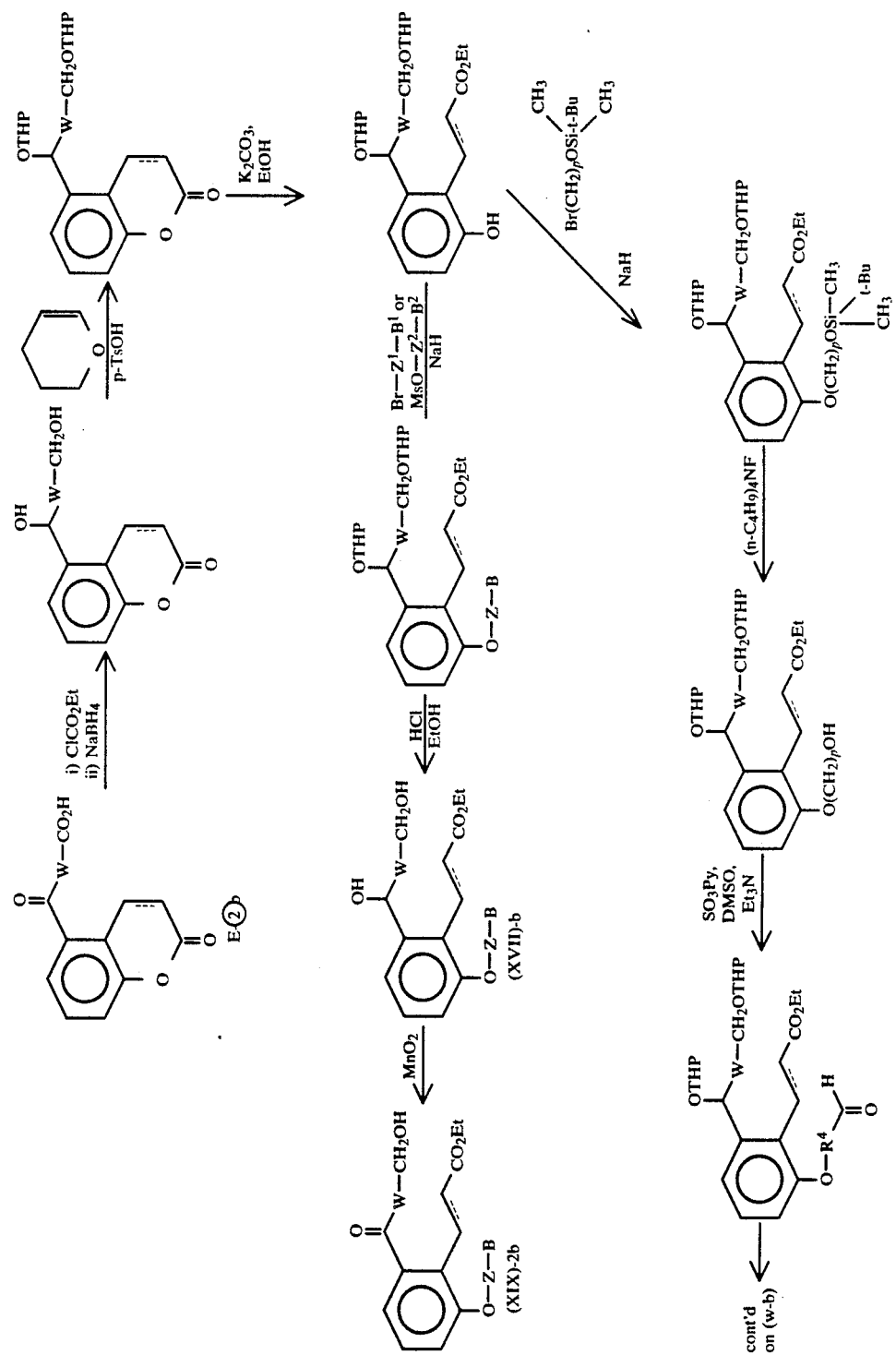

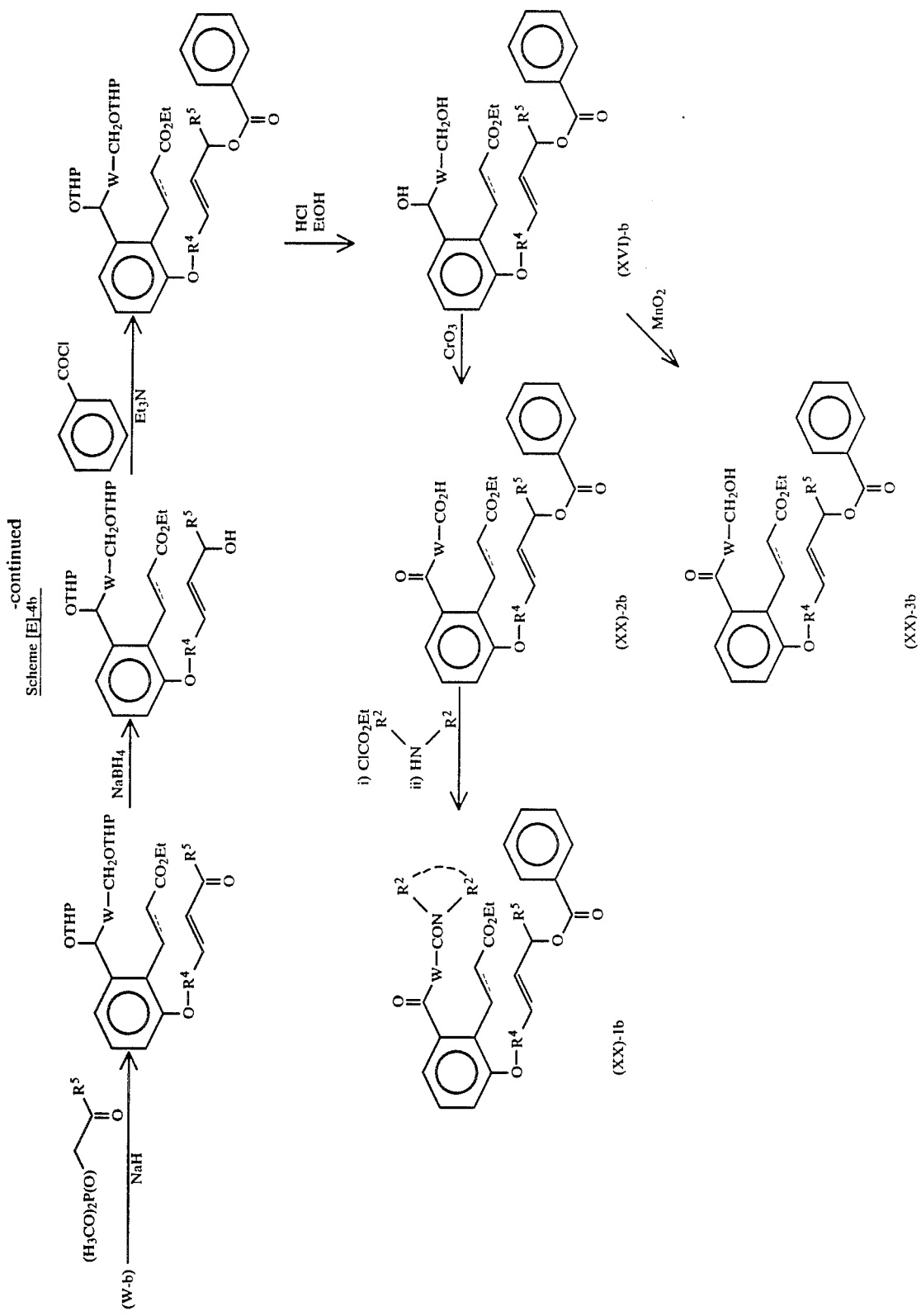

(In schemes, $R^{1a}$ is hydrogen, saturated or unsaturated, 4-7 membered mono-cyclic hetero ring containing one nitrogen as a hetero atom, which ring is unsubstituted or substituted by an oxo group, or C1-4 alkyl; $Z^1$, taken together with $B^1$, is C3-22 alkyl; $Z^2$ is C3-11 alkylene or alkenylene; $B^2$ is the group shown by

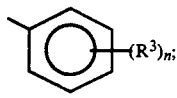

p is 2-8; r is 2 or 3; THP is tetrahydropyran-2-yl; Ms is mesyl; Ac is acetyl; p-TsOH is p-toluenesulfonic acid; SO₃Py is the complex of sulfur trioxide and pyridine; DMSO is dimethyl sulfoxide; Py is pyridine; DCC is 1,3-dicyclohexylcarbodiimide; and the other symbols are the same meaning as described hereinbefore.)

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

STARTING MATERIALS

The starting materials and each reagents in the present invention are known or may be prepared by the known methods.

EFFECT

An antagonism on leukotriene $B_4$ of the compounds of the present invention has been confirmed by the following experimental results.

i) Binding affinity of $^3H$-$LTB_4$ antagonist to human PMNL $LTB_4$ receptor

Human PMNLS ($1 \times 10^7$ cells) were incubated with 1 nM $^3H$-$LTB_4$ in Hanks balanced salt solution (1 ml) at 4° C. for 20 min. in the presence or absence of increasing concentrations of unlabeled $LTB_4$ or various compounds. Free $^3H$-$LTB_4$ was separated from PMNLs-bound ligands by vacuum filteration through Whatman GF/B or C glass fiber filters. The filters were then washed rapidly 4 times with 2.5 ml of the ice-cold phosphate buffered saline. The radioactivity retained in the filter was determined by liquid scintillation counting. Specific binding was defined as the difference between total binding and binding in the presence of 3 μM $LTB_4$ (nonspecific binding). The inhibitory effect of specific $^3H$-$LTB_4$ binding was calculated from the following equation.

The percentage of inhibition
(%) = $100 - (B_1/B_0 \times 100)$ $B_1$: specific $^3H$-$LTB_4$ binding in presence of antagonist
$B_0$: specific $^3H$-$LTB_4$ binding in absence of antagonist
The results are shown in the following table 1.

TABLE 1

| Ex. No. of the compounds | IC₅₀ value (μM) |
| --- | --- |
| 1 | 0.13 |
| 1 (a) | 0.045 |
| 1 (c) | 1.0 |
| 1 (e) | 0.080 |
| 1 (f) | 0.050 |
| 1 (i) | 0.40 |
| 1 (j) | 0.20 |
| 1 (m) | 0.49 |
| 1 (n) | 0.070 |
| 1 (o) | 0.020 |
| 1 (q) | 0.050 |
| 1 (r) | 1.1 |
| 1 (s) | 0.17 |
| 1 (t) | 0.22 |
| 1 (u) | 0.080 |
| 2 | 0.040 |
| 2 (a) | 0.20 |
| 2 (b) | 0.020 |
| 3 | 0.17 |
| 3 (a) | 0.20 |
| 4 | 0.090 |
| 4 (b) | 0.060 |
| 5 | 0.020 |
| 5 (b) | 0.30 |
| 5 (c) | 0.70 |
| 5 (e) | 0.35 |
| 6 | 0.080 |
| 6 (b) | 0.030 |
| 6 (c) | 0.20 |
| 7 (a) | 0.030 |
| 9 | 0.010 |
| 10 | 0.013 |
| 10 (c) | 1.0 |
| 11 | 0.045 |
| 12 | 0.0070 |
| 12 (b) | 0.0060 |
| 13 | 0.045 |
| 14 | 0.070 |
| 16 | 0.090 |
| 18 | 0.025 |
| 19 | 0.030 |
| 20 | 0.0036 |
| 29 | 0.018 |
| 30 | 0.016 |
| 30 (a) | 0.070 |
| 30 (b) | 0.15 |
| 31 | 0.040 |
| 31 (a) | 0.015 |
| 32 | 0.050 |
| 33 | 0.015 |
| 34 | 0.020 |
| 35 | 0.20 |
| 36 | 0.15 |
| 37 | 0.0060 |
| 38 | 0.12 |
| 39 | 0.023 |
| 40 | 0.17 | ii) Inhibition of Human PMNLs aggregation

The purified human PMNLs were suspended in Hank's-0.5% BSA medium (pH 7.4) at $1 \times 10^7$ cells/ml. The PMNLs suspentions (200 μl) were preincubated with varying concentrations of tasted compounds for 3 min. at 37° C. prior to the addition of $10^{-8}M$ splution (10 ml) of $LTB_4$ in Hank's solution. PMNLs aggregation in vitro was performed with a multichannel platelet aggregometer. Aggregation was detected as change in light transmission with an aggregometer.

The results are shown in the following table 2.

TABLE 2

| Ex. No. of the compounds | IC₅₀ value (μM) |
| --- | --- |
| 1 (a) | 3.6 |
| 1 (o) | 3.0 |
| 2 (b) | 7.4 |
| 16 | 7.0 |
| 20 | 2.0 |

TABLE 2-continued

| Ex. No. of the compounds | IC$_{50}$ value ($\mu$M) |
| --- | --- |
| 30 | 0.84 |
| 30 (a) | 1.1 |
| 31 | 6.0 |
| 31 (a) | 1.9 |
| 32 | 5.4 |
| 34 | 0.81 |
| 37 | 1.7 |
| 38 | 4.9 |

The results in the Table 1 Table 2 show that the compounds of the present invention possess an antagonism on leukotrine B$_4$.

TOXICITY

It was confirmed that the toxicity of the compounds, of the present invention were very low. For example, the acute toxicity (LD$_{50}$) of the compounds in Example 30 and 31(a) are 3.9 g/kg and 2.2 g/kg, respectivity, in oral administration and 175 mg/kg and 260 mg/kg, respectivity, in intravenous administration in mouse. Accordingly, it was confirmed that the compounds of the present invention were useful for pharmaceutical agent.

APPLICATION FOR PHARMACEUTICALS

The compounds of the formula (I), of the present invention, are useful for prevention and/or treatment for allergic dermatosis, rheumatism, gout, psoriasis, arthritis, trychophytosis, cardiac infarction etc. In mammals including human beings since they possess an antagonism on LTB$_4$.

For the purpose above described, the compounds, of the formula (I), of the present invention and non-toxic salts thereof may be normally by administered systemically or partially usually by oral or parenteral adminstration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 1 mg and 100 mg, by parenteral administration up to several times per day, or contineous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills capsules, dispersible powders, and granules. Capsules contain hard capsules and soft capsules.

In such compositions, one or more of the active compound(s) is or are, admixed with at least one inert diluent (lactose, mannitol, glucose, hydroxypropyl cellulose, microcrystalline cellulose, starch, polyvinylpyrrolidone, magnesium metasilicate aluminate etc.) The compositions may also comprise, as is normal practice, additional substances other than inert diluents: e.g. lubricating agents (magnesium stearate etc.), disintegrating agents (cellulose calcium glycolate etc.), stabilizing agent (lactose etc.), and assisting agent for dissolving (glutamic acid, asparaginic acid etc.).

The tablets or pills may, if desired, be coated with film of gastric or enteric material (sugar, gelatin, hydroxypropyl cellulose or hydroxypropylmethyl cellulose phthalate etc.), or be coated with more than two films. And further, it may be include capsules of absorbable materials such as gelatin.

Liquid compositions for oral administration include pharmaceutically-acceptable solutions, emulsions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agent etc.), sweetening agents, flavouring agents, perfuming agents and preserving agent.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. Nos. 2,868,691 or 3,095,355 may be used. injections for parenteral administration include sterile aqueous or non-aqueous solutions, suspensions and emulsions. In such compositions, one more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark) etc.).

Injections may comprise aditional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They also be manufactures in the form of sterile solid compositions, for example, by freeze-drying, and which can be dissolved in sterile water or some other sterile diluents for injection immediately before used.

Other compositions for parental administration include liquids for external use, and endermic liniments (ointment etc.), suppositories and pessaries which comprise one or more of the active compound(s) and may be prepared by known methods.

REFERENCE EXAMPLE AND EXAMPLES

The following reference examples and examples are illustrated the present invention, but not limit the present invention.

The solvents in the parentheses show the eluting or developing solvents and the ratios of the solvents used are by volume in chromatographic separations.

Unless otherwise specified, "IR" was measured by the KBr tablet method and "NMR" was measured in a mixture of chloroform-d and methanol-d$_4$, respectively.

The compounds of the formula (I) can be named as derivatives of an alkan(en)oic acid with the numbering of the benzene ring as follows:

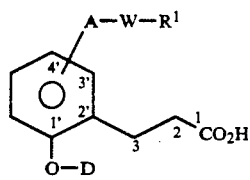

(when Y is ethylene)

The above compound can be called 3-(1-substituted-(3 or 4)-substitutedbenzen-2-yl)propionic acid.

REFERENCE EXAMPLE 1 t-Butyl 3-(2-hydroxy-5-nitrophenyl)-2E-acrylate

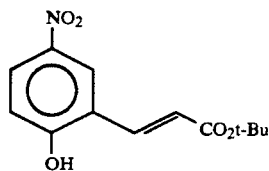

Sodium hydride (content: 62%, 3.3 g) was suspended in tetrahydrofuran (30 ml). The suspension was ice-cooled in an atmosphere of argon gas. A solution of t-butyl diethylphosphonoacetate (20.9 g) in tetrahydrofuran (20 ml) was room temperature. A solution of 2-hydroxy-5-nitrobenzaldehyde (6.6 g) in tetrahydrofuran (20 ml) was gradually added to the mixture often with ice-cooling. The mixture was stirred for 10 min. at room temperature. Acetic acid was gradually added to the mixture until pH of the mixture was down to 5.0. The reaction mixture was gel-filtered with using YMC gel. Moreover the gel was washed with ethyl acetate. A mixture of the filtrate and washings was evaporated. The residue was purified by column chromatography on silica gel (n-hexane:ethyl acetate=2:1→3:2) to give the title compound (10.0 g) having the following physical data.

TLC(n-hexane:ethyl acetate=3:2): Rf 0.40.

REFERENCE EXAMPLE 2 t-Butyl 3-(2-hydroxy-5-aminophenyl)propionate

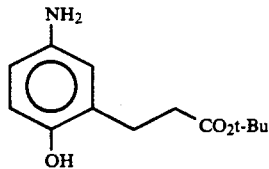

The unsaturated ester (prepared in reference example 1; 8.0 g) was dissolved in ethanol (100 ml). A suspension of 10% Palladium-Carbon (1.0 g) in ethanol (10 ml) was added to the solution. The mixture was stirred for 2 hr. at room temperature under an atmosphere of hydrogen gas. The reaction solution was filtered with using Celite 545. Celite was washed with ethanol. The mixture of the filtrate and washings was evaporated to give the residue (7.1 g), containing the title compound having the following physical data. The residue was used in next reaction without purification.

TLC(n-hexane:ethyl acetate=3:2): Rf 0.22.

REFERENCE EXAMPLE 3 t-Butyl 3-[1-hydroxy-4-(4-methoxycarbonylbutanamido)benzen-2-yl]propionate

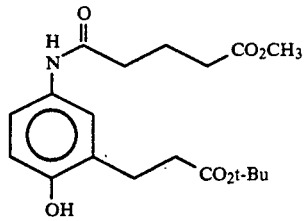

The ester (prepared in reference example 2; 6.4 g) was dissolved in methylene chloride (100 ml). Pyridine (5.0 ml) was added to the solution. 4-methoxycarbonylbutanoyl chloride (3.75 ml) was added to the solution with ice-cooling. The mixture was stirred for 10 min. at room temperature. Ice was added to the reaction mixture. The mixture was extracted with ethyl acetate. The extract was washed with 2N hydrochloric acid, saturated aqueous solution of sodium bicarbonate, followed by saturated brine, dried over anhydrous magnesium sulfate and evaporated. The residue was purified by column chromatography on silica gel (n-hexane:ethyl acetate=2:3→3:8) to give the title compound (9.6 g) having the following physical data.

TLC(n-hexane:ethyl acetate=2:3): Rf 0.51.

REFERENCE EXAMPLE 4 t-Butyl 3-[1-[6-(4-methoxyphenyl)hex-5E-enyl]oxy-4-(4-methoxycarbonylbutanamido)benzen-2-yl]propionate

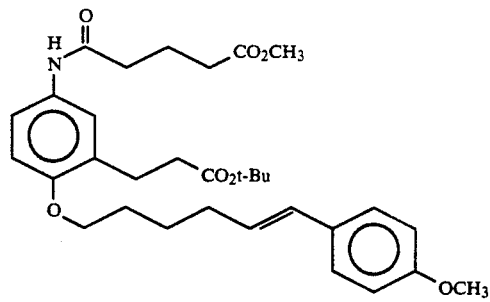

Phenol (580 mg; prepared in reference example 3) and sodium hydride (content: 62%, 62 mg) were dissolved in dried dimethylformamide (2 ml). The solution was stirred at room temperature in an atmosphere of argon gas. A solution of 6-(p-methoxyphenyl)-5E-hexenol methanesulfonate (450 mg) in dried dimethylformamide (1 ml) was added to the solution. The mixture was stirred for 2 hr. at 60° C. The reaction mixture was poured into a mixture of ice and 1N hydrochloric acid (10 ml). The mixture was extracted with ethyl ether-ethyl acetate (1:1). The extract was washed with water, saturated aqueous solution of sodium bicarbonate, followed by brine, dried over anhydrous magnesium sulfate and evaporated. The residue was purified by column chromatography on silica gel (n-hexane:ethyl acetate=3:2) to give the title compound (265 mg) having the following physical data.

TLC(n-hexane:ethyl acetate=1:2): Rf 0.30.

REFERENCE EXAMPLE 5 t-Butyl 3-[1-[6-(4-methoxyphenyl)hex-5E-enyl]oxy-4-(4-carboxylbutanamido)benzen-2-yl]propionate

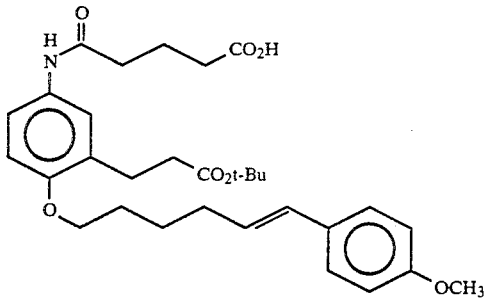

The ester (265 mg; prepared in reference example 4) was dissolved in a mixture of methanol (3 ml) and tetrahydrofuran (2 ml). A 1N aqueous solution of sodium hydroxide (1.0 ml) was added to the solution. The solution was stirred for 3 hr at room temperature. The reaction solution was diluted with water. 1N hydrochloric acid (1.5 ml) was added to the solution. The mixture was extracted with ethyl acetate. The extract was washed with brine, dried over anhydrous magnesium sulfate and evaporated to give the residue contained the title compound having the following physical data. The residue was used in next reaction without purification.

TLC(ethyl acetate): Rf 0.10.

REFERENCE EXAMPLE 6 t-Butyl 3-[1-[6-(4-methoxyphenyl)hex-5E-enyl]oxy-4-(5-oxo-5-morpholinopentanamido)benzen-2-yl]propionate

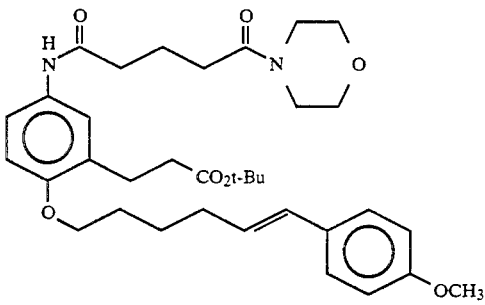

The ester (86 mg; prepared in reference example 5) was dissolved in a mixture of dried tetrahydrofuran (1 ml) and triethylamine (44 μl). Ethyl chloroformate (23 μl) was gradually added to the solution at −10° C. The solution was stirred for 15 min. at −10° C. Morpholine (generally 0.5 ml) was added to the solution. The mixture was stirred for 30 min. at 0° C. and then for 30 min. at room temperature. The reaction mixture was poured to a mixture of ice and 2N hydrochloric acid (10 ml). The mixture was extracted with ethyl acetate. The extract was washed with 2N hydrochloric acid, water, an aqueous solution of sodium bicarbonate, followed by brine, dried over anhydrous magnesium sulfate and evaporated. The residue was purified by column chromatography on silica gel (ethyl acetate) to give the title compound (74 mg) having the following physical data.

TLC(ethyl acetate): Rf 0.10;
MS: m/z 608(M+), 552, 184, 156, 121.

REFERENCE EXAMPLE 7 t-Butyl 3-[1-[6-(4-methoxyphenyl)hex-5E-enyl]oxy-4-(5-hydroxypentanamido)benzen-2-yl]propionate

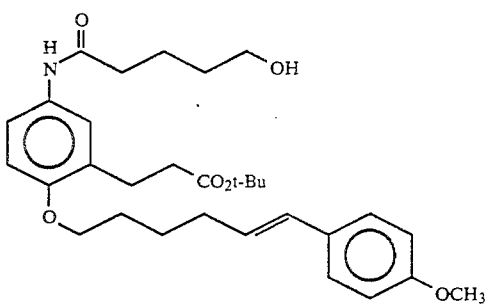

The ester (210 mg; prepared in reference example 5) was dissolved in tetrahydrofuran (2 ml). Triethylamine (56 μl) was added to the solution. Ethyl chloroformate (35 μl) was added to the solution at −10° C. The solution was stirred for 10 min. at −10° C. Sodium borohydride (25 mg) and methanol (0.3 ml) was gradually added to a half quantity of the reaction solution. The solution was stirred for 15 min. The reaction solution was diluted with ethyl acetate. The solution was washed with 1N hydrochloric acid, saturated aqueous solution of sodium bicarbonate, followed by saturated brine, dried over anhydrous magnesium sulfate and evaporated. The residue was purified by column chromatography on silica gel (n-hexane:ethyl acetate=1:2→1:3) to give the title compound (51 mg) having the following physical data.

TLC(n-hexane:ethyl acetate=1:2): Rf 0.32;
MS: m/z 511 (M+), 455.

REFERENCE EXAMPLE 8

1-Hydroxy-2-dimethoxymethyl-4-nitrobenzene

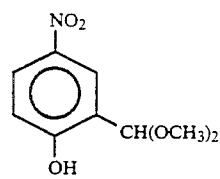

2-Hydroxy-5-nitrobenzaldehyde (3.34 g) was dissolved in methanol (30 ml). Trimethyl orthoformate (20 ml) and then Dowex 50W×8 (H+ form)(generally 2 ml) were added to this solution. The mixture was stirred for 30 min. at room temperature. The resin was removed from the reaction mixture by passing the mixture through an alumina. The filtrate was evaporated to give the title compound (4.0 g) having the following physical data.

TLC(n-hexane:ethyl acetate=2:1): Rf 0.21;
MS: m/z 2/3 (M+), 195, 181.

REFERENCE EXAMPLE 9 t-Butyl 3-[1-hydroxy-4-(4-methoxycarbonylbutanamido)benzen-2-yl]-2E-acrylate

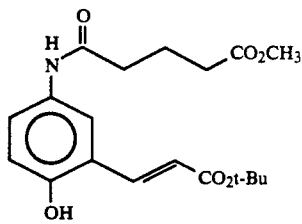

The amide (853 mg), which was obtained with using the acetal (549 mg; prepared in reference example 8) by the same procedure as reference example 2→reference example 3, was dissolved in 5% hydrous acetone (10 ml). p-Toluenesulfonic acid (100 mg) was added to the solution. The solution was stirred for 1 hr. at room temperature. The reaction solution was diluted with ethyl acetate. The solution was washed with saturated aqueous solution of sodium bicarbonate, followed by saturated brine, dried over anhydrous magnesium sulfate and then evaporated. The residue was recrystallized from n-hexane-ethyl acetate (=1:1) to give the corresponding aldehyde (711 mg).

Sodium hydride (content: 62%; 110 mg) was suspended to tetrahydrofuran (10 ml). The suspension was ice-cooled in an atmosphere of argon gas. A solution of t-butyl diethylphosphonoacetate (700 mg) in tetrahydrofuran (15 ml) was added to the suspension. The mixture was stirred for 15 min. at room temperature. A solution of the obtained aldehyde (711 mg) in tetrahydrofuran (10 ml) was gradually added to the mixture occasionally with ice-cooling. The mixture was stirred for 10 min. at room temperature. Acetic acid was gradually added to the reaction mixture until pH of the reaction mixture was down to 5.0. The reaction mixture was gel-filtered with using YMC gel. Moreover the gel was washed with ethyl acetate. A mixture of the filtrate and washings was evaporated. The residue was purified by column chromatography on silica gel (n-hexane:ethyl acetate=1:3) to give the title compound (179 mg) having the following physical data.

TLC(n-hexane:ethyl acetate=1:4): Rf 0.49.

REFERENCE EXAMPLE 10 t-Butyl 3-[1-[5-(tetrahydropyran-2-yl)oxy-n-pentyl]oxy-4-(4-N,N-dimethylaminocarbonylbutanamido)benzen-2-yl]propionate

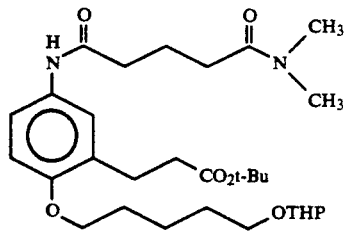

The phenol compound (356 mg), which was obtained with using the ester prepared in reference example 3 by the same procedure as reference examples 5→reference example 6 (with the proviso that dimethylamine was used instead of morpholine), was dissolved in dimethyl formamide (5 ml). The solution was ice-cooled. Sodium hydride (content: 62%; 22.6 mg) was added to the solution. This solution was stirred for 15 minutes at room temperature. A solution of 1-chloro-5-(tetrahydropyran-2-yl)oxy-n-pentane (206 mg) in dimethyl formamide (1 ml) was added to the reaction mixture. The mixture was stirred at 75° C. all night. The reaction mixture was diluted with ether. The mixture was washed with water, dried over anhydrous magnesium sulfate and evaporated. The residue was purified by column chromatography on silica gel (chloroform:methanol=20:1) to give the title compound (336 mg) having the following physical data.

MS: m/z 548 (M+), 464.

REFERENCE EXAMPLE 11

3-[1-(5-formyloxy-n-pentyl)oxy-4-(4-N,N-dimethylaminocarbonylbutanamido)benzen-2-yl]propionic acid

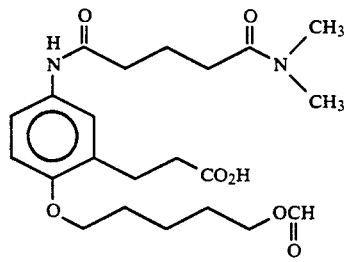

The ester (336 mg) prepared in reference example 10 was dissolved in formic acid (5 ml). The solution was stirred for 1 hr. at room temperature and then for 1 hr. at 45° C. The reaction solution was evaporated to give the residue contained the title compound having the following physical data. The residue was used in next reaction without purification.

TLC(chloroform:methanol=10:1): Rf 0.33.

REFERENCE EXAMPLE 12

Methyl 3-[1-(5-formyloxy-n-pentyl)oxy-4-(4-N,N-dimethylaminocarbonylbutanamido)benzen-2yl]propionate

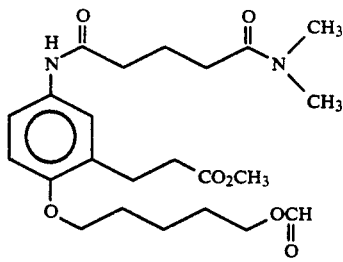

The residue which contained the carboxylic acid prepared in reference example 11 was dissolved in ethyl acetate (2 ml). A solution of diazomethane in ether was added to the solution until the reaction mixture was slightly tinged with yellow. The reaction mixture was evaporated. The residue was purified by column chromatography on silica gel (chloroform:methanol=20:1) to give the title compound (227 mg) having the following physical data.

MS: m/z 450 (M+), 406.

REFERENCE EXAMPLE 13

Methyl 3-[1-(5-hydroxy-n-pentyl)oxy-4-(4-N,N-dimethylaminocarbonylbutanamido)benzen-2-yl]propionate

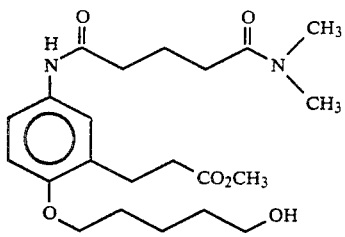

The ester (220 mg) prepared in reference example 12 was dissolved in methanol (2 ml). Potassium carbonate (82.8 mg) was added to the solution. The mixture was stirred for 2 hr. at room temperature. The mixture was acidified with 1N hydrochloric acid. The mixture was extracted with ethyl acetate. The extract was washed with water, dried over anhydrous magnesium sulfate and then evaporated. The residue was purified by column chromatography on silica gel (chloroform:methanol=20:1) to give the title compound (176 mg) having the following physical data.

MS: m/z 442(M+), 281.

REFERENCE EXAMPLE 14

Methyl 3-[1-(4-formyl-n-butyl)oxy-4-(4-N,N-dimethylaminocarbonylbutanamido)benzen-2-yl]propionate

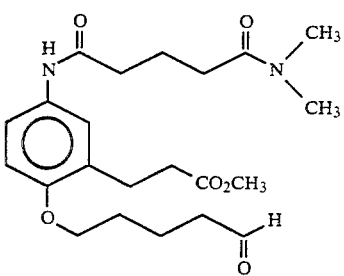

The alcohol (173 mg) prepared in reference example 13 was dissolved in dimethyl sulfoxide (2 ml). Triethylamine (207.5 mg) and sulfur trioxide-pyridine complex (195.6 mg) were added to the solution. The mixture was stirred for 30 min. at room temperature. The reaction solution was acidified with 1N hydrocholoric acid. The solution was extracted with ether. The extract was washed with water, dried over anhydrous magnesium sulfate and then evaporated. The residue was purified by colomn chromatography on silica gel (chloroform:methanol=20:1) to give the title compound (61 mg) having the following physical data.

NMR: δ9.80 (1H, t, J=1 Hz), 8.10 (1H, s), 7.42 (1H, d, d, J=8 Hz, J=1 Hz), 7.23 (1H, d, J=1 Hz), 6.75 (1H, d, J=8 Hz), 4.00–3.90 (2H, m), 3.70 (3H, s), 3.03 (3H, s), 2.99 (3H, s), 2.92 (2H, t, J=7 Hz), 2.65–2.40 (6H, m), 2.15–1.95 (2H, m), 1.90–1.45 (4H, m).

REFERENCE EXAMPLE 15

Methyl 3-[1-(5E-7-oxopentadecenyl)oxy-4-(4-dimethylaminocarbonylbutylamido)benzen-2-yl]propionate

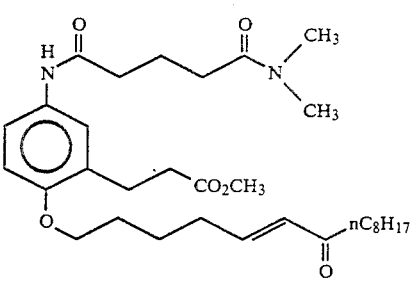

A solution of dimetyl 2-oxodecylphosphonate (132 mg) in tetrahydrofuran (1 ml) was added to a suspension of sodium hydride (content: 62%, 7.75 mg) in tetrahydrofuran (3 ml). A solution of the aldehyde (59 mg) prepared in reference example 14 in tetrahydrofuran (2 ml) was added to the mixture. The solution was stirred for 30 min. at room temperature and then for 1 hr. at 60° C. The reaction solution was acidified with acetic acid. The solution was gel-filtered. The filtrate was evaporated. The residue was purified by column chromatography on silica gel (ethyl acetate:methanol=20:1) to give the title compound (50 mg) having the following physical data.

MS: m/z 558 (M+), 417.

REFERENCE EXAMPLE 16

Methyl 3-[1-(5E-7-hydroxypentadecenyl)oxy-4-(4-dimethylaminocarbonylbutanamido)benzen-2-yl]propionate

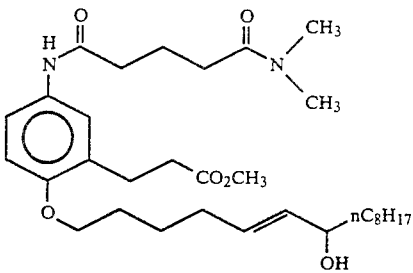

The compound (48 mg) prepared in reference example 15 and cerium chloride.7H₂O (37.3 mg) were dissolved in methanol (1 ml). Sodium borohydride (3.25 mg) in limited amounts was added to the solution. The mixture was stirred for 30 min. at room temperature. The reaction solution was acidified with acetic acid. The solution was extracted with ethyl acetate. The extract was washed with water, dried over anhydrous magnesium sulfate and evaporated. The residue was purified by column chromatography on silica gel (chloroform:methanol=20:1) to give the title compound (46 mg) having the following physical data.

Ms: m/z 560, 542.

REFERENCE EXAMPLE 17 t-Butyl 3-(1-hydroxy-4-trifluoroacetoamidobenzen-2-yl)propionate

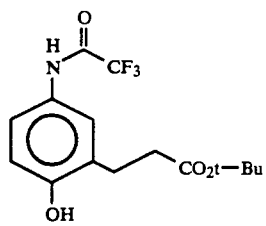

t-Butyl 3-(1-hydroxy-4-aminobenzen-2-yl)propionate was disslolved in a mixture of tetrahydrofuran (100 ml) and triethylamine (7.1 ml). Anhydrous trifluoroacetic acid (6.0 ml) was added to the solution at 0° C. in an atmosphere of argon gas. The solution was stirred for 2 hr. at 0° C. The reaction solution was poured into a mixture of ice and 1N hydrochloric acid (100 ml). The reaction mixture was extracted with ethyl acetate (300 ml). The extract was washed with water, saturated aqueous solution of sodium bicarbonate, followed by brine, dried over anhydrous magnesium sulfate and evaporated. The residue was recrystallized from a mixture of ethyl acetate-n-hexane (1:5) to give the title compound having the following physical data.

TLC(ethyl acetate:n-hexane = 1:2): Rf 0.30;
MS: m/z 333 (M+), 277, 259, 231, 217.

REFERENCE EXAMPLE 18 t-Butyl 3-[1-[6-(4-methoxyphenyl)hex-5E-enyl]oxy-4-aminobenzen-2-yl]propionate

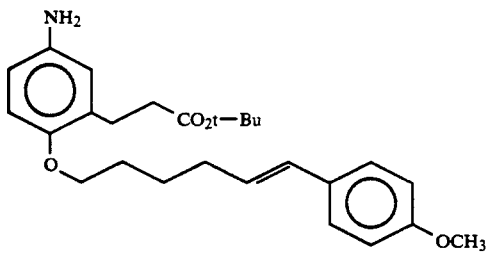

The trifluoroacetoamide (5.3 g), which was prepared with using the compound prepared in reference example 17 by the same procedure as reference example 4 was dissolved in a mixture of methanol (30 ml) and water (5 ml). Anhydrous potassium carbonate (2.8 g) was added to the solution. The mixture was stirred at room temperature a whole day and night. Water (100 ml) was added to the reaction mixture. The reaction mixture was extracted with ethyl acetate (200 ml×2). The extract was washed with brine, dried over anhydrous magnesium sulfate and then evaporated. The residue was purified by column chromatography on silica gel (ethyl acetate:n-hexane = 2:3) to give the title compound (3.5 g) having the following physical data.

TLC(ethyl acetate:n-hexane = 1:2): Rf 0.20;
MS: m/z 425 (M+), 369, 189, 181, 163, 147, 121.

REFERENCE EXAMPLE 19 t-Butyl 3-[1-[6-(4-methoxyphenyl)hex-5E-enyl]oxy-4-(N-acetyl-N-mesylaminobenzen-2-yl]propionate

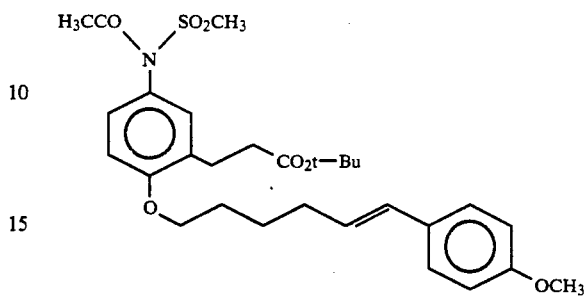

The ester (176 mg) prepared in reference example 18 was dissolved in a mixture of methylene chloride (3 ml) and triethylamine (0.29 ml). Methanesulfonyl chloride (35 μl) was added to the solution at 0° C. The solution was stirred for 30 min. Acetyl chloride (0.12 ml) was added to the reaction solution. The mixture was refluxed for 10 min. The reaction mixture was poured into a mixture of ice and 1N hydrochloric acid (10 ml). The reaction mixture was extracted with ethyl acetate (80 ml). The extract was washed with water, followed by brine, dried over anhydrous magnesium sulfate and evaporated. The residue was purified by column chromatography on silica gel (ethyl acetate:n-hexane = 1:2) to give the title compound (200 mg) having the following physical data.

TLC(ethyl acetate:n-hexane = 1:1): Rf 0.40;
MS: m/z 545 (M+), 489, 447, 189, 147, 121.

REFERENCE EXAMPLE 20 t-Butyl 3-[1-[6-(4-methoxyphenyl)hex-5E-enyl]oxy-4-dimesylaminobenzene-2-yl]propionate

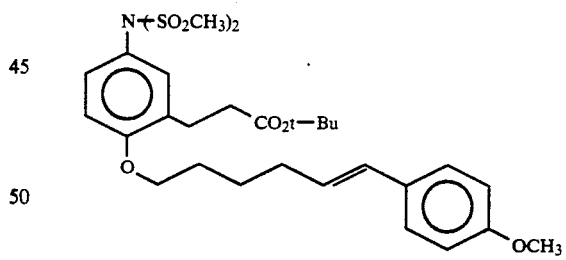

The ester (158 mg) prepared in reference example 18 was dissolved in a mixture of methylene chloride (3 ml) and triethylamine (0.15 ml). Methanesulfonyl chloride (72 μl) was added to the solution at room temperature. The solution was stirred for 1 hr. The reaction solution was poured into a mixture of ice and 1N hydrochloric acid (10 ml). The reaction mixture was extracted with ethyl acetate (80 ml). The extract was washed with water, followed by brine, dried over anhydrous mangesium sulfate and then evaporated. The residue was purifed by column chromatography on silica gel (ethyl acetate:n-hexane = 1:2) to give the title compound (170 mg) having the following physical data.

TLC(ethyl acetate:n-hexane = 1:2): Rf 0.25;
MS: m/z 581 (M+), 525, 189, 147, 121.

REFERENCE EXAMPLE 21 t-Butyl 3-[1-[6-(4-methoxyphenyl)hex-5E-enyl]oxy-4-phthalimidobenzen-2-yl]propionate

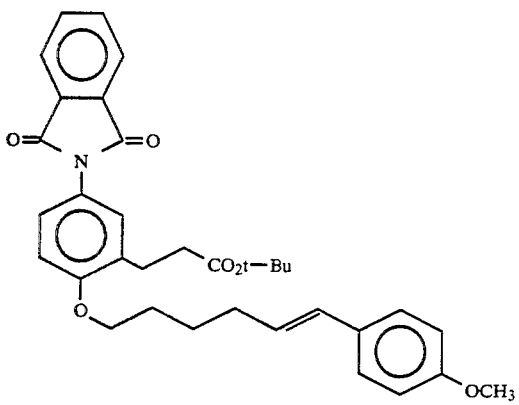

The ester (176 mg) prepared in reference example 18 was dissolved in chloroform (5 ml). Anhydrous phthalic acid (120 mg) was added to the solution. The solution was refluxed for 24 hr. The reaction solution was evaporated. The residue was purified by column chromatography on silica gel (methylene chloride→methylene chloride:ethyl acetate=10:1) to give the title compound (130 mg) having the following physical data.

TLC(ethyl acetate:n-hexane=1:4): Rf 0.20;
MS: mz 555 (M+), 499, 311, 293, 189, 147, 121.

REFERENCE EXAMPLE 22 t-Butyl 3-[1-[6-(4-methoxyphenyl)hex-5E-enyl]oxy-4-(perhydro-1,2-thiazin-1,1,3-trione-2-yl)benzene-2-yl]propionate

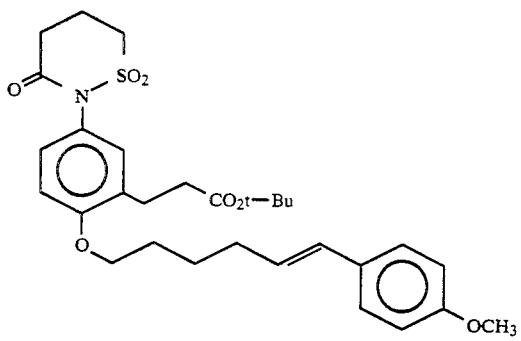

The t-butyl ester (950 mg), which was prepared with using the ester prepared in reference example 18 by the same procedure as reference example 3 (with the proviso that the corresponding sulfonyl chloride was used instead of 4-methoxycarbonylbutanoyl chloride)→reference example 5, was dissolved in a mixture of tetrahydrofuran (15 ml) and triethylamine (0.69 ml). Ethyl chloroformate (0.24 ml) was gradually added to the solution at 15° C. in an atmosphere of argon gas. The solution was stirred for 10 min at −15° C. and then for 30 min at 0° C. The reaction solution was poured into a mixture of ice and 1N hydrochloric acid (20 ml). The reaction mixture was extracted with ethyl acetate (100 ml). The extract was washed with water, saturated aqueous solution of sodium bicarbonate, followed by brine, dried over anhydrous magnesium sulfate and evaporated. The residue was purified by column chromatography on silica gel (ethyl acetate:n-hexane=2:1) to give the title compound (710 mg) having the following physical data.

TLC(ethyl acetate:n-hexane=2:1): Rf 0.60;
MS: m/z 557 (M+), 501, 187, 121.

REFERENCE EXAMPLE 23 t-Butyl 3-[1-(5-hydroxy-n-pentyl)oxy-4-trifluoroacetoamidobenzen-2-yl]propionate

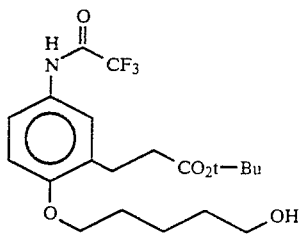

The ester (2.56 g), which was prepared with using the ester prepared in reference example 17 by the same procedure as reference example 10, was dissolved in ethanol. p-Toluenesulfonic acid (15 mg) was added to the solution. The solution was stirred for 40 min at room temperature. Few drops of triethylamine was added to the reaction solution. The reaction mixture was evaporated. The residue was purified by column chromatography on silica gel (n-hexane:ethyl acetate=2:1) to give the title compound (1.93 g) having the following physical data.

TLC(ethyl acetate:n-hexane=1:2): Rf 0.10;
MS: m/z 419 (M+), 363, 277, 259, 231.

REFERENCE EXAMPLE 24

3(1,4-dimethoxybenzene-2-yl)prop-2E-enoic acid

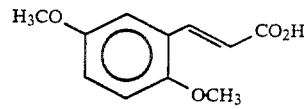

2,5-Dimethoxybenzaldehyde (1.7 g) was dissolved in pyridine (10 ml). Piperidine (0.2 ml) and malonic acid (2.0 g) were added to the solution. The solution was stirred for 1 hour at 85° C. and then for 3 hr. at 110° C. The solution was cooled. Water (80 ml) was added to the solution. Conc. hydrochloric acid was added to the solution until pH of the solution was down to about 2. The crystals were deposited. The crystals were separated from the solution by filtration, washed with water and dried to give the title compound (1.97 g) having the following physical data.

NMR: δ8.08 (1H, d, J=16 Hz), 7.08 (1H, d, J=2 Hz), 6.98-6.83 (2H,m), 6.53 (1H, d, J=16 Hz), 3.85 (3H, s), 3.80 (3H, s).

REFERENCE EXAMPLE 25

6-Hydroxycoumarin

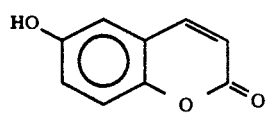

The carboxylic acid (1.97 g; prepared in reference example 24) and pyridine hydrochloride (12 g) were heated to 180°-190° C. The mixture was reacted for 3.5 hr. The reaction mixture was cooled and then dissolved in water. The solution was extracted with ethyl acetate. The extract was washed with water, dried over anhydrous magnesium sulfate and then evaporated. The residue was purified by column chromatography on silica gel (n-hexane:ethyl acetate=3:1→1:1). The obtained crystals were washed with a mixture of n-hexane and ethyl acetate (3:1→1:1) to give the title compound (751 mg) having the following physical data.

NMR: δ7.67 (1H, d, J=10 Hz), 7.20 (1H, d, J=8 Hz), 7.05 (1H, dd, J=8 Hz, J=1 Hz), 6.90 (1H, d, J=1 Hz), 6.40 (1H, d, J=10 Hz).

REFERENCE EXAMPLE 26

6-(4-ethoxycarbonylbutyl)oxycoumarin

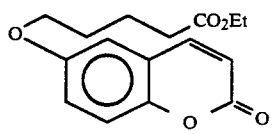

6-Hydroxycoumarin (405 mg; prepared in reference example 25) was dissolved in dry dimethylformamide (6 ml). Sodium hydride (60 mg) was added to the solution. The mixture was reacted for 15 min. Ethyl 5-bromopentanoate (0.48 ml) was added dropwise to the reaction solution. The mixture was stirred for 1 hr at 60° C. Ice-water was added to the reaction solution. The mixture was acidified with 1N hydrochloric acid. The mixture was extracted with ether. The extract was washed with water, dried anhydrous magnesium sulfate and then evaporated. The residue was purified by column chromatography on silica gel (n-hexane:ethyl acetate=4:1→2:1) to give the title compound (398 mg) having the following physical data.

NMR: 7.75 (1H, d, J=10 Hz), 7.25 (1H, d, J=8 Hz), 7.10 (1H, dd, J=8 Hz, J=1 Hz), 6.90 (1H, d, J=1 Hz), 6.43 (1H, d, J=10 Hz).

REFERENCE EXAMPLE 27

Ethyl 3-[1-hydroxy-4-(4-ethoxycarbonylbutoxy)benzen-2-yl]prop-2E-enoate

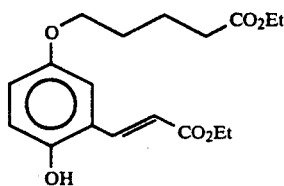

Sodium hydride (content: 62%; 60 mg) was gradually added to anhydrous ethanol (10 ml) and dissolved. A solution of the ester (314 mg; prepared in reference example 26) in anhydrous ethanol (1 ml) was added to the solution. The mixture was stirred for 4 hr. at 70° C. and then for 30 min at 80° C. Glacial acetic acid (210 mg) was added to the reaction solution with ice-cooling to stop the reaction. The solvent was removed from the reaction solution under reduced pressure. The residue was diluted with ether. The mixture was washed with water. Aqueous layer was removed. Ethereal layer was dried over anhydrous magnesium sulfate and then evaporated. The residue was purified by column chromatography on silica gel (n-hexane:ethyl acetate=2:1) to give the title compound (122 mg) having the following physical data.

TLC(n-hexane:ethyl acetate=2:1): Rf 0.20.

REFERENCE EXAMPLE 28

Methyl 3-[1-methoxy-4-(1-oxo-4-methoxycarbonyl-n-butyl)benzen-2-yl]propionate

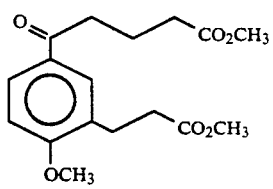

Anhydrous aluminium chloride (22.2 g) was suspended in methylene chloride (150 ml). The suspension was cooled to 0° C. Methyl 4-(chloroformyl)butylate (10.0 g) was added to the suspension at 0° C. The methyl ester (10.5 g), which was prepared with using 3-(1-methoxybenzen-2-yl)propanoic acid (10.0 g) by the same procedure as reference example 12, was added to the prepared suspension. The suspension was stirred for 30 min. The reaction solution was poured into a mixture of ice and 2N hydrochloric acid. The reaction mixture was extracted with ethyl acetate. The extract was washed with saturated brine, dried over anhydrous magnesium sulfate and then evaporated. The residue was purified by column chromatography on silica gel (n-hexane:ethyl acetate=2:1→3:2) to give the title compound (13.6 g) having the following physical data.

TLC(n-hexane:ethyl acetate=2:1): Rf 0.33;
MS: m/z 322 (M+), 291.

REFERENCE EXAMPLE 29

3-[1-hydroxy-4-(4-carboxyl-n-butyl)benzen-2yl]propionic acid

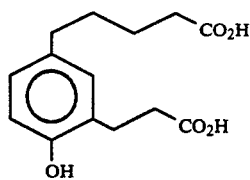

An ester (1.0 g), which was prepared with using the ester prepared in reference example 28 by the same procedure as reference example 16, was dissolved in dimethylsulfoxide (2 ml). The solution was stirred for 30 min. at 180° C. The reaction solution was diluted with ether. The mixture was washed with 1N hydrochloric acid, followed by saturated brine, dried over anhydrous magnesium sulfate and then evaporated. The residue was purified by column chromatography on silica gel (n-hexane:ethyl acetate=3:1) to give an olefin compound. The olefin compound (848 mg) was dissolved in ethanol (15 ml). A suspension of 10% palladium-carbon (100 mg) in ethanol (5 ml) was added to the solution. The mixture was stirred for 1.5 hr. at room temperature in an atomsphere of hydrogen gas. The catalyst was removed from the reaction solution by Celite 545. The reaction solution was evaporated to give a reduced compound (798 mg). Pyridinium chloride (15 g) was added to the reduced compound (1.66 g). The mixture was stirred for 4 hr. at 180° C. A temperature of the reaction mixture was down to room temperature. The mixture was dissolved in 1N hydrochloric acid. The reaction mixture was extracted with ethyl acetate. The extract was washed with saturated brine, dried over anhydrous magnesium sulfate and evaporated to give the residue contained the title compound having the following physical data. The residue was used in next reaction without purification.

TLC(ethyl acetate): Rf 0.39;
MS: m/z 266 (M+), 248, 161.

REFERENCE EXAMPLE 30

5-(3,4-dihydrocoumarin-6-yl)valeric acid

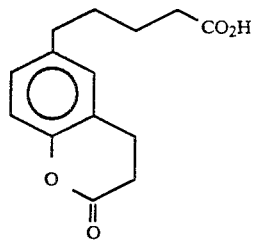

The dicarboxylic acid (1.72 g) prepared in reference example 29 was dissolved in a mixture of benzene (100 ml) and tetrahydrofuran (2 ml). Dowex 50W×8 (H+ form)(about 10 ml) was added to the solution. The mixture was refluxed for 2 hr. The reaction solution was filtered to remove Dowex. The filtrate was evaporated to give the residue (1.28 g) contained the title compound having the following physical data. The residue was used in next reaction without purification.

TLC(chloroform:methanol=10:1): Rf 0.49;
MS: m/z 248 (M+), 130.

REFERENCE EXAMPLE 31

Ethyl 3-[1-hydroxy-4-dimethylaminoccarbonyl-n-butyl)benzen-2-yl]propionate

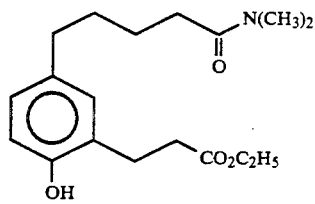

A carboxylic acid, which was prepared with using the lactone prepared in reference example 30 by the same procedure as reference example 6 (with the proviso that dimethylamine was used instead of morpholine)→example 5, was dissolved in ethanol (5 ml). Conc. sulfuric acid (about 0.1 ml) was added dropwise to the solution. The solution was stirred for 1.5 hr. at 60° C. The reaction solution was diluted with ethyl acetate. The diluted solution was washed with saturated aqueous solution of sodium bicarbonate, followed by saturated brine, dried over anhydrous magnesium sulfate and evaporated. the residue was purified by column chromatography on silica gel (ethyl acetate) to give the title compound (1.5 g) having the following physical data.

TLC(ethyl acetate): Rf 0.58;
MS: m/z 307 (M+), 276.

REFERENCE EXAMPLE 32

3-[1-hydroxy-4-(1-oxo-4-carboxylbutyl)benzen-2-yl]propionic acid

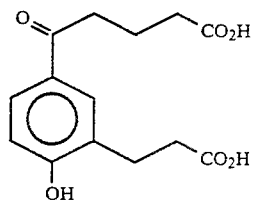

A dicarboxylic acid (6.6 g), which was prepared with using the ester prepared in reference example 28 by the same procedure as reference example 5, was dissolved in acetic acid (10 ml). 47% hydrobromic acid (30 ml) was added to the solution. The mixture was refluxed all night. The reaction solution was evaporated. The residue waas diluted with ethyl acetate. The diluted solution was washed with saturated brine, dried over magnesium sulfate and then evaporate. The residue was recrystallized from ethyl acetate to give the title compound (915 mg) having the following physical data.

MS: m/z 280 (M+), 262.

REFERENCE EXAMPLE 33

Anhydrous 4-methoxyphthalide

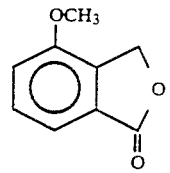

Anhydrous 2-methoxyphthalic acid (640 mg), which was prepared with using anhydrous 2-hydroxyphthalic acid by the same procedure as reference example 12, was suspended in tetrahydrdofuran (20 ml). Acetic acid (430 mg) and sodium borohydride (135 mg) were added to the suspension. The mixture was stirred for 30 min. at room temperature and for 2 hr. at 50° C. The reaction solution was cooled. 1N hydrochloric acid (7 ml) was added to the cooled solution. The solution was stirred for 15 min. The reaction solution was evaporated. The residue was purified by column chromatography on silica gel (n-hexane:ethyl acetate=2:1→1:1) to give the title compound (314 mg) having the following phsysical data.

TLC(n-hexane:ethyl acetate=1:1): Rf 0.67.

REFERENCE EXAMPLE 34

1-hydroxy-4-methoxy-1,3-dihydrobenzo[c]furan

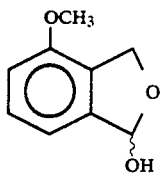

The phthalide (346 mg) prepared in reference example 33 was dissolved in toluene (20 ml). The solution was cooled to −78° C. A 1.76N solution of diisobutylaluminum hydride (DIBAL) in toluene (1.43 ml) was added dropwise to the cooled solution. The mixture was stirred for 30 min. at −78° C. Methanol (0.2 ml) was added to the reaction solution to decompose the excess DIBAL. Water was added to the reaction solution. A temperature of the solution was up to room temperature. The solution was stirred for 30 min. at room temperature. The reaction solution was dried over anhydrous sodium sulfate, washed with ethyl acetate and evaporated to give the residue contained the title compound having the following physical data. The residue was used in next reaction without purification.

TLC(n-hexane:ethyl acetate=1:1): Rf 0.56.

REFERENCE EXAMPLE 35

Methyl 5E-6-(2-hydroxymethyl-3-methoxyphenyl)hexenoate

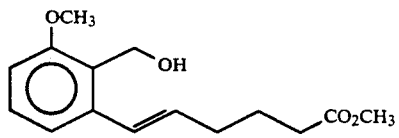

(4-Carboxybutyl)triphenylphosphonium bromide (2.79 g) was suspended in toluene (30 ml). Potassium t-butoxide (1.34 g) was added to the suspension. The suspension was stirred for 15 min. at 80° C. A solution of the compound (348 mg) prepared in reference example 34 in toluene (10 ml) was added dropwise to the reaction solution. The solution was stirred for 1.5 hours at 80° C. The reaction mixture was cooled and then acidified by adding 1N hydrochloric acid. The solution was extracted with ethyl acetate. The extract was washed with water, dried over anhydrous magnesium sulfate and evaporated. The residue was purified by column chromatography (n-hexane:ethyl acetate=1:1) to give the title compound (270 mg) having the following physical data.

NMR: δ7.12 (1H, t, J=8 Hz), 7.03 (1H, d, J=8 Hz), 6.85–6.70 (2H, m), 6.05 (1H, d, t, J=16 Hz, J=6 Hz), 4.80 (2H, s), 3.90 (3H, s).

MS: m/z 250 (M+), 232.

REFERENCE EXAMPLE 36

Ethyl 6-[2-(2-ethoxycarbonylethyl)-3-hydroxyphenyl]hexanoate

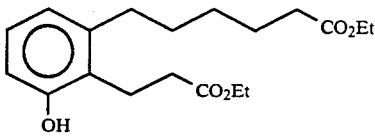

Methyl 6-[2-(2-ethoxycarbonylethyl)-3-metoxyphenyl]hexanoate, which was prepared with using the compound prepared in reference example 35 by the same procedure as reference example 12→reference example 2→reference example 14→reference example 1 (with the proviso that ethyl diethylphosphonoacetate was used instead of t-butyl diethylphosphonoacetate)→reference example 2, and pyridine hydrochloride were reacted for 2 hr. at 190° C. The reaction mixture was cooled. 1N hydrochloric acid was added to the mixture. The mixture was extracted with ethyl acetate. The extract was dried over anhydrous magnesium sulfate and then evaporated. The residue was dissolved in a saturated solution of hydrogen chloride in ethanol (5 ml). The solution was stirred for 30 min. The reaction solution was evaporated. The residue was purified by column chromatography on silica gel (n-hexane:ethyl acetate=2:1) to give the title compound (87.3 mg) having the following physical data.

NMR: δ7.13 (1H, d, J=8 Hz), 7.03 (1H, t, J=8 Hz), 6.75 (2H, d, J=8 Hz), 4.20–4.05 (4H, m), 2.93 (2H, t, J=7 Hz), 2.70–2.50 (4H, m), 2.30 (2H, t, J=7 Hz), 1.75–1.30 (6H, m), 1.30–1.20 (6H, m).

MS: m/z 336 (M+), 291, 262.

REFERENCE EXAMPLE 37

Methyl 2E-3-(2-hydroxymethyl-6-methoxyphenyl)acrylate

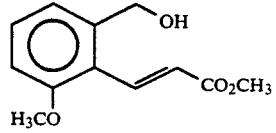

1-Hydroxy-7-methoxy-1,3-dihgydrobenzo[c]furan (1.08 g), which was prepared with using 7-methoxyphthalide which was synthesized with using 3-methoxybenzaldehyde by the method described in Journal of Organic Chemistry, 1980, 45, 1835–1838, was dissolved in chloroform (20 ml). Methyl (triphenylphosphoranylidene)acetate (2.68 g) was added to the solution. The mixture was stirred for 40 min. at 50° C. A temperature of the reaction mixture was down to room temperature. The reaction solution was purified by column chromatography on silica gel (n-hexane:ethyl acetate=2:1) to give the title compound (1.25 g) having the following physical data.

NMR: δ8.93 (1H, d, J=16 Hz), 7.30 (1H, t, J=8 Hz), 7.07 (1H, d, J=8 Hz), 6.90 (1H, d, J=8 Hz), 6.70 (1H, d, J=16 Hz), 4.80 (2H, d, J=5 Hz), 3.87 (3H, s), 3.81 (3H, s).

MS: m/z 222 (M+), 204, 191.

REFERENCE EXAMPLE 38

Methyl 3-[2-(1-hydroxyhex-5-enyl)-6-methoxyphenyl]propionate

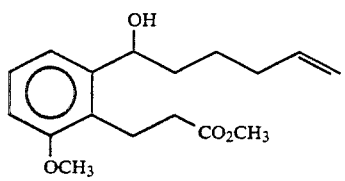

5-Bromo-1-penten (596 mg) was added dropwise to a solution of magnesium (96 mg) in diethyl ether (2 ml). Diethyl ether (4 ml) was added to the solution to prepare Grignard reagent. A solution of methyl 3-(2-formyl-6-methoxyphenyl)propionate (444 mg), which was prepared with using the ester prepared in reference example 37 by the same procedure as reference example 2→reference example 14, in diethyl ether (1 ml) was ice-cooled. The grignard reagent (3.3 ml) prepared beforehand was added dropwise to the cooled solution. The mixture was stirred for 1.5 hr. with ice-cooling. The reaction mixture was added to a saturated aqueous solution of ammonium chloride. The mixture was extracted with diethyl ether. The extract was washed with water, dried over anhydrous magnesium sulfate and evaporated. The residue was purified by column chromatography on silica gel (n-hexane:ethyl acetate=4:1) to give the title compound (497.5 mg) having the following physical data.

NMR: δ7.23 (1H, t, J=8 Hz), 7.10 (1H, d, J=8 Hz), 6.78 (1H, d J=8 Hz), 6.90–6.70 (1H, m), 5.06–4.90 (3H, m), 3.85 (3H, s), 3.67 (3H, s), 3.05–2.95 (2H, m), 2.65–2.52 (2H, m), 2.15–2.05 (2H, m), 1.90–1.35 (4H, m).

MS: m/z 292 (M+), 260, 243.

REFERENCE EXAMPLE 39

Methyl 3-[2-(1,6-dihydroxyhexyl)-6-methoxyphenyl]propionate

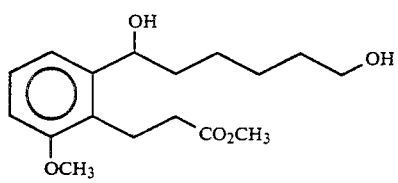

A solution of the ester (494.5 mg) prepared in reference example 38 in tetrahydrofuran (6.77 ml) was ice-cooled. A 1N solution (6.77 ml) of diborane in tetrahydrofuran was added dropwise to the solution. The mixture was stirred for 30 min at room temperature. The reaction solution was ice-cooled. Water was added dropwise to the solution to decompose excess diborane. A 1N aqueous solution of sodium hydroxide and then 30% hydrogen peroxide (6.77 ml) were added dropwised to the reaction mixture. The mixture was stirred for 30 min. at room temperature and reacted by the same procedure as reference example 12. The reaction solution was poured into a 1N solution of hydrochloric acid in diethyl ether (100 ml). The mixture was extracted with diethyl ether. The extract was washed with water, dried over anhydrous magnesium sulfate and then evaporated. The residue was purified by column chromatography on silica gel (n-hexane:ethyl acetate=2:1→1:1) to give the title compound having the following physical data.

NMR: δ7.23 (1H, t, J=8 Hz), 7.08 (1H, d, J=8 Hz), 6.78 (1H, d, J=8 Hz), 5.05–4.95 (1H, m), 3.83 (3H, s), 3.67 (3H, s), 3.63 (2H, t, J=7 Hz), 3.05–2.95 (2H, m), 2.65–2.53 (2H, m), 1.90–1.30 (8H, m).

MS: m/z 310 (M+), 223.

REFERENCE EXAMPLE 40

6-Oxo-6-[2-(2-methoxycarbonylethyl)-3-methoxyphenyl]hexanoic acid

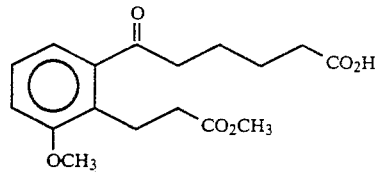

A solution of 6-oxo-6-[2-(2-methoxycarbonylethyl)-3-methoxyphenyl]hexanal (450 mg), which was prepared with using the ester prepared in reference example 39 by the same procedure as reference example 14, in acetone (6 ml) was ice-cooled. 2.67N Jone's reagent (2 ml) was added dropwise to the solution. The mixture was stirred for 1 hr. with ice-cooling. Isopropyl alcohol was added to the solution to stop the reaction. Water was added to the solution to dissolve chromic anhydride. The reaction mixture was extracted with diethyl ether. The extract was washed with water, dried over anhydrous magnesium sulfate and then evaporated. The residue was purified by column chromatography on silica gel (n-hexane:ethyl acetate=2:1→1:1) to give the title compound (369 mg) having the following physical data.

NMR: δ7.25 (1H, t, J=8 Hz), 7.08 (1H, d. J=8 Hz), 6.95 (1H, d, J=8 Hz), 3.85 (3H, s), 3.67 (3H, s), 3.05–2.95 (4H, m), 2.67–2.55 (2H, m), 2.40 (2H, t, J=7 Hz), 1.85–1.60 (4H, m).

EXAMPLE 1

3-[1-[6-(4-methoxyphenyl)hex-5E-enyl]oxy-4-(5-oxo-5-morpholinopentanamido)benzen-2-yl]propionic acid

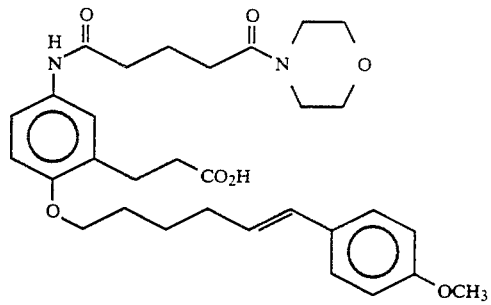

The butyl ester (70 mg; prepared in reference example 6) was dissolved in formic acid (5 ml). The solution was stirred for 5 hr. at room temperature. The reaction solution was evaporated to remove formic acid. The residue was purified by column chromatography on silica gel (ethyl acetate:methanol=10:1) to give the title compound (40 mg) of the present invention, having the following physical data.

TLC(ethyl acetate:methanol=10:1): Rf 0.10;
IR(cm$^{-1}$): ν3307, 2932, 1723, 1609, 1510, 1245, 1116, 1032.

EXAMPLE 1(a)-1(v)

The compounds, of the present invention, shown in the following table 4 were obtained, with using the compounds which were prepared with using the butyl ester prepared in reference example 5 and the corresponding amines by the same procedure as reference example 6 (with the proviso that the corresponding amines were used instead of morpholine) or the compounds which were prepared with using the corresponding appropriate compounds shown in the formula MsO-Z$^1$-B$^2$ or Br-Z$^2$-B$^2$ (wherein all of the symbols are the same meaning as described hereinbefore) by the same procedure as reference example 4, 5 and 6 (with the proviso that the corresponding amines were used instead of morpholine), by the same procedure as example 1.

TABLE 4

| Ex. No. | Structural formula | TLC | IR (cm$^{-1}$) |
|---|---|---|---|
| 1(a) | | Rf 0.31 (ethyl acetate: methanol = 6:1) | ν 3357, 2952, 1715, 1683, 1602, 1542, 1508, 1471, 1410, 1235, 1176, 1117, 1031, 972, 886, 825 |
| 1(b) | | Rf 0.37 (ethyl acetate: methanol = 5:1) | ν 3333, 2940, 1704, 1687, 1608, 1554, 1505, 1474, 1422, 1277, 1222, 1200, 1124, 1029, 805 |
| 1(c) | | Rf 0.52 (ethyl acetate: methanol = 5:1) | ν 3335, 2923, 2849, 1687, 1607, 1553, 1505, 1473, 1422, 1221, 811 |
| 1(d) | | Rf 0.53 (ethyl acetate: methanol = 5:1) | ν 3270, 2918, 2850, 1712, 1650, 1605, 1539, 1504, 1473, 1415, 1230, 1116, 1031, 805, 718 |
| 1(e) | | Rf 0.30 (chloroform: methanol = 10:1) | ν 1634, 1506, 1242, 1048, 977, 810 |

| Ex. No. | Structural formula | TLC | IR (cm$^{-1}$) |
|---|---|---|---|
| 1(f) | | Rf 0.28 (chloroform: methanol = 10:1) | ν 2937, 1715, 1607, 1550, 1505, 1472, 1422, 1240, 1176, 1119, 1023, 969, 810, 756 |
| 1(g) | | Rf 0.30 (ethyl acetate: methanol = 6:1) | ν 3273, 2932, 2855, 2837, 1711, 1650, 1601, 1540, 1511, 1406, 1416, 1348, 1248, 1229, 1178, 1116, 1034, 971, 805 |
| 1(h) | | Rf 0.30 (ethyl acetate: methanol = 6:1) | ν 3284, 3067, 2927, 2854, 1735, 1711, 1650, 1624, 1600, 1561, 1511, 1468, 1416, 1246, 1172, 1117, 1033, 805 |
| 1(i) | | Rf 0.27 (chloroform: methanol = 10:1) | ν 3305, 2933, 1728, 1608, 1550, 1504, 1471, 1242, 1175, 1119, 1051, 968, 810, 756 |
| 1(j) | | Rf 0.49 (ethyl acetate: methanol = 6:1) | ν 3304, 2933, 2857, 1727, 1613, 1549, 1512, 1504, 1469, 1419, 1245, 1178, 1118, 1036, 883, 813, 753 |
| 1(k) | | Rf 0.49 (ethyl acetate: methanol = 6:1) | ν 3276, 2933, 1710, 1648, 1600, 1539, 1503, 1414, 1347, 1258, 1228, 1116, 1058, 968, 883, 805, 694 |

TABLE 4-continued

| Ex. No. | Structural formula | TLC | IR (cm$^{-1}$) |
|---|---|---|---|
| 1(l) | (structure) | Rf 0.34 (ethyl acetate: methanol = 6:1) | ν 3300, 2937, 1719, 1616, 1549, 1503, 1467, 1438, 1420, 1242, 1162, 1118, 1051, 1029, 976, 884, 814 |
| 1(m) | (structure) | Rf 0.39 (ethyl acetate: methanol = 6:1) | ν 3301, 3008, 2938, 1723, 1607, 1549, 1503, 1471, 1453, 1423, 1236, 1156, 1119, 1047, 971, 881, 813, 756 |
| 1(n) | (structure) | Rf 0.50 (ethyl acetate: methanol = 10:1) | ν 2936, 1273, 1655, 1510, 1484, 1420, 1246 |
| 1(o) | (structure) | Rf 0.40 (ethyl acetate: methanol = 10:1) | ν 3273, 2933, 1691, 1646, 1551, 1511, 1248 |
| 1(p) | (structure) | Rf 0.55 (ethyl acetate: methanol = 6:1) | ν 3295, 3262, 2936, 1695, 1676, 1609, 1552, 1511, 1501, 1474, 1275, 1245, 1116, 1031, 972, 882, 842, 816 |

TABLE 4-continued

| Ex. No. | Structural formula | TLC | IR (cm$^{-1}$) |
|---|---|---|---|
| 1(q) | (structure: 4-[N-(4-methylthiocinnamyloxy-type)phenyl]glutaramide with CO$_2$H and N(CH$_3$)$_2$, SCH$_3$ group) | Rf 0.29 (ethyl acetate: methanol = 6:1) | ν 3283, 3120, 2934, 2864, 1732, 1650, 1623, 1526, 1500, 1475, 1459, 1439, 1416, 1347, 1233, 1175, 1117, 969, 802 |
| 1(r) | (structure with 3,4-dimethoxyphenyl group, OCH$_3$, OCH$_3$) | Rf 0.24 (ethyl acetate: methanol = 6:1) | ν 3303, 3010, 2936, 1770, 1725, 1625, 1549, 1514, 1501, 1467, 1418, 1262, 1236, 1140, 1119, 1027, 755 |
| 1(s) | (structure with 4-methylphenyl group, CH$_3$) | Rf 0.36 (ethyl acetate: methanol = 6:1) | ν 3301, 3011, 2937, 2869, 1723, 1616, 1549, 1504, 1472, 1414, 1235, 1119, 1043, 969, 813, 756 |
| 1(t) | (structure with 4-chlorophenyl group, Cl) | Rf 0.40 (ethyl acetate: methanol = 6:1) | ν 3300, 3011, 2937, 1714, 1615, 1549, 1503, 1472, 1405, 1234, 1119, 1091, 1013, 969, 811, 756 |
| 1(u) | (structure with CON(CH$_3$)$_2$ on benzamide and 4-methoxyphenyl group, OCH$_3$) | Rf 0.40 (ethyl acetate: methanol = 10:1) | ν 3350, 2934, 1724, 1611, 1510, 1249 |

EXAMPLE 2

TABLE 5

| Ex. No. | Structural formula | TLC | IR (cm$^{-1}$) |
|---|---|---|---|
| 2 (a) | | Rf 0.40 (chloroform: methanol = 100:10:1) | ν 3294, 2935, 1699, 1665, 1626, 1513, 1418, 1247, 962 |
| 2 (b) | | Rf 0.70 (chloroform: methanol = 17:2:1) | ν 3281, 2935, 1702, 1643, 1608, 1536, 1510, 1247 |

3-[1-[6-(4-methoxyphenyl)hex-5E-enyl]oxy-4-(4-carboxylbutanamido)benzen-2-yl]propionic acid

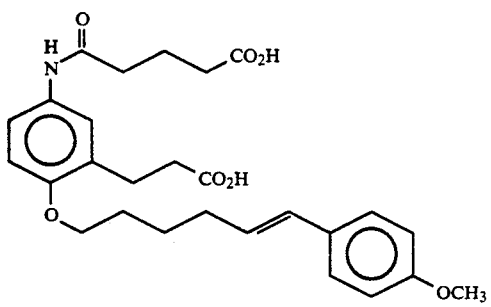

The title compound, of the present invention, having the following physical data was obtained with using the ester prepared in reference example 5 by the same procedure as example 1.

TLC(chloroform:methanol:acetic acid = 17:2:1): Rf 0.70;

IR(cm$^{-1}$): ν3276, 2932, 1702, 1650, 1609, 1541, 1512, 1245, 1223.

EXAMPLE 2(a) AND 2(b)

The compounds, of the present invention, shown in the following table 5 were obtained, with using a tert-butyl ester, which was prepared with using the ester prepared in reference example 9 by the same procedure as reference example 4→reference example 5, for example 2(a), and a tert-butyl ester, which was prepared with using the compound prepared in reference example 2 by the same procedure as reference example 3 (with the proviso that 3-carboxylbenzoyl chloride was used instead of 4-methoxycarbonylbutanoylchloride)→reference example 4→reference example 5, for example 2(b), by the same procedure as example 2.

EXAMPLE 3

3-[1-[6-(4-methoxyphenyl)hex-5E-enyl]oxy-4-heptanamidobenzen-2-yl]propionic acid

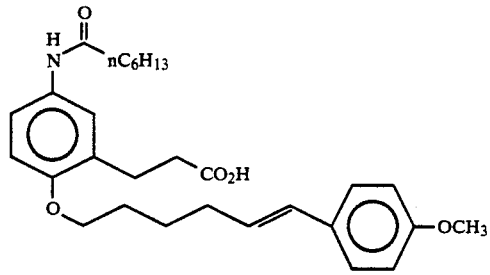

The title compound of the present invention, having the following physical data, was obtained with using the compound, which was prepared with using the ester prepared in reference example 2 by the same procedure as reference example 3 (with the proviso that heptanoyl chloride was used instead of methyl 4-(chloroformyl)-butyrate)→reference example 4, by the same procedure as example 1.

TLC(ethyl acetate): Rf 0.40;

IR(cm$^{-1}$): ν3436, 3269, 2934, 2872, 1732, 1607, 1159, 1512, 1252.

EXAMPLE 3(a)–3(c)

The compounds, of the present invention, shown in the following table 6 was obtained with using the corresponding acyl halide instead of heptanoyl chloride by the same procedure as example 3.

TABLE 6

| Ex. No. | Structural formula | TLC | IR (cm$^{-1}$) |
|---|---|---|---|
| 3 (a) | | Rf 0.60 (ethyl acetate) | ν 3277, 2935, 1698, 1643, 1608, 1533, 1510, 1248 |
| 3 (b) | | Rf 0.50 (ethyl acetate) | ν 3281, 2922, 2852, 1698, 1651, 1609, 1541, 1511, 1250 |
| 3 (c) | | Rf 0.40 (ethyl acetate: methanol = 10:1) | ν 3326, 2940, 1709, 1636, 1609, 1561, 1510, 1248 |

EXAMPLE 4

3-[1-[6-(4-methoxyphenyl)hex-5E-enyl]oxy-4-(5-hydroxypentanamido)benzen-2-yl]propionic acid

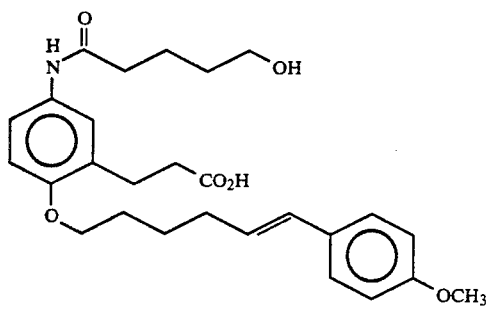

The title compound, of the present invention, having the following physical data was obtained with using the ester prepared in reference example 7, by the same procedure as example 1.

TLC(ethyl acetate:methanol=7:1): Rf 0.50;
MS: m/z 469(M+), 369, 189, 163, 147, 121.

EXAMPLE 4(a) and 4(b)

The compounds, of the present invention, shown in the following table 7 were obtained, with using a tert-butyl ester, which was prepared with using the tert-butyl ester prepared in reference example 2 by the same procedure as reference example 3 (with the proviso that the corresponding appropriate reagents were used instead of 4-methoxycarbonylbutanoyl chloride)→reference example 4→reference example 5→reference example 7, by the same procedure example 4.

TABLE 7

| Ex. No. | Structural formula | TLC | IR (cm$^{-1}$) |
|---|---|---|---|
| 4 (a) | | Rf 0.67 (ethyl acetate: methanol = 6:1) | ν 3288, 2944, 2837, 2529, 1698, 1663, 1607, 1555, 1509, 1473, 1443, 1339, 1278, 1246, 1235, 1176, 1159, 1111, 1033, 971, 834 |
| 4 (b) | | Rf 0.50 (ethyl acetate: methanol = 10:1) | ν 3368, 2932, 1731, 1642, 1607, 1541, 1508, 1245, 1176, 1033 |

EXAMPLE 5

3-[1-(5E-7-hydroxypentadecenyl)oxy-4-(4-dimethylaminocarbonylbutanamido)benzen-2-yl]propionic acid

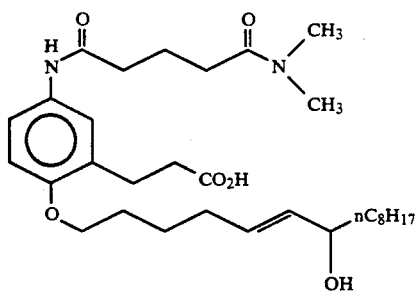

The title compound, of the present invention, having the following physical data was obtained with using the methyl ester prepared in reference example 16 by the same procedure as reference example 5.

TLC(chloroform:methanol=10:1): Rf 0.29;

IR(cm$^{-1}$): ν3306, 2928, 2856, 1712, 1626, 1552, 1504, 1470, 1414, 1235, 1119, 1051, 972, 812.

EXAMPLE 5(a)–5(e)

The compounds, of the present invention, shown in the following table 8 were obtained with using the compounds, which were prepared with using the corresponding appropriate reagent by the same procedure as the steps for the preparation of the compound of reference example 16, by the same procedure as example 5.

TABLE 8

| Ex. No. | Structural formula | TLC | IR (cm$^{-1}$) |
|---|---|---|---|
| 5 (a) | | Rf 0.35 (chloroform: methanol = 10:1) | ν 532(M$^+$), 514, 391 |

TABLE 8-continued

| Ex. No. | Structural formula | TLC | IR (cm$^{-1}$) |
|---|---|---|---|
| 5 (b) | | Rf 0.29 (chloroform: methanol = 10:1) | $\nu$ 3304, 2932, 2859, 1718, 1626, 1551, 1504, 1471, 1407, 1235, 1119, 1052, 972, 912, 885, 813, 733 |
| 5 (c) | | Rf 0.28 (chloroform: methanol = 10:1) | $\nu$ 3305, 2937, 2863, 1718, 1614, 1549, 1512, 1504, 1471, 1419, 1246, 1179, 1119, 1038, 973, 815, 755, 666 |
| 5 (d) | | Rf 0.28 (chloroform: methanol = 10:1) | $\nu$ 3305, 2934, 2874, 1723, 1658, 1615, 1550, 1504, 1471, 1416, 1235, 1119, 1049, 972, 813, 733 |
| 5 (e) | | Rf 0.28 (chloroform: methanol = 10:1) | $\nu$ 3305, 2927, 2854, 1714, 1626, 1551, 1504, 1473, 1450, 1417, 1235, 1119, 1044, 974, 913, 892, 813, 733 |

EXAMPLE 6

3-[1-[6-(4-methoxyphenyl)hexyl]oxy-4-(4-methylphenyl)-sulfonylaminobenzen-2-yl]propionic acid

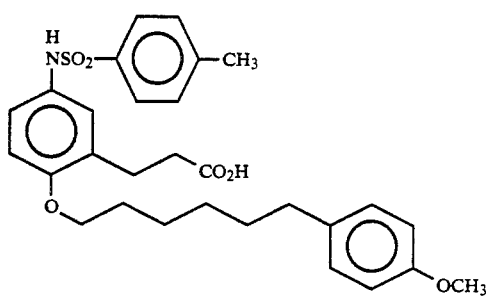

The title compound, of the present invention, having the following physical data was obtained with using a tert-butyl ester, which was prepared with using the tert-butyl ester prepared in reference example 17 by the same procedure as reference example 4 (with the proviso that the corresponding appropriate methanesulfonate was used instead of 6-(p-methoxyphenyl)-5E-hexenol methanesulfonate)→reference example 18→reference example 3 (with the proviso that the corresponding appropriate sulfonyl chloride was used instead of 4-methoxycarbonylbutanoyl chloride), by the same procedure as example 1.

TLC(ethyl acetate:n-hexane=2:1): Rf 0.40;

IR(cm$^{-1}$): $\nu$3256, 2932, 2857, 1714, 1612, 1505, 1471, 1396, 1245, 1158, 1037, 815, 667.

EXAMPLE 6(a)–6(c)

The compounds, of the present invention, shown in the following table 9 were obtained by the same procedure as example 6.

TABLE 9

| Ex. No. | Structural formula | TLC | IR (cm$^{-1}$) |
|---|---|---|---|
| 6 (a) | | Rf 0.30 (ethyl acetate: n-hexane = 2:1) | $\nu$ 3264, 2936, 1708, 1608, 1511, 1248, 1160 |
| 6 (b) | | Rf 0.30 (ethyl acetate) | $\nu$ 3259, 2935, 1697, 1511, 1311, 1249, 1225, 1152 |
| 6 (c) | | Rf 0.30 (ethyl acetate: n-hexane = 2:1) | $\nu$ 3247, 2935, 1708, 1510, 1247, 1154 |

EXAMPLE 7

3-[1-[6-(4-methoxyphenyl)hexyl]oxy-4-(3-dimethylaminocarbonyl-n-propyl)sulfonylaminobenzen-2-yl]propionic acid

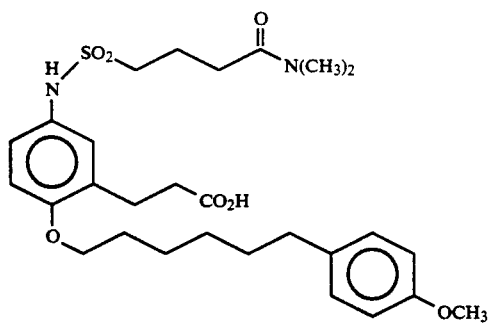

The title compound, of the present invention, having the following physical data was obtained with using the phenol compound (prepared in reference example 1) by the same procedure as reference example 4 (with the proviso that the corresponding appropriate methanesulfonate was used instead of 6-(p-methoxyphenyl)-5E-hexenol methanesulfonate)→reference example 2→reference example 3 (with the proviso that the corresponding appropriate sulfonyl chloride was used instead of 4-methoxycarbonylbutanoyl chloride)→reference example 5→reference example 6→example 1.

TLC(ethyl acetate): Rf 0.10;
IR(cm$^{-1}$): $\nu$2933, 1693, 1621, 1512, 1247, 1207, 1148.

EXAMPLE 7(a)

3-[1-[6-(4-methoxyphenyl)hex-5E-enyl]oxy-4-(3-dimethylaminocarbonyl-n-propyl)sulfonylaminobenzen-2-yl]propionic acid

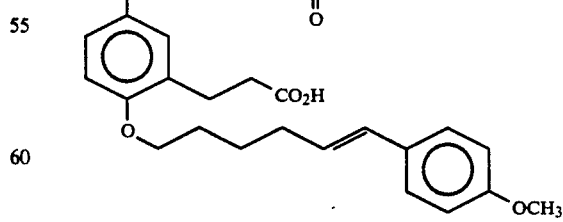

The title compound, of the present invention, having the following physical data was obtained by the same procedure as example 7.

TLC(ethyl acetate:methanol = 10:1): Rf 0.30;
IR(cm$^{-1}$): $\nu$2937, 1732, 1615, 1505, 1246, 1152, 1034.

EXAMPLE 8

3-[1-[6-(4-methoxyphenyl)hex-5E-enyl]oxy-4-(3-carboxylpropyl)sulfonylaminobenzen-2-yl]propionic acid

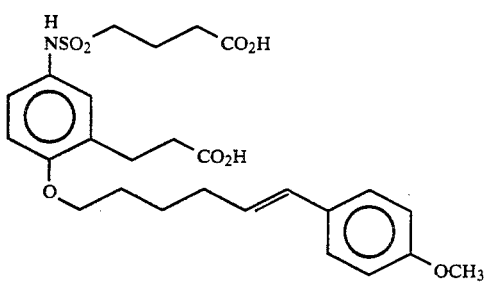

The title compound, of the present invention, having the following physical data was obtained with using the tert-butyl ester prepared in reference example 18 by the same procedure as reference example 3→reference example 5→example 1.

TLC(ethyl acetate:methanol=9:1): Rf 0.10;
IR(cm$^{-1}$): ν3270, 2932, 1713, 1608, 1504, 1470, 1299, 1153.

EXAMPLE 9

3-[1-[6-(4-methoxyphenyl)hex-5E-enyl]oxy-4-(N-acetyl-N-mesyl)-aminobenzen-2-yl]propionic acid

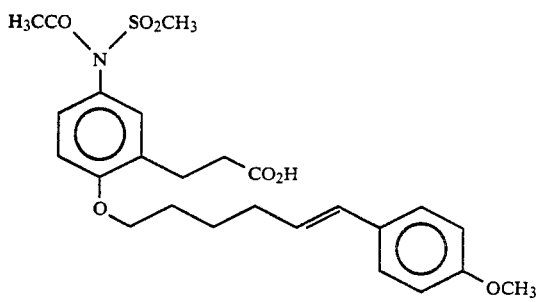

The title compound, of the present invention, having the following physical data was obtained with using the tert-butyl ester prepared in reference example 19 by the same procedure as example 1.

TLC(ethyl acetate): Rf 0.30;
IR(cm$^{-1}$): ν2937, 1707, 1511, 1500, 1353, 1246, 1163.

EXAMPLE 10

3-[1-[6-(4-methoxyphenyl)hex-5E-enyl]oxy-4-dimesylaminobenzen-2-yl]propionic acid

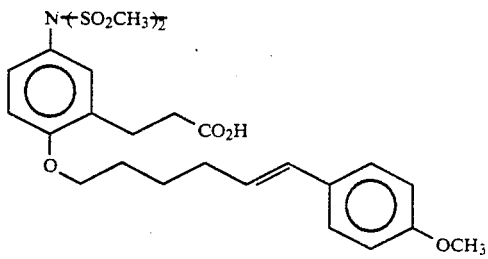

The title compound, of the present invention, having the following physical data was obtained with using the tert-butyl ester prepared in reference example 20 by the same procedure as example 1.

TLC(ethyl acetate:n-hexane=2;1): Rf 0.25;
IR(cm$^{-1}$): ν2936, 1708, 1607, 1511, 1368,, 1248, 1161.

EXAMPLE 10(a)–10(c)

The compounds, of the present invention, shown in the following table 10 were obtained with using tert-butyl esters, which were prepared with using the ester prepared in reference example 18 by the same procedure as reference example 20 (with the proviso that the corresponding appropriate sulfonyl chloride was used instead of methanesulfonyl chloride), by the same procedure as example 10.

TABLE 10

| Ex. No. | Structural formula | TLC | IR (cm$^{-1}$) |
|---|---|---|---|
| 10 (a) | (N(SO$_2$-C$_6$H$_4$-CH$_3$)$_2$ substituted benzene with propionic acid and hex-5E-enyloxy-4-methoxyphenyl chain) | Rf 0.30 (ethyl acetate: n-hexane = 2:1) | ν 2934, 1709, 1607, 1511, 1499, 1377, 1249, 1168, 662, 549 |
| 10 (b) | (N(SO$_2$-nC$_4$H$_9$)$_2$ substituted benzene with propionic acid and hex-5E-enyloxy-4-methoxyphenyl chain) | Rf 0.40 (ethyl acetate: n-hexane = 2:1) | ν 2961, 1714, 1607, 1504, 1470, 1380, 1036, 914, 865 |

TABLE 10-continued

| Ex. No. | Structural formula | TLC | IR (cm$^{-1}$) |
|---|---|---|---|
| 10 (c) | 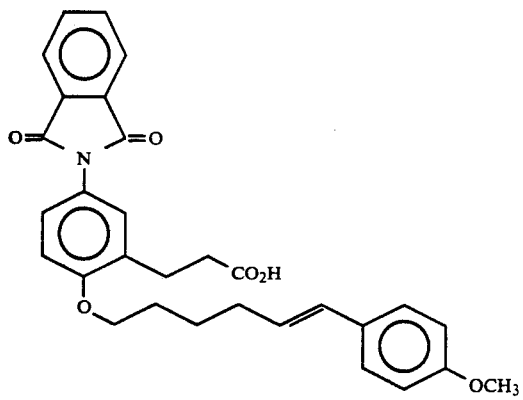 | Rf 0.40 (ethyl acetate: n-hexane = 2:1) | ν 2932, 1708, 1607, 1511, 1498, 1374, 1352, 1249, 1158 |

EXAMPLE 11

3-[1-[6-(4-methoxyphenyl)hex-5E-enyl]oxy-4-phthalimidobenzen-2-yl]propionic acid The title compound, of the present invention, having the following physical data was obtained with using the tert-butyl ester prepared in reference example 21 by the same procedure as example 1.

MS: m/z 499 (M+), 293, 265, 189, 147, 121;
IR(cm$^{-1}$): ν3215, 2935, 1756, 1702, 1511, 1256, 1150, 1122, 725.

EXAMPLE 12

3-[1-[6-(4-methoxyphenyl)hex-5E-enyl]oxy-4-(perhydro-1,2-thiazin-1,1,3-trione-2-yl]benzen-2-yl]propionic acid The title compound, of the present invention, having the following physical data was obtained with using the tert-butyl ester prepared in reference example 22 by the same procedure as example 1.

TLC(ethyl acetate:methanol=10.1): RF 0.40;
IR(cm$^{-1}$): ν2935, 1718, 1697, 1511, 1500, 1333, 1248, 1151, 1120, 1025.

Example 12(a) and 12(b)

The compounds, of the present invention, shown in the following table 11 were obtained with using the compounds, which were prepared with using the corresponding appropriate reagents by the same procedure as the steps for the preparation of the compound of reference example 22, by the same procedure as example 12.

TABLE 11

| Ex. No. | Structural formula | TLC | IR (cm$^{-1}$) |
|---|---|---|---|
| 12 (a) | | Rf 0.20 (ethyl acetate) | ν 2933, 1717, 1696, 1513, 1500, 1333, 1249, 1152, 1121, 1026, 821, 529 |

TABLE 11-continued

| Ex. No. | Structural formula | TLC | IR (cm$^{-1}$) |
|---|---|---|---|
| 12 (b) | 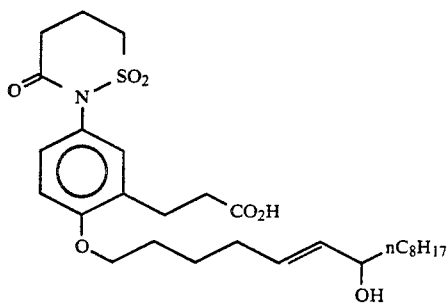 | Rf 0.40 (ethyl acetate: methanol = 10:1) | ν 3362, 1729, 1510, 1323, 1250, 1159 |

EXAMPLE 13

3-[1-(5E-7-hydroxy-n-pentadecenyl)oxy-4-(perhydro-1,2-thiazin-1,1,3-trione-2 -yl)benzen-2-yl]propionic acid

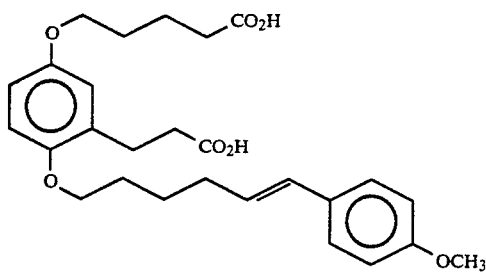

The title compound, of the present invention, having the following physical data was obtained with using the tert-butyl ester prepared in reference example 23 by the same procedure as reference example 14→reference example 15→reference example 16→reference example 18→reference example 3 (with the proviso that the corresponding appropriate sulfonyl chloride was used instead of 4-methoxycarbonylbutanoyl chloride)→reference example 5→reference example 22→reference example 11→reference example 13.

TLC(ethyl acetate:methanol=9:1): RF 0.50;

MS: m/z 537(M+), 519, 424, 406, 369, 342, 313, 295.

EXAMPLE 14

3-[1-[6-(4-methoxyphenyl)hex-5E-enyl]oxy-4-(4-carboxylbutoxy)benzen-2-yl]propionic acid

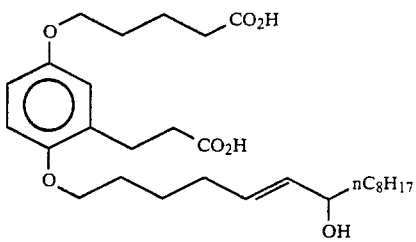

The title compound, of the present invention, having the following physical data was obtained with using the ethyl ester prepared in reference example 27 by the same procedure as reference example 2→reference example 4→reference example 5 and then purification by column chromatography on silica gel.

TLC(chloroform:methanol=10:1): Rf 0.35;

IR(cm$^{-1}$): ν2938, 1669, 1606, 1510, 1474, 1426, 1289, 1246, 1227, 1178, 1109, 1053, 968, 847, 805.

EXAMPLE 15

3-[1-(5E-7-hydroxy-n-pentadecenyl)oxy-4-(4-carboxylbutyl)-oxybenzen-2-yl]propionic acid The title compound, of the present invention, having the following physical data was obtained with using the ethyl ester prepared in reference example 27 by the same procedure as reference example 2→reference example 10→reference example 23→reference example 14→reference example 15→reference example 16→reference example 5 and then purification by column chromatography on silica gel.

TLC(chloroform:methanol): RF 0.36;

IR(cm$^{-1}$): ν2926, 2852, 1696, 1508, 1466, 1278, 1229, 1168, 1108, 1070, 972, 873, 810.

EXAMPLE 15(a)–15(c)

The compounds, of the present invention, shown in the following table 12 were obtained with using 6-hydroxycoumarin prepared in reference example 25 by the same procedure as reference example 26 (with the proviso that the corresponding appropriate esters were used instead of ethyl 5-bromopentanoate in example 15(b) and 15(c))→reference example 27→reference example 2→reference example 10→reference example 23→reference example 14→reference example 15 (with the proviso that the corresponding appropriate phosphonate was used instead of dimethyl 2-oxodecylphosphonate for example 15(a))→reference example 16→reference example 5 and then purification by column chromatography on silica gel.

TABLE 12

| Ex. No. | Structural formula | TLC | IR (cm$^{-1}$) |
|---|---|---|---|
| 15 (a) | | Rf 0.26 (chloroform: methanol = 10:1) | ν 2937, 1709, 1612, 1586, 1513, 1501, 1470, 1246, 1221, 1178, 1038, 974, 810, 758 |
| 15 (b) | | Rf 0.25 (chloroform: methanol = 10:1) | ν 3531, 2925, 2852, 1694, 1507, 1466, 1426, 1406, 1393, 1300, 1258, 1228, 1208, 1167, 1110, 1060, 1022, 977, 897, 868, 816, 807, 712 |
| 15 (c) | | Rf 0.09 (chloroform: methanol = 10:1) | ν 3419, 3138, 2926, 2853, 1725, 1594, 1500, 1441, 1420, 1404, 1253, 1222, 1181, 1123, 1090, 978, 952, 879, 777 |

EXAMPLE 16

3-[1-]6-(4-methoxypheny)hex-5E-enyl]oxy-4(4-dimethylaminocarbonyl-n-butyl)oxybenzen-2-yl]propionic acid

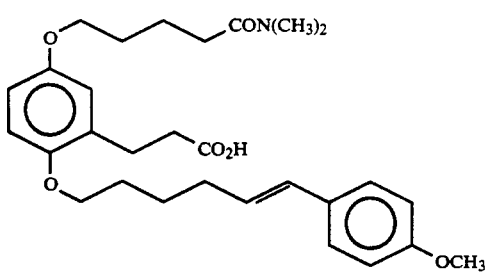

The title compound, of the present invention, having the following physical data was obtained with using 6-hydroxy-coumarin prepared in reference example 25 by the same procedure as reference example 26 (with the proviso that N, N-dimethyl-5-bromopentanamide was used instead of ethyl 5-bromopentanoate)→reference example 27→reference example 2→reference example 4→reference example 5 and then purification by column chromatography on silica gel.

TLC(chloroform:methanol = 10:1): Rf 0.56;

IR(cm$^{-1}$); ν2937, 1728, 1609, 1510, 1411, 1402, 1247, 1220, 1176, 1121, 1036, 969, 846, 803, 756.

EXAMPLE 16(a)

3-[1-[6-(4-methoxphenyl)hex-5E-enyl]oxy-4-(3-dimethylaminocarbonyl-n-propyl)oxybenzen-2-yl]propionic acid

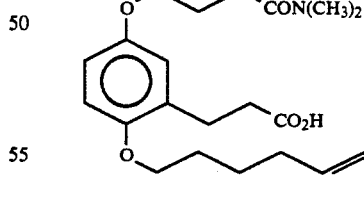

The title compound, of the present invention, having the following physical data was obtained with using 6-hydroxy-coumarin prepared in reference example 25 by the same procedure as example 16 (with the proviso that N,N-dimethyl-4-bromobutanamide was used instead of N,N-dimethyl-5-bromopentanamide).

TLC(ethyl acetate): Rf 0.42;

IR(cm$^{-1}$): ν2935, 1729, 1608, 1505, 1471, 1246, 1219, 1176, 1121, 1038, 969, 847, 803.

EXAMPLE 17

3-[1-(5E-7-hydroxy-n-pentadecenyl)oxy-4-(4-dimethylaminocarbonylbutyl)oxybenzen-2-yl]propionic acid

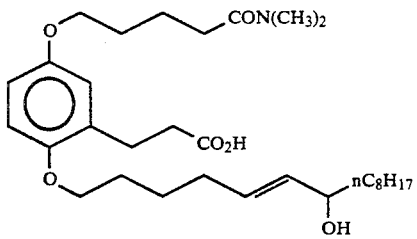

The title compound, of the present invention, having the following physical data was obtained with using 6-hydroxycoumarin prepared in reference example 25 by the same procedure as reference example 26 (with the proviso that N,N-dimethyl-5-bromopentanamide was used instead of ethyl 5-bromopentanoate)→reference example 27→reference example 2→reference example 10→reference example 23→reference example 14→reference example 15→reference example 16→reference example 5 and then purification by column chromatography on silica gel.

TLC(chloroform:methanol = 10:1): Rf 0.42;

IR(cm$^{-1}$): ν3402, 2928, 2857, 1727, 1626, 1500, 1470, 1402, 1220, 1158, 1058, 972, 804.

EXAMPLE 17(a) and 17(b)

EXAMPLE 17(a)

3-[1-(5E,9Z-7-hydroxy-n-pentadecadienyl)oxy-4-(4-dimethylaminocarbonylbutyl)oxybenzen-2-yl]propionic acid

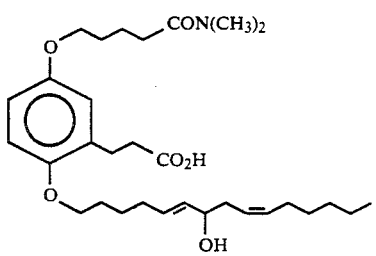

EXAMPLE 17(b)

3-[1-(5E-6-methyl-7-hydroxy-n-pentadecenyl)oxy-4-(4-dimethylaminocarbonylbutyl)oxybenzen-2-yl]propionic acid

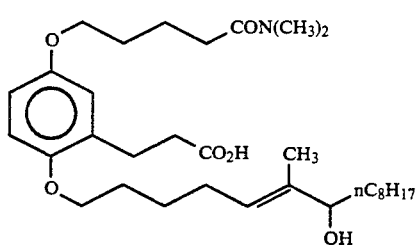

The title compound, of the present invention, having the following physical data was obtained with using 6-hydroxy-coumarin prepared in reference example 25 by the same procedure as example 17 (with the proviso that the corresponding appropriate phosphonate was used instead of dimethyl 2-oxodecylphosphonate for the same procedure as reference example 15).

17(a):

TLC(chloroform:methanol = 10:1): Rf 0.46;

IR(cm−1): ν2931, 2860, 1727, 1626, 1500, 1470, 1402, 1220, 1158, 1055, 804.

17(b):

TLC(chloroform:methanol = 10:1): Rf 0.51;

IR(cm$^{-1}$): ν2928, 2857, 1728, 1627, 1500, 1471, 1401, 1220 1159, 1057, 804.

EXAMPLE 18

3-[1-[6-(4-methoxyphenyl)hex-5E-enyl]oxy-4-(4-dimethylaminocarbonylbutyl)benzen-2-yl]propionic acid

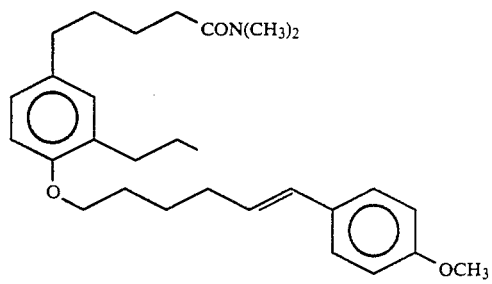

The title compound, of the present invention, having the following physical data was obtained with using the ester in reference example 31 by the same procedure as reference example 4→reference example 5 and then purification by column chromatography on silica gel.

TLC(ethyl acetate): Rf 0.50;

IR(cm$^{-1}$): ν2935, 2861, 1729, 1609, 1510, 1468, 1402, 1249, 1179, 1121, 1036, 969, 846, 809.

EXAMPLE 18(a)

3-[1-[6-(4-methoxyphenyl)hex-5E-enyl]oxy-4-(5-dimethylaminocarbonylpentyl)benzen-2-yl]propionic acid

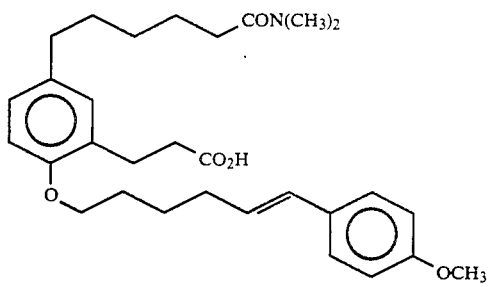

The title compound, of the present invention, having the following physical data was obtained with using an ester, which was prepared with using 3-(1methoxybenzen-2yl)propionic acid by the same procedure as reference example 12→reference example 28 (with the proviso that methyl 5-(chloroformyl)pentanoate was used instead of methyl 4-(chloroformyl)butyrate)→reference example 16→reference example 29→reference example 30→reference example 31, by the same procedure as example 18.

TLC(ethyl acetate:methanol = 10:1): Rf 0.65;

IR(cm$^{-1}$): ν2933, 2857, 1728, 1609, 1511, 1467, 1402, 1290, 1249, 1176, 1121, 1035, 968, 846, 809, 756.

EXAMPLE 19

3-[1-[6-(4methoxyphenyl)hex-5E-enyl]oxy-4-(1oxo-4-dimethylaminocarbonylbutyl)benzen-2-yl]propionic acid

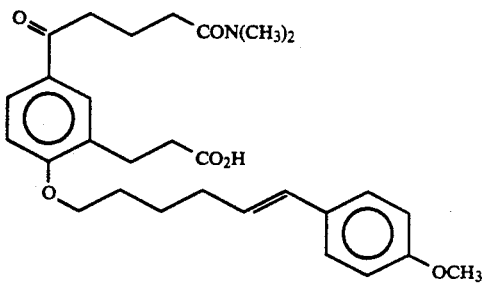

The title compound, of the present invention, having the following physical data was obtained with using the dicarboxylic acid prepared in reference example 32 by the same procedure as reerence example 30→reference example 27→reference example 2→reference example 6→reference example 4→reference example 5 and then purification by column chromatography on silica gel.

TLC (ethyl acetate:methanol=9:1): Rf 0.56;

IR (cm$^{-1}$): ν3448, 2941, 2871, 2519, 1736, 1714, 1674, 1603, 1512, 1470, 1411, 1362, 1334, 1299, 1282, 1254, 1176, 1160, 1126, 1106, 1035.

EXAMPLE 19(a)

3-[1-[6-(4-methoxyphenyl)hex-5E-enyl]oxy-4-(1-oxo-5-dimethylaminocarbonylpentyl]benzen-2-yl]propionic acid

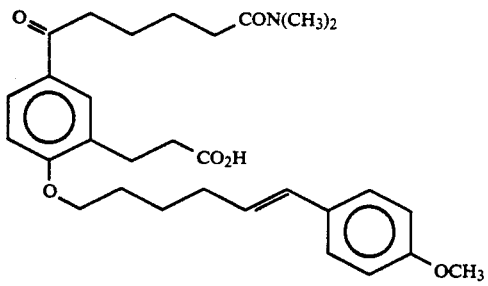

The title compound, of the present invention, having the following physical data was obtained with using a dicarboxylic acid, which was prepared with using 3-(1-methoxybenzen-2-yl)propionic acid by the same procedure as reference example 12→reference example 28 (with the proviso that methyl 5-(chloroformyl)pentanoate was used instead of methyl 4-(chloroformyl)-butyrate)→reference example 5→reference example 32, by the same procedure as example 19.

TLC (ethyl acetate:methanol=10:1): Rf 0.50;

IR (cm$^{-1}$): ν3034, 2941, 2872, 1729, 1674, 1617, 1578, 1510, 1466, 1411, 1373, 1315, 1248, 1210, 1176, 1116, 1038, 1016, 998, 972, 845, 817.

EXAMPLE 20 AND 20(a)

EXAMPLE 20

9-[1-[6-(4-methoxyphenyl)hex-5E-enyl]oxy-4-(1-hydroxy-4-dimethylaminocarbonylbutyl)benzen-2-yl]propionic acid

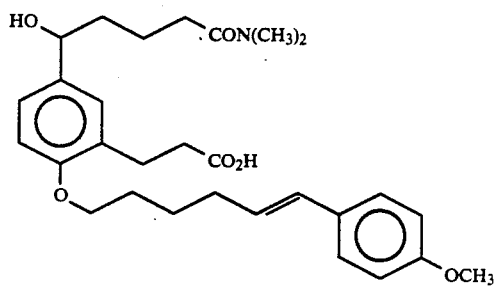

EXAMPLE 20(a)

3-[1-[6-(4-methoxyphenyl)hex-5E-enyl]oxy-4-(1-hydroxy-5-dimethylaminocarbonylpentyl)benzen-2-yl]propionic acid

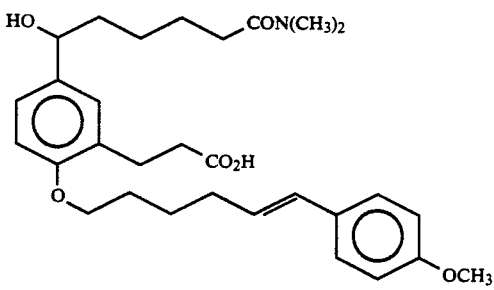

The title compounds, of the present invention, having the following physical data were obtained with using the carboxylic acid prepared in reference example 19 and 19(a) by the same procedure as reference example 16.

EXAMPLE 20

TLC (ethyl acetate:methanol=9:1): Rf 0.48;

IR (cm$^{-1}$): ν2936, 1723, 1609, 1511, 1468, 1403, 1249, 1176, 1120, 1035.

EXAMPLE 20(a)

TLC (ethyl acetate:methanol=10:1): Rf 0.42;

IR (cm$^{-1}$): ν2936, 2864, 1725, 1609, 1511, 1467, 1403, 1249, 1176, 1119, 1035, 969, 814, 756.

EXAMPLE 21

3-[1-[6-(4-methoxyphenyl)hex-5E-enyl]oxy-4-n-propoxybenzen-2-yl]propionic acid

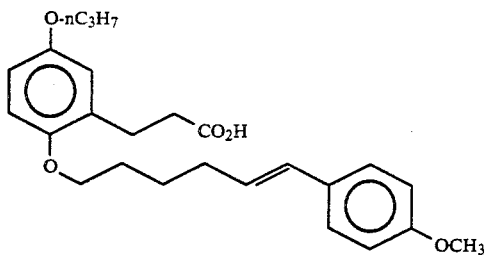

The title compound, of the present invention, having the following physical data was obtained with using 6-hydroxy-coumarin prepared in reference example 25 by the same procedure as reference example 26 (with the proviso that 1-bromo-n-propane was used instead of ethyl 5-bromopentanoate)→reference example 27→reference example 2→reference example 4→reference example 5 and then purification by column chromatography on silica gel.

TLC (ethyl acetate:n-hexane=1:1): Rf 0.30;

IR (cm$^{-1}$): $\nu$2937, 1713, 1608, 1504, 1471, 1217, 1036.

EXAMPLE 22

3-[1-(5E-7-hydroxy-n-pentadecenyl)oxy-4-(4-dimethylaminocarbonyl-n-butyl)benzen-2-yl]propionic acid

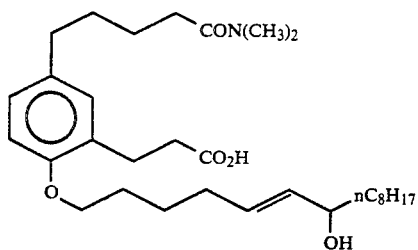

The title compound, of the present invention, having the following physical data was obtained with using the ethyl ester prepared in reference example 31 by the same procedure as reference example 10→reference example 23→reference example 14→reference example 15→reference example 16→reference example 5 and then purification by column chromatography on silica gel.

TLC (ethyl acetate): Rf 0.42;

IR (cm$^{-1}$): $\nu$3402, 2927, 2856, 1728, 1626, 1504, 1468, 1402, 1251, 1161, 1121, 1058, 971, 908, 810, 723.

EXAMPLE 23

3-[1-(5E-7-hydroxy-n-pentadecenyl)oxy-4-dimesylaminobenzen-2-yl]propionic acid

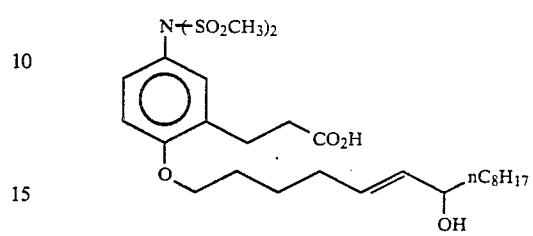

The title compound, of the present invention, having the following physical data was obtained with using the tert-butyl ester prepared in reference example 17 by the same procedure as reference example 10→reference example 18→reference example 20→reference example 11→reference example 12→reference example 13→reference example 14→reference example 15→reference example 16→reference example 5 and then purification by column chromatography on silica gel.

TLC (ethyl acetate): Rf 0.40;

IR (cm$^{-1}$): $\nu$3368, 2921, 2856, 1714, 1504, 1373, 1325, 1261, 1219, 1158, 976, 921, 871, 762.

EXAMPLE 24

3-[1-[6-(4-methoxyphenyl)hex-5E-enyl]oxy-4-(4-carboxylbutyl)benzen-2-yl]propionic acid

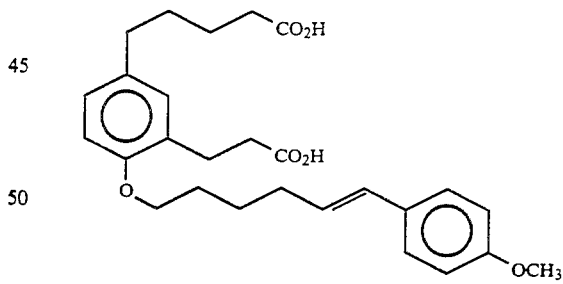

The title compound, of the present invention, having the following physical data was obtained with using the dicarboxylic acid prepared in reference example 29 by the same procedure as reference example 31→reference example 4→reference example 5 and then purification by column chromatography on silica gel.

TLC (ethyl acetate:methanol=6:1): Rf 0.70;

IR (cm$^{-1}$): $\nu$3015, 2938, 2857, 1702, 1610, 1514, 1503, 1473, 1463, 1447, 1422, 1408, 1341, 1305, 1288, 1250, 1202, 1179, 1118, 1040, 1020, 963, 807.

EXAMPLE 24(a)

3-[1-[6-(4-methoxyphenyl)hex-5E-enyl]oxy-4-(5-carboxylpentyl)benzen-2-yl]propionic acid

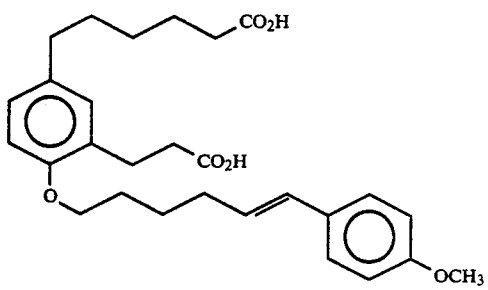

The title compound, of the present invention, having the following physical data was obtained with using a dicarboxylic acid, which was prepared with using 3-(1-methoxybenzen-2-yl)propionic acid by the same procedure as reference example 12→reference example 28 (with the proviso that methyl 5-(chloroformyl)pentanoate was used instead of methyl 4-(chloroformylbutyrate)→reference example 29, by the same procedure as example 24.

TLC (ethyl acetate:methanol=20:1): Rf 0.68;

IR (cm$^{-1}$): ν2932, 2853, 1709, 1609, 1512, 1500, 1465, 1420, 1289, 1245, 1206, 1176, 1128, 1031, 966, 836, 814, 800.

EXAMPLE 25

3-[1-(5E-7-hydroxy-n-pentadecenyl)oxy-4-(4-carboxyl-n-butyl)benzen-2-yl]propionic acid

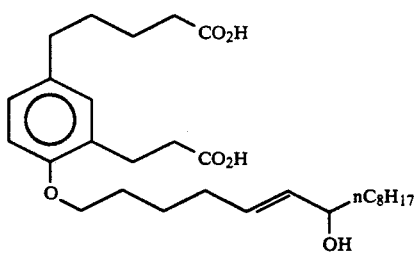

The title compound, of the present invention, having the following physical data was obtained with using the carboxylic acid prepared in reference example 29 by the same procedure as reference example 31→reference example 10→reference example 23→reference example 14→reference example 15→reference example 16→reference example 5 and then purification by column chromatography on silica gel.

TLC (ethyl acetate): Rf 0.33;

IR (cm$^{-1}$): ν3486, 2922, 2855, 1719, 1703, 1611, 1503, 1465, 1447, 1429, 1409, 1311, 1286, 1241, 1199, 1127, 1059, 1001, 975, 960, 806.

EXAMPLE 26

3-[1-[6-(4-methoxyphenyl)hex-5E-enyl]oxy-4-n-butylbenzen-2-yl]propionic acid

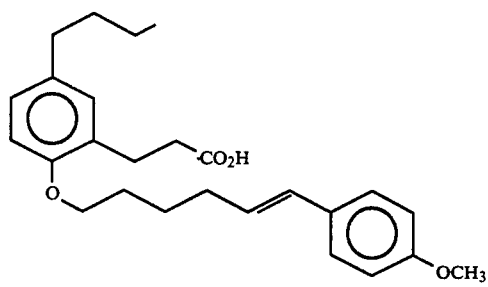

The title compound, of the present invention, having the following physical data was obtained with using 3-(1-methoxybenzen-2-yl)propionic acid by the same procedure as reference example 12→reference example 28 (with the proviso that butyryl chloride was used instead of methyl 4-(chloroformyl)butyrate)→reference example 16→reference example 29→reference example 31→reference example 4→reference example 5 and then purification by column chromatography on silica gel.

TLC (n-hexane:ethyl acetate=2:1): Rf 0.48;

IR (cm$^{-1}$): ν3003, 2931, 2858, 1708, 1609, 1577, 1510, 1467, 1456, 1442, 1290, 1247, 1224, 1175, 1124, 1037, 967, 844, 804.

EXAMPLE 27

3-[1-[6-(4-methoxyphenyl)hex-5E-enyl]oxy-4-(1-oxo-4-carboxylbutyl)benzen-2-yl]propionic acid

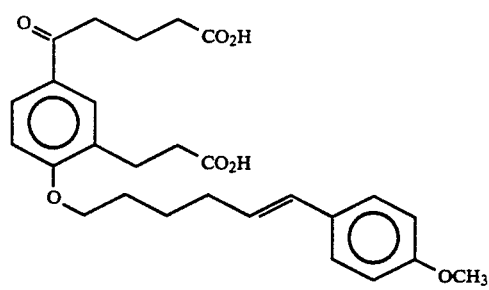

The title compound, of the present invention, having the following physical data was obtained with using the dicarboxylic acid prepared in reference example 32 by the same procedure as reference example 31→reference example 4→reference example 5 and then purification by column chromatography on silica gel.

TLC (ethyl acetate:methanol=9:1): Rf 0.20;

IR (cm$^{-1}$): ν2943, 1697, 1682, 1603, 1510, 1259, 1117

EXAMPLE 27(a)

3-[1-[6-(4-methoxyphenyl)hex-5E-enyl]oxy-4-(1-oxo-5-carboxylpentyl)benzen-2-yl]propionic acid

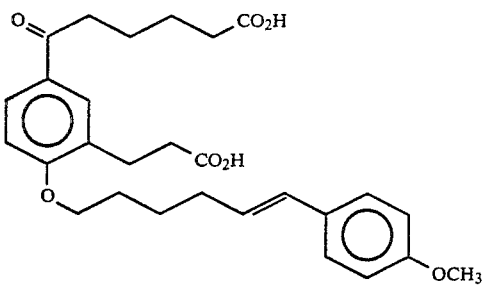

The title compound, of the present invention, having the following physical data was obtained with using a dicarboxylic acid, which was prepared with using 3-(1-methoxybenzen-2-yl)propionic acid by the same procedure as reference example 12→reference example 28 (with the proviso that methyl 4-(chloroformyl)pentanoate was used instead of methyl 4-(chloroformyl)butyrate)→reference example 5→reference example 32, by the same procedure as example 27.

TLC (ethyl acetate:methanol=20:1): Rf 0.45;

IR (cm$^{-1}$): $\nu$2939, 1709, 1694, 1682, 1604, 1578, 1511, 1300, 1260, 1245, 1179, 1116, 1037, 973.

EXAMPLE 28

3-[1-[6-(4-methoxyphenyl)hex-5E-enyl]oxy-4-(1-hydroxy-4-carboxylbutyl)benzen-2-yl]propionic acid

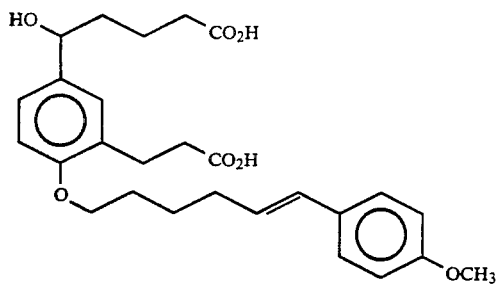

The title compound, of the present invention, having the following physical data was obtained with using the dicarboxylic acid prepared in example 27 by the same procedure as reference example 16.

TLC (ethyl acetate:methanol=9:1): Rf 0.20;

IR (cm$^{-1}$): $\nu$3401, 2938, 1608, 1558, 1511, 1409, 1249, 1176, 1119, 1034, 968, 810.

EXAMPLE 28(a)

3-[1-[6-(4-methoxyphenyl)hex-5E-enyl]oxy-4-(1-hydroxy-5-carboxylpentyl)benzen-2-yl]propionic acid

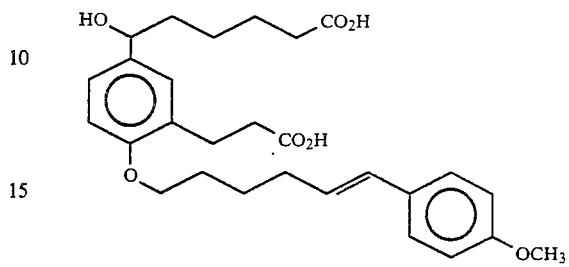

The title compound, of the present invention, having the following physical data was obtained with using the dicarboxylic acid prepared in example 27(a) by the same procedure as example 28.

TLC (ethyl acetate:methanol=20:1): Rf 0.47;

IR (cm$^{-1}$): $\nu$3555, 3032, 2932, 2861, 1703, 1609, 1513, 1503, 1467, 1449, 1427, 1408, 1286, 1250, 1211, 1178, 1122, 1036, 963, 808.

EXAMPLE 29

3-[1-(5E-7-hydroxypentadecenyl)oxy-3-(4-dimethylaminocarbonylbutyl)oxybenzen-2-yl]propionic acid

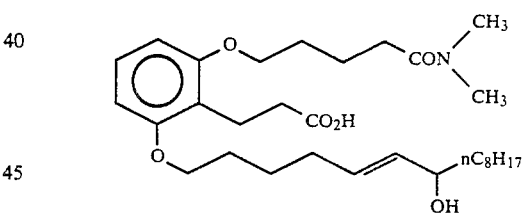

A residue was obtained with using 2,6-dimethoxybenzaldehyde by the same procedure as reference example 24→reference example 2→reference example 25→reference example 26 (with the proviso that N,N-dimethyl-5-bromopentanamide was used instead of ethyl 5-bromopentanoate)→reference example 27→reference example 10→reference example 23→reference example 14→reference example 15→reference example 16→reference example 5. The residue was purified by column chromatography on silica gel (chloroform:methanol=20:1) to give the title compound having the following physical data.

TCL(chloroform:methanol=10:1): Rf 0.44;

IR(cm$^{-1}$): $\nu$2927, 2856, 1723, 1596, 1463, 1402, 1255, 1183, 1161, 1103, 971, 776, 725.

EXAMPLE 30

3-[1-[6-(4-methoxyphenyl)hex-5E-enyl]oxy-3-(4-dimethylaminocarbonylbutyl)oxybenzen-2-yl]propionic acid

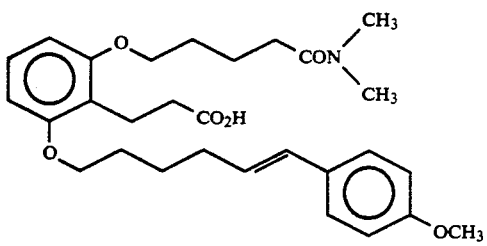

The title compound, of the present invention, having the following physical data was obtained with using 2,6-dimethoxybenzaldehyde by the same procedure as reference example 24→reference example 2→reference example 25→reference example 26 (with the proviso that N,N,dimethyl-5-bromopentanamide was used instead of ethyl 5-bromopentanoate)→reference example 27→reference example 4→reference example 5 and then purification by column chromatography on silica gel.

TLC(chloroform:methanol=10:1): Rf 0.52;
IR(cm$^{-1}$): ν2937, 1723, 1608, 1596, 1511, 1463, 1401, 1250, 1178, 1103, 1035, 969, 846, 776, 756.

EXAMPLE 30(a)

3-[1-[6-(4-methoxyphenyl)hex-5E-enyl]oxy-3-[4-(2-pyrrolidon-1-yl)-n-butoxy]propionic acid

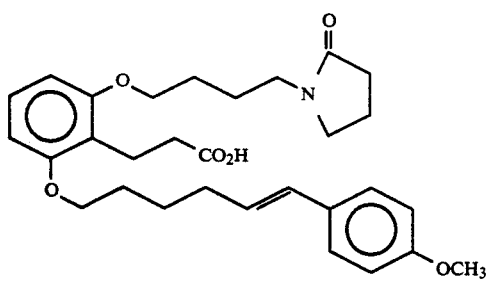

The title compound, of the present invention, having the following physical data was obtained with using 2,6-dimethoxybenzaldehyde by the same procedure as example 30 (with the proviso that 1-bromo-4-(2-pyrrolidon-1-yl)butane was used instead of N,N-dimethyl-5-bromopentanamide)

TLC(chloroform:methanol=10:1): Rf 0.45;
IR(cm$^{-1}$): ν2937, 1723, 1645, 1595, 1511, 1463, 1389, 1250, 1178, 1103, 1035, 969, 847, 756.

EXAMPLE 30(b)

3-[1-[6-(4-methoxyphenyl)hexyl]oxy-3-(4-dimethylaminocarbonylbutyl)oxybenzen-2-yl]propionic acid

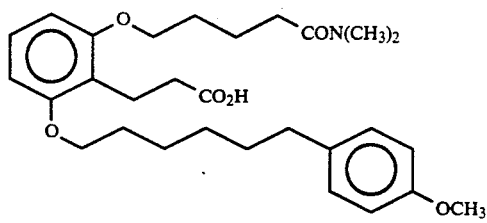

The title compound, of the present invention, having the following physical data was obtained with using 2,6-dimethoxybenzaldehyde by the same procedure as example 30 (with the proviso that 6-(p-methoxyphenyl)-hexanol methansulfonate was used instead of 6-(p-methoxyphenyl)-5E-hexanol methanesulfonate).

TLC(ethylacetate:methanol=9:1): Rf 0.30;
IR(cm$^{-1}$): ν2933, 1724, 1596, 1513, 1463, 1248, 1103.

EXAMPLE 31

3-[1-[6-(4-methoxyphenyl)hex-5E-enyl]oxy-3-(3-carboxylpropyl)oxybenzen-2-yl]propionic acid

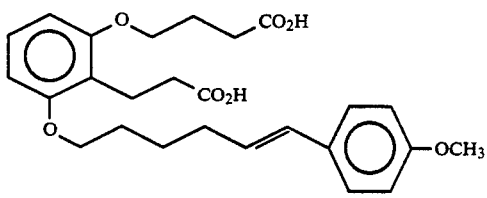

The title compound, of the present invention, having the following physical data was obtained with using 2,6-dimethoxybenzaldehyde by the same procedure as reference example 24→reference example 2→reference example 25→reference example 26 (with the proviso that ethyl 4-bromobutyrate was used instead of ethyl 5-bromopentanoate)→reference example 27→reference example 4→reference example 5 and purification by column chromatography on silica gel.

TLC(chloroform:methanol=10:1): Rf 0.35;
IR(cm$^{-1}$): ν2937, 1707, 1559, 1511, 1463, 1250, 1177, 1104, 1036, 967, 846, 775, 729.

EXAMPLE 31(a)

3-[1-[6-(4-methoxyphenyl)hex-5E-enyl]oxy-3-(4-carboxylbutyl)oxybenzen-2-yl]propionic acid

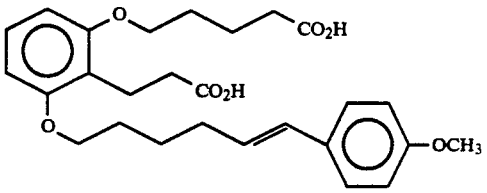

The title compound, of the present invention, having the following physical data was obtained with using 2,6-dimethoxybenzaldehyde by the same procedure as example 31 (with the proviso that ethyl 5-bromopentanoate was used instead of ethyl 4-bromobutyrate).

TLC(chloroform:methanol = 10:1): Rf 0.37;
IR(cm$^{-1}$): ν2937, 1699, 1595, 1510, 1460, 1250, 1180, 1160, 1034, 967, 846, 773, 718.

EXAMPLE 31(b)

3-[1-[6-(4-methoxyphenyl)hexyl]oxy-3-(4-carboxylbutyl)oxybenzen-2-yl]propionic acid

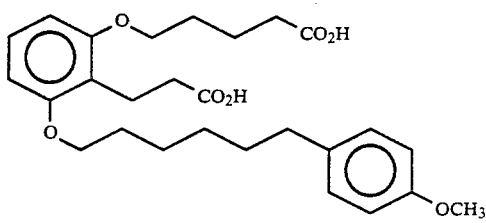

The title compound, of the present invention, having the following physical data was obtained with using the compound prepared in example 31(a) by the same procedure as reference example 2 and then purification by column chromatography on silica gel.

TLC(ethyl acetate:methanol = 9:1): Rf 0.40;
IR(cm$^{-1}$): ν2935, 1702, 1595, 1513, 1461, 1245, 1104.

EXAMPLE 32

3-[1-[6-(4-methoxyphenyl)hex-5E-enyl]oxy-3-(4-dimethylaminocarbonylbutanamido)benzen-2-yl]propionic acid

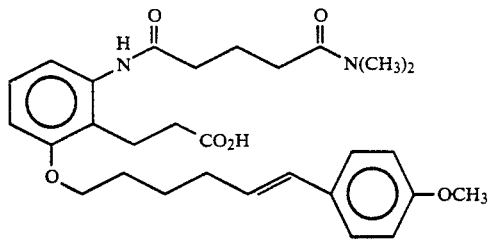

The title compound, of the present invention, having the following physical data was obtained with using 2-hydroxy-6-nitrobenzaldehyde, which was prepared with using 3-nitrophenol by the method described in Bull. Chem. Soc. Japan, 46, 2903 (1973), by the same procedure as reference example 1→reference example 2→reference example 3→reference example 4→reference example 5→refernce example 6 (with the proviso that dimethylamine was used instead of morpholine)-→example 1.

TLC(methylene chloride:methanol = 4:1): Rf 0.52;
IR(cm$^{-1}$): ν2936, 1608, 1511, 1456, 1248, 1176.

EXAMPLE 33

3-[1-[6-(4-methoxyphenyl)hex-5E-enyl]oxy-3-(5-carboxylpentyl)benzen-2-yl]propionic acid

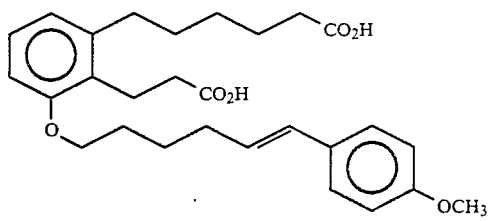

The title compound, of the present invention, having the following physical data was obtained with using an ester, which was prepared with using the ester prepared in reference example 36 by the same procedure as reference example 4, by the same procedure as reference example 5 and then purification by column chromatography on silica gel.

TLC(chloroform:methanol = 10:1); Rf 0.30;
MS: m/z 468(M$^+$), 189;
IR(cm$^{-1}$): ν2930, 1707, 1608, 1583, 1511, 1458, 1248, 1176, 1088, 1037, 967, 846, 756.

EXAMPLE 34

3-[1-[6-(4-methoxyphenyl)hex-5E-enyl]oxy-3-(5-dimethylaminocarbonylpentyl)benzen-2-yl]propionic acid

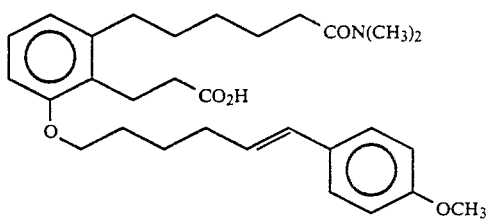

The title compound, of the present invention, having the following physical data was obtained with using the ester prepared in reference example 36 by the same procedure as reference example 25→reference example 6 (with the proviso that dimethylamine was used instead of morpholine)→reference example 27→reference example 4→reference example 5 and then purification by column chromatography on silica gel.

TLC(chloroform:methanol = 10:1): Rf 0.48;
IR(cm$^{-1}$): ν2932, 1724, 1609, 1510, 1458, 1402, 1249, 1176, 1087, 1037, 969, 847, 791, 751.

EXAMPLE 35

3-[1-[6-(4-methoxyphenyl)hex-5E-enyl]oxy-3-dimesylaminobenzen-2-yl]propionic acid

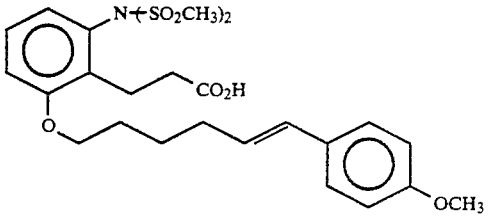

The title compound, in the present invention, having the following physical data was obtained with using 2-hydroxy-6-nitrobenzaldehyde by the same procedure as reference example 1→reference example 2→reference example 17→reference example 4→reference example 18→reference example 20→example 1.

NMR: δ1.67 (2H, m), 1.88 (2H, m), 2.27 (2H, m), 2.73 (2H, m), 3.09 (2H, m), 3.47 (6H, s), 3.80 (3H, s), 4.03 (2H, t), 6.08 (1H, dt), 6.35 (1H, d), 6.79–7.02 (4H, m), 7.18–7.33 (3H, m).

EXAMPLE 36

3-[1-[6-(4-methoxyphenyl)hex-5E-enyl]oxy-3-(perhydro-1,2-thiazin-1,1,3-trione-2-yl)benzen-2-yl]propionic acid

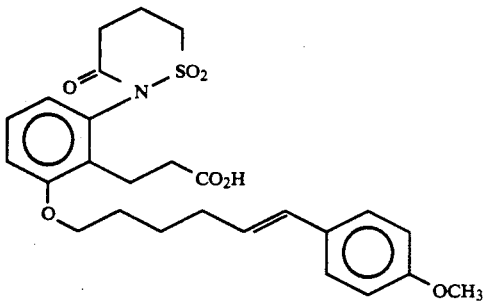

The title compound, of the present invention, having the following physical data was obtained with using 2-hydroxy-6-nitrobenzaldehyde by the same procedure as reference example 1→reference example 2→reference example 17→reference example 4→reference example 18→reference example 3→reference example 5→reference example 22→example 1.

NMR: δ1.66 (2H, m), 1.86 (2H, m), 2.27 (2H, m), 2.44 (2H, m), 2.63 (2H, m), 2.77–3.00 (4H, m), 3.59 (2H, t, J=6 Hz), 3.79 (3H, s), 4.02 (2H, m), 6.08 (1H, dt, J=16 Hz, 7 Hz), 6.35 (1H, d, J=16 Hz), 6.78–6.99 (4H, m), 7.18–7.34 (3H, m).

EXAMPLE 37

3-[1-[6-(4-methoxyphenyl)hex-5E-enyl]oxy-3-(1-oxo-5-carboxylpentyl)benzen-2-yl]propionic acid

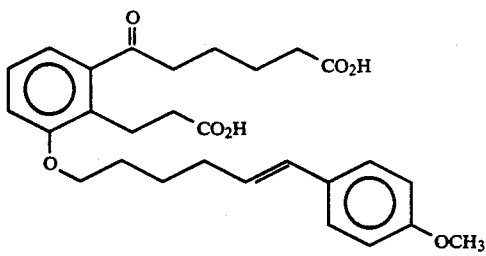

A residue was obtained with using the carboxylic acid prepared in reference example 40 by the same procedure as reference examples 25→reference example 27→reference example 31→reference example 4→reference example 5. The residue was purified by column chromatography on silica gel (chloroform:methanol=20:1→10:1) to give the title compound, of the present invention, having the following physical data.

TLC(chloroform:methanol=10:1): Rf 0.32;

IR(cm$^{-1}$): ν2934, 1706, 1608, 1579, 1511, 1454, 1248, 1176, 1036, 968, 846, 757.

EXAMPLE 38

3-[1-[6-(4-methoxyphenyl)hex-5E-enyl]oxy-3-(1-hydroxy-5-carboxylpentyl)benzen-2-yl]propionic acid

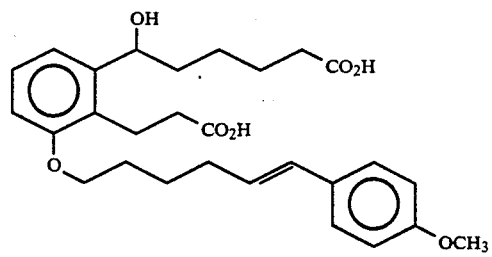

The title compound, of the present invention, having the following physical data was obtained with using the carboxylic acid prepared in example 37 by the same procedure as reference example 16.

TLC(chloroform:methanol=10:1): Rf 0.24;

IR(cm$^{-1}$): ν2937, 1708, 1608, 1585, 1511, 1459, 1250, 1176, 1036, 968, 846, 794, 756.

EXAMPLE 39

3-[1-[6-(4-methoxyphenyl)hex-5E-enyl]oxy-3-(1-oxo-5-dimethylaminocarbonylpentyl)benzen-2-yl]propionic acid

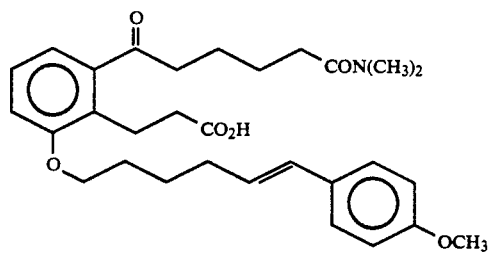

The title compound, of the present invention, having the following physical data was obtained with using the carboxylic acid prepared in reference example 40 by the same procedure as reference example 25→reference example 27→reference example 6 (with the proviso that dimethylamine was used instead of morpholine)→reference example 4→reference example 5 and the purification by column chromatography on silica gel.

TLC(chloroform:methanol=10:1): Rf 0.48;

IR(cm$^{-1}$): ν2942, 1723, 1674, 1626, 1577, 1512, 1453, 1418, 1398, 1250, 1181, 1018, 987, 964, 907, 842, 812, 785, 744.

EXAMPLE 40

3-[1-[6-(4-methoxyphenyl)hex-5E-enyl]oxy-3-(1-hydroxy-5-dimethylaminocarbonylpentyl)benzen-2-yl]propionic acid

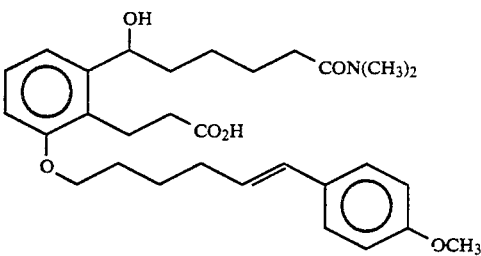

The title compound, of the present invention, having the following physical data was obtained with using the carboxylic acid prepared in example 39 by the same procedure as reference example 16.

TLC(chloroform:methanol = 10:1): Rf 0.35;
IR(cm$^{-1}$): ν2937, 1718, 1608, 1511, 1460, 1403, 1249, 1176, 1067, 1036, 969, 847, 795, 755.

FORMULATION EXAMPLE 1

The following components were admixed in conventional method and punched out to obtain 100 tablets each containing 50 mg of active ingredient.

| | |
|---|---|
| 3-[1-[6-(4-methoxyphenyl)hex-5E-enyl]oxy-3-(4-carboxylbutyl)oxybenzen-2-yl]propionic acid | 5.0 g |
| Cellulose calcium glycolate (carboxymethylcellulose calcium) (disintegrating agent) | 0.2 g |
| Magnesium stearate (Lubricating agent) | 0.1 g |
| Microcrystaline cellulose | 4.7 g |

Names of the compounds in the tables

| Ex. No. | Name |
|---|---|
| 1(a) | 3-[1-[6-(4-methoxyphenyl)hex-5E-enyl]oxy-4-(4-dimethylaminocarbonylbutanamido)benzen-2-yl]propionic acid |
| 1(b) | 3-[1-n-hexyloxy-4-(4-dimethylaminocarbonylbutanamido)benzen-2-yl]propionic acid |
| 1(c) | 3-[1-n-dodecyloxy-4-(4-dimethylaminocarbonylbutanamido)benzen-2-yl]propionic acid |
| 1(d) | 3-[1-n-hexadecyloxy-4-(4-dimethylaminocarbonylbutanamido)benzen-2-yl]propionic acid |
| 1(e) | 3-[1-[6-(4-n-propoxyphenyl)hex-5E-enyl]oxy-4-(4-dimethylaminocarbonylbutanamido)benzen-2-yl]propionic acid |
| 1(f) | 3-[1-[6-[4-(2-propenyl)oxyphenyl]hex-5E-enyl]oxy-4-(4-dimethylaminocarbonylbutanamido)benzen-2-yl]propionic acid |
| 1(g) | 3-[1-[7-(4-methoxyphenyl)hept-6E-enyl]oxy-4-(4-dimethylaminocarbonylbutanamido)benzen-2-yl]propionic acid |
| 1(h) | 3-[1-[7-(4-methoxyphenyl)-n-heptyl]oxy-4-(4-dimethylaminocarbonylbutanamido)benzen-2-yl]propionic acid |
| 1(i) | 3-[1-[6-(4-n-pentyloxyphenyl)hex-5E-enyl]oxy-4-(4-dimethylaminocarbonylbutanamido)benzen-2-yl]propionic acid |
| 1(j) | 3-[1-[6-(4-methoxyphenyl)-n-hexyl]oxy-4-(4-dimethylaminocarbonylbutanamido)benzen-2-yl]propionic acid |
| 1(k) | 3-[1-(7-phenylhept-6E-enyl)oxy-4-(4-dimethylaminocarbonylbutanamido)benzen-2-yl]propionic acid |
| 1(l) | 3-[1-[6-(2-methoxyphenyl)hex-5E-enyl]oxy-4-(4-dimethylaminocarbonylbutanamido)benzen-2-yl]propionic acid |
| 1(m) | 3-[1-[6-(3-methoxyphenyl)hex-5E-enyl]oxy-4-(4-dimethylaminocarbonylbutanamido)benzen-2-yl]propionic acid |
| 1(n) | 3-[1-[6-(4-methoxyphenyl)hex-5E-enyl]oxy-4-[4-(1-indolinyl)carbonylbutanamido]benzen-2-yl]propionic acid |
| 1(o) | 3-[1-[6-(4-methoxyphenyl)hex-5E-enyl]oxy-4-[4-(2-thiazolyl)aminocarbonylbutanamido]benzen-2-yl]propionic acid |
| 1(p) | 3-[1-[6-(4-methoxyphenyl)hex-5E-enyl]oxy-4-(3-dimethylaminocarbonylpropionamido)benzen-2-yl]propionic acid |
| 1(q) | 3-[1-[6-(4-methylthiophenyl)hex-5E-enyl]oxy-4-(4-dimethylaminocarbonylbutanamido)benzen-2-yl]propionic acid |
| 1(r) | 3-[1-[6-(3,4-dimethoxyphenyl)hex-5E-enyl]oxy-4-(4-dimethylaminocarbonylbutanamido)benzen-2-yl]propionic acid |
| 1(s) | 3-[1-[6-(4-methylphenyl)hex-5E-enyl]oxy-4-(4-dimethylaminocarbonylbutanamido)benzen-2-yl]propionic acid |
| 1(t) | 3-[1-[6-(4-chlorophenyl)hex-5E-enyl]oxy-4-(4-dimethylaminocarbonylbutanamido)benzen-2-yl]propionic acid |
| 1(u) | 3-[1-[6-(4-methoxyphenyl)hex-5E-enyl]oxy-4-(3-dimethylaminocarbonylbenzamido)benzen-2-yl]propionic acid |
| 2(a) | 3-[1-[6-(4-methoxyphenyl)hex-5E-enyl]oxy-4-(4-carboxylbutanamido)benzen-2-yl]-E-acrylic acid |
| 2(b) | 3-[1-[6-(4-methoxyphenyl)hex-5E-enyl]oxy-4-(3-carboxylbenzamido)benzen-2-yl]propionic acid |
| 3(a) | 3-[1-[6-(4-methoxyphenyl)hex-5E-enyl]oxy-4-benzamidobenzen-2-yl]propionic acid |
| 3(b) | 3-[1-[6-(4-methoxyphenyl)hex-5E-enyl]oxy-4-decanamidobenzen-2-yl]propionic acid |
| 3(c) | 3-[1-[6-(4-methoxyphenyl)hex-5E-enyl]oxy-4-acetamidobenzen-2-yl]propionic acid |
| 4(a) | 3-[1-[6-(4-methoxyphenyl)hex-5E-enyl]oxy-4-(4-hydroxybutanamido)benzen-2-yl]propionic acid |
| 4(b) | 3-[1-[6-(4-methoxyphenyl)hex-5E-enyl]oxy-4-(3-hydroxymethylbenzamido)benzen-2-yl]propionic acid |
| 5(a) | 3-[1-(4E-6-hydroxytetradecenyl)oxy-4-dimethylaminocarbonylbutanamidobenzen-2-yl]propionic acid |
| 5(b) | 3-[1-(5E-7-hydroxydodecenyl)oxy-4-dimethylaminocarbonylbutanamidobenzen-2-yl]propionic acid |
| 5(c) | 3-[1-[5E-7-hydroxy-9-(4-methoxyphenyl)nonenyl]oxy-4-dimethylaminocarbonylbutanamidobenzen-2-yl]propionic acid |
| 5(d) | 3-[1-(5E-7-hydroxynonenyl)oxy-4-dimethylaminocarbonylbutanamidobenzen-2-yl]propionic acid |
| 5(e) | 3-[1-(5E-7-hydroxy-7-cyclohexylheptenyl)oxy-4-dimethylaminocarbonylbutanamidobenzen-2-yl]propionic acid |
| 6(a) | 3-[1-[6-(4-methoxyphenyl)hex-5E-enyl]oxy-4-(4-methylphenyl)sulfonylaminobenzen-2-yl]propionic acid |
| 6(b) | 3-[1-[6-(4-methoxyphenyl)hex-5E-enyl]oxy-4-methyl sulfonylaminobenzen-2-yl]propionic acid |
| 6(c) | 3-[1-[6-(4-methoxyphenyl)hex-5E-enyl]oxy-4-benzylsulfonylaminobenzen-2-yl]propionic acid |
| 10(a) | 3-[1-[6-(4-methoxyphenyl)hex-5E-enyl]oxy-4-ditosylaminobenzen-2-yl]propionic acid |
| 10(b) | 3-[1-[6-(4-methoxyphenyl)hex-5E-enyl]oxy-4-bis(n-butylsulfonyl)aminobenzen-2-yl]propionic acid |
| 10(c) | 3-[1-[6-(4-methoxyphenyl)hex-5E-enyl]oxy-4-bis(benzylsulfonyl)aminobenzen-2-yl]propionic acid |
| 12(a) | 3-[1-[6-(4-methoxyphenyl)hexyl]oxy-4-(perhydro-1,2-thiazin-1,1,3-trione-2-yl)benzen-2-yl]propionic acid |
| 12(b) | 3-[1-[6-(4-methoxyphenyl)hex-5E-enyl]oxy-4-(isothiazolidin-1,1,3-trione-2-yl)benzen-2-yl]propionic acid |
| 15(a) | 3-[1-[5E-7-hydroxy-9-(4-methoxyphenyl)nonenyl]oxy-4-(4-carboxylbutyl)oxybenzen-2-yl]propionic acid |
| 15(b) | 3-[1-(5E-7-hydroxypentadecenyl)oxy-4-(3-carboxylpropyl)oxybenzen-2-yl]propionic acid |
| 15(c) | 3-[1-(5E-7-hydroxypentadecenyl)oxy-4- |

| Ex. No. | Name | |
|---|---|---|
| | carboxylmethoxybenzen-2-yl]propionic acid | |

What is claimed is:

1. A phenylkan(en)oic acid of the formula:

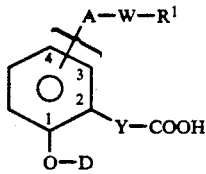 (I)

wherein

A, taken together with W and R¹, is
i)

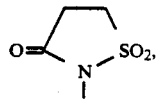

Y is ethylene or vinylene;
D is
i) —Z—B or
ii)

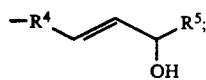

Z is C3-11 alkylene or alkenylene

B is

or

Z, taken together with B, is C3-22 alkyl;
$R^3$ is
  i) hydrogen,
  ii) halogen,
  iii) C1-8 alkyl, alkoxy or alkylthio or
  iv) C2-8 alkenyl, alkenyloxy or alkenylthio;
n is 1-3;
$R^4$ is C1-7 alkylene;
$R^5$ is
  i) C1-12 alkyl,
  ii) C2-12 alkenyl,
  iii) C5-7 cycloalkyl or
  iv) phenethyl or phenethyl wherein the ring is substituted by one C1-4 alkoxy;
with the proviso that —A—W—R¹ should bind to 3- or 4- carbon in benzene ring and non-toxic salts thereof.

2. A compound according to claim 1, which is 3-[1-[6-(4-methoxyphenyl)hex-5E-enyl]oxy-4-(isothiazolidin-1,1,3-trione-2-yl)benzen-2-yl]propionic acid.

3. A pharmaceutical composition for diseases induced by leukotrien B₄ which comprise, as active ingredient, an effective amount of the phenylalkan(en)oic acid of the formula (I) as claimed in claim 1, or the pharmaceutically acceptable acid addition salts thereof.

4. A method for the prevention and treatment of several diabetic complications, diseases induced by leukotriene B₄, which comprises the administration of an effective amount of the phenylalkan(en)oic acid of the formula (I) as claimed in claim 1, or the pharmaceutically acceptable acid addition salts thereof.

* * * * *